United States Patent
Tanaka et al.

(10) Patent No.: US 10,059,956 B2
(45) Date of Patent: Aug. 28, 2018

(54) GLYCOSYLTRANSFERASE GENE AND USE THEREOF

(71) Applicant: SUNTORY HOLDINGS LIMITED, Osaka-shi, Osaka (JP)

(72) Inventors: Yoshikazu Tanaka, Mishima-gun (JP); Naoko Okitsu, Mishima-gun (JP); Keisuke Matsui, Mishima-gun (JP)

(73) Assignee: SUNTORY HOLDINGS LIMITED, Osaka-shi, Osaka (JP)

( * ) Notice: Subject to any disclaimer, the term of this patent is extended or adjusted under 35 U.S.C. 154(b) by 493 days.

(21) Appl. No.: 14/372,232

(22) PCT Filed: Jan. 16, 2013

(86) PCT No.: PCT/JP2013/050689
§ 371 (c)(1),
(2) Date: Jul. 15, 2014

(87) PCT Pub. No.: WO2013/108794
PCT Pub. Date: Jul. 25, 2013

(65) Prior Publication Data
US 2015/0203862 A1    Jul. 23, 2015

(30) Foreign Application Priority Data
Jan. 17, 2012  (JP) .................................. 2012-007105

(51) Int. Cl.
| | | |
|---|---|---|
| C12N 15/82 | (2006.01) | |
| C12P 19/18 | (2006.01) | |
| C12N 9/10 | (2006.01) | |
| C12P 19/60 | (2006.01) | |
| A61K 8/60 | (2006.01) | |
| A61Q 19/00 | (2006.01) | |
| A61K 31/7048 | (2006.01) | |
| C07H 21/00 | (2006.01) | |
| A23L 33/10 | (2016.01) | |
| A23L 33/18 | (2016.01) | |

(52) U.S. Cl.
CPC .......... *C12N 15/8257* (2013.01); *A23L 33/10* (2016.08); *A23L 33/18* (2016.08); *A61K 8/602* (2013.01); *A61K 31/7048* (2013.01); *A61Q 19/00* (2013.01); *C07H 21/00* (2013.01); *C12N 9/1048* (2013.01); *C12N 9/1051* (2013.01); *C12N 15/825* (2013.01); *C12P 19/18* (2013.01); *C12P 19/60* (2013.01); *A61K 2800/10* (2013.01)

(58) Field of Classification Search
None
See application file for complete search history.

(56) References Cited

U.S. PATENT DOCUMENTS

| | | |
|---|---|---|
| 8,093,028 B2 | 1/2012 | Thorson et al. |
| 2005/0003476 A1 | 1/2005 | Mizutani et al. |
| 2005/0257291 A1 | 11/2005 | Mizutani et al. |
| 2006/0174377 A1 | 8/2006 | Nakamura et al. |
| 2010/0256345 A1 | 10/2010 | Ochiai et al. |
| 2010/0287667 A1 | 11/2010 | Tanaka et al. |
| 2010/0287668 A1 | 11/2010 | Tanaka et al. |
| 2010/0306877 A1 | 12/2010 | Tanaka et al. |
| 2011/0126320 A1 | 5/2011 | Tanaka et al. |
| 2012/0096589 A1 | 4/2012 | Noda et al. |

FOREIGN PATENT DOCUMENTS

| | | |
|---|---|---|
| JP | H09-118611 A | 5/1997 |
| JP | 09143070 A * | 6/1997 |
| JP | H09-143070 A | 6/1997 |
| JP | 2005-095005 A | 4/2005 |
| JP | 2006-149293 A | 6/2006 |
| KR | 20110110882 A | 10/2011 |
| WO | WO-99/05287 A1 | 2/1999 |
| WO | WO-01/92509 A1 | 12/2001 |
| WO | WO-2005/017147 A1 | 2/2005 |
| WO | WO-2006/105598 A1 | 10/2006 |
| WO | WO-2007/094521 A1 | 8/2007 |
| WO | WO-2008156211 A1 | 12/2008 |
| WO | WO-2008156214 A1 | 12/2008 |
| WO | WO-2009/062253 A1 | 5/2009 |

(Continued)

OTHER PUBLICATIONS

Bowles et al., 2005, Current Opinion in Plant Biology 8: 254-263.*
Keskin et al., 2004, Protein Science 13: 1043-1055.*
Guo et al., 2004, Proceedings of the National Academy of Sciences USA 101: 9205-9210.*
Thornton et al., 2000, Nature Structural Biology, structural genomic supplement, Nov. 2000: 991-994.*
Vogt et al., 1999, The Plant Journal 19: 509-519.*
Ross et al., 2001, Genome Biology 2001, 2(2):reviews3004.1-3004.6.*

(Continued)

*Primary Examiner* — Amjad Abraham
*Assistant Examiner* — Bratislav Stankovic
(74) *Attorney, Agent, or Firm* — Drinker Biddle & Reath LLP

(57) ABSTRACT

Provided is a polynucleotide encoding a protein having activity that transfers a sugar to the hydroxyl group at the 4'-position of a flavone, wherein the polynucleotide is selected from the group consisting of: (a) a polynucleotide composed of the base sequence of SEQ ID NO: 1; (b) a polynucleotide that hybridizes under stringent conditions with a polynucleotide composed of a base sequence complementary to the base sequence of SEQ ID NO: 1; (c) a polynucleotide encoding a protein composed of the amino acid sequence of SEQ ID NO: 2; and, (d) a polynucleotide encoding a protein composed of an amino acid sequence in which one or a plurality of amino acids have been deleted, substituted, inserted and/or added in the amino acid sequence of SEQ ID NO:2.

11 Claims, 22 Drawing Sheets

Specification includes a Sequence Listing.

(56) References Cited

FOREIGN PATENT DOCUMENTS

| WO | WO-2010/026666 A1 | 3/2010 |
|---|---|---|
| WO | WO-2010/122849 A1 | 10/2010 |
| WO | WO-2012/096307 A1 | 7/2012 |

OTHER PUBLICATIONS

Maniatis et al., 1982, Molecular Cloning: A Laboratory Manual, Cold Spring Harbor Laboratory, pp. 324-343 and 387-389.*

Yoshida et al., 2009, Natural Products Reports 26: 857-964.*

Kumi Yoshida, et al., "Blue flower color development by anthocyanins: from chemical structure to cell physiology", Natural Product Reports, 2009, 26, pp. 884-915.

Yoshikazu Tanaka, et al., "Flower Color Modification by Engineering of the Flavonoid Biosynthetic Pathway: Practical Perspectives", Biosci. Biotechnol. Biochem., 2010, 74(9), pp. 1760-1769.

Yukihisa Katsumoto et al., "Engineering of the Rose Flavonoid Biosynthetic Pathway Successfully Generated Blue-Hued Flowers Accumulating Delphinidin", Plant Cell Physiol., 2007, 48(11), pp. 1589-1600.

Yoshikazu Tanaka, et al., "Molecular and Biochemical Characterization of Three anthocyanin Synthetic Enzymes from *Gentiana triflora*", Plant Cell Physiol., 1996, 37(5), pp. 711-716.

Mami Yamazaki, et al., "Molecular Cloning and Biochemical Characterization of a Novel Anthocyanin 5-O-Glucosyltransferase by mRNA Differential Display for Plant Forms Regarding Anthocyanin", J. Biol. Chem., Mar. 12. 1999, 274(11), pp, 7405-7411.

Mami Yamazaki, et al.,"Two flavonoid glucosyltransferases from *Petunia hybrida*: molecular cloning, biochemical properties and developmentally regulated expression", Plant Molecular Biology, 2002, 48, pp. 401-411.

Takashi Nakatsuka, et al., "Cloning and characterization of the UDP-glucose:anthocyanin 5-O-glucosyltransferase gene from blue-flowered gentian", Journal of Experimental Botany, 2008, 59(6), pp. 1241-1252.

Jeong Ho Kim, et al., "Characterization of Flavonoid 7-O-Glucosyltransferase from *Arabidopsis thialana*", Biosci. Biotechnol. Biochem., 2006. 70(6), pp. 1471-1477.

Maso Hirotani, et al., "Cloning and expression of UDP-glucose: flavonoid 7-O-glucosyltranferase from hairy root cultures of *Scutellaria baicalensis*" Planta, 2000, 210, pp. 1006-1013.

Yuki Matsuba, et al., "A Novel Glucosylation Reaction on Anthocyanins Catalyzed by Acyl-Glucose-Dependent Glucosyltransferase in the Petals of Carnation and Delphinium", The Plant Cell, 2010, 22(10), pp. 3374-3389.

Thomas Vogt, et al., "Cloning and expression of cDNA encoding betanidin 5-O-glucosyltransferase, a betanidin- and flavonoid-specific enzyme with high homology to inducible glycosyltransferases from the Solanaceae", The Plant Journal, 1999, 19(5), pp. 509-519.

Supplemental European Search Report dated Mar. 3, 2015 in European Application No. 13738880.7.

Database Geneseq [Online] Accession No. AZN73730, "Bacillus licheniformis UDP—glycosyl transferase C protein, SEQ ID 1", Dec. 8, 2011, XP-002736049.

Andrew C. McCall, "Natural and artificial floral damage induces resistance in *Nemophila menziesii* (Hydrophyllaceae) flowers", OIKOS, Mar. 1, 2006, vol. 112, No. 3, pp. 660-666.

Gamei She, et al., "New Flavonoid Glycosides from *Elsholtzia rugulosa* Hemsl.", Molecules, Oct. 20, 2009, vol. 14, No. 10, pp. 4190-4196.

Rit Bahadur Gurung, et al., "Enzymatic Synthesis of Apigenin Glucosides by Glucosyltransferase (YjiC) from *Bacillus licheniformis* DSM 13", Molecules and Cells, Oct. 1, 2013, vol. 36, No. 4, pp. 355-361.

Rubio, et al., "Cloning and characterization of a glucosyltransferase from *Crocus sativus* stigmas involved in flavonoid glucosylation", BMC Plant Biology, Aug. 20, 2009, vol. 9, p. 109.

Yuki Matsuba et al., "A Novel Glucosylation Reaction on Anthocyanins Catalyzed by Acyl-Glucose-Dependent Glucosyltransferase in the Petals of Carnation and Delphinium," American Society of Plant Biologists, The Plant Cell, Oct. 2010, pp. 3374-3389, vol. 22.

Akio Noguchi et al., "Local Differentiation of Sugar Donor Specificity of Flavonoid Glycosyltransferase in Lamiales," American Society of Plant Biologists, The Plant Cell, May 2009, pp. 1556-1572, vol. 21.

Simone Witte et al., "Recombinant expression and functional characterisation of regiospecific flavonoid glucosyltransferases from *Hieracium pilosella* L.," Planta, 2009, pp. 1135-1146, vol. 229.

International Search Report (ISR) dated Apr. 23, 2013 in PCT/JP2013/050689 filed on Jan. 16, 2013.

* cited by examiner

FIG. 11

| | NmGT8 | Dbs5GT |
|---|---|---|
| Pel | × | (×) |
| Pel3Glc | × | |
| Cya | × | △(Cya4'Glc) |
| Cya3Glc | × | |
| Del | × | |
| Del3Glc | × | |
| Pet | × | |
| Mal | × | |
| Api | ◎(Api4'Glc) | (×) |
| Api7Glc | × | |
| Lut | ◎(Lut4'Glc) | △(Lut4'Glc,Lut7Glc) |
| Lut7Glc | × | |
| Lut4'Glc | × | |
| Tri | × | |
| K | ○(K3Glc) | (×)(K4'Glc) |
| K3Glc | × | |
| Q | ○ | ○(Q4'Glc,Q7Glc) |
| Q3Glc | × | |
| M | × | △(M4'Glc,M7Glc) |
| Narigenin | × | |
| betanidin | × | ○(betanidin5Glc) |

↑ Source : Thesis Database(Thomas Vogt, 1997, 1999)

Enzyme reaction process
◎ : Reacts strongly and completely uses substrate
○ : Reacts
△ : Reacts, but hardly any product formed
× : Does not react at all
(×) : Hardly reacts at all ( ) : Reaction biosynthesis product
Cya4'Glc : Cyanidin 4'-glucoside
Api4'Glc : Apigenin 4'-glucoside
Api7Glc : Apigenin 7-glucoside
Api4',7Glc : Apigenin 4',7-diglucoside
Lut4'Glc : Luteolin 4'-glucoside
Lut7Glc : Luteolin 7-glucoside
Lut4',7Glc : Luteolin 4',7-diglucoside
K3Glc : Kaempferol 3-glucoside
K4'Glc : Kaempferol 4'-glucoside
Q3Glc : Quercetin 3-glucoside
Q4'Glc : Quercetin 4'-glucoside
Q7Glc : Quercetin 7-glucoside
M4'Glc : Myricetin 4'-glucoside
M7Glc : Myricetin 7-glucoside
betanidin5Glc : Betanidin 5-glucoside

FIG. 12-1

```
NmGT3    1  MPSILSNSAH ILLFPFPTSG HIIPILDLAN QLLARGLTIT LITPANLTL   94
NmGT8    1  -----MEKKT IILYPSPGIG HLVSMVELAK LILNREPSYS IIIFISSAPY   95

NmGT3   95  LSTQLIELDRLG SLHTLVLPFFPNP-----PNPSETSLAARVHASSQLSN-         
NmGT8   96  STGSSAPYISHV SATTSGISFHHLPVLVLPPNTFSSFEEIAYKIPQLNNP

NmGT3   95  ----TIIQWFQSHTSPPVAIVSDFFFLGWTNSLASQLGIPRLVFWPSGVQRS   191
NmGT8   96  NLKLALQTISKESSDLKAFIIDFFCTAAVEVSSNLEIPTYFFFTSGSSAM    190

NmGT3  192  SLVDYIWQNDQLSDSDHQIQDNSVISFPDVPNSPAYPKWQACGLSTQYKK
NmGT8  191  CQFLYLPTLHETITQKDLQDPNTYVHIPGIP----PIHSLDLPKVLSNR

NmGT3  192  GDPSWEFFKNGVLANTQSWGAIYNSFRDLEGVYYIDYIKKMGHG-----R    286
NmGT8  191  STVLYKELINTANQMAKCSGILILINAFETLEPKAVKALKEGLCTPGMPTPP  285

NmGT3  287  VWAVGPLLPANDASKRGGSCVMPIDDVMTWLDTKTNSDNSVVYVCFGSRV
NmGT8  286  VYCIGPLIASGDK---GNVNDAHGHEILTWLNSQPS--KSVVFLCFGSLG

NmGT3  287  ELTTEQLDSLAAALEISGVHFILCVK----------LHQEIS           368
NmGT8  286  TFKEDQLKEIAIGLENSGHRFLWVMKSPPIDDKTKRFLPPEPDFNVLLP    385

NmGT3  369  KEYEDRVAGRGLIIRGWAPQVAILRHRAVGAFLTHCGWNSILEGIAAGVV
NmGT8  386  EGFLERTKERGVIVKSWAPQLAILNHDAIGGFVTHCGWNSVLEACGGVP

NmGT3  369  MLTWPMGADQFTNANLLVDELKVAMKACEGGDSNVPNPAMLANVLAES-I   464
NmGT8  386  MLAWPLYAEQRVNRVCMVEEMKVALPLEESVDGFVMASEIEKRVKELVDY  474

NmGT3  369  NGGRAERERVTELCDAALKAVQSGNGSSAKDLDSLTNQLNGLKVKIN----
NmGT8  386  ESSEAIRDQVKIMSEKAKTAVAVSGSS----HDALTKLLDGWK-----
```

FIG. 12-2

```
NmGT4   1   MAAQLHVVFFPFMAQGHLIPTLEMVKLFSSRGLKTTIVTTKFYAPAVTKS
NmGT8   1   -MEKKTIILYPSPGIGHLVSMVELAKLILNREPSYSIIIFISSAPYSTGS  100
                                                                   99

IEKTKHTGNQINIIIKFPSAEVGLPEGSESLDKLKSPDMFMKFFKALSL
            SAPYISHVSATTSGISFHHLPVLVLPPNTFSSFEEIAYKIPQLNNPNLKL

NmGT4  101  LQEPFEQILQELSPDCIVSDMFFPWTTASAAKFDIPRFVFHGLSLFALCV
NmGT8  100  ALQTISKESSDLK--AFIIDFFCTAAVEVSSNLEIPTYFFFTSGSSAMCQ

SENMRFYKPFKNLGSESLDSEPVMLPDFPNQIEFSKVQVPEFEVGESKNE  200
            FLYLPTLHETITQKDLQDPNTYVHIPGIP---PIHSLDLPKVLSNRSTVL  194

NmGT4  201  IMELLNQVKESEVKSYGIIINSFNELEKDYVDYYRN-----VWGRRAWL
NmGT8  195  YKELINTAN-QMAKCSGILINAFEETLEPKAVKALKEGLCTPGMPTPPVYC

LGPLSLSNRDDEVKDQTDEHGSLKWLDSKKPDSVIYVCFGSVAPLSSSQL  294
            IGPLIASG-DKGNVNDAHGHEILTWLNSQPSKSVFLCFGSLGTFKEDQL  292

NmGT4  295  HEIALGLESSGQQFIWVVKE------REDGEKWLPEGFEERI
NmGT8  293  KEIAIGLENSGHRFLWYMKSPPIDDKTKRFLPPPEPDFNVLLPEGFLERT

KDKGLIIRGWAPQVSILEHESTGGFVTHCGWNSVLEAVSAGVVMATLPTF  380
            KERGVIVKSWAPQLAILNHDAIGGFVTHCGWNSVLEAICGGVPMLAWPLY  392

NmGT4  381  AEQPFNEKLLTKVLKIGIPIGSPLSNRGKSGVKKEEIAEAMKGIMEGEEA
NmGT8  393  AEQRVNRVCMVEEMKVALPLEEESVDG----FVMASEIEKRVKELVDYESS

LEMRIRAKSLKEMAWKAVEEGGSSYNDLTSLIDGVKAYRSQSNKI-----  475
            EAIRDQVKKIMSEKAKTAVAVSGSSHDALTKLLDGWK-------------  474
```

```
Antirrhinum-chalcone4'GT    1  MGEEYKKTHTIVFHTSEEHLNSSIALAKFITKHHSSISITI-ISTAPAE
NmGT8                       1  ---MEKKTIILYPSPGIGHLVSMVELAKLILNREPSYSIIFISSAPYS
                               SSEVAKIINNPSITYRGLTAVALPEN-LTSNINKNPVELFFEIPRLQNANL   98
                               TGSSAPYISHVSATTSGISFHHLPVLVPPNTFSSFEEIAYKIPQLNNPNL    97

Antirrhinum-chalcone4'GT   99  REALLDISRKS-DIKALIIDFFCNAAFEVSTSMNIPTYFDVSGGAFLLC
NmGT8                      98  KLALQTLSKESSDLKAFIIDFFCTAAVEVSSNLEIPTYFFFTSGSSAMC
                               TFLHHPTLHQTVRG-DIADLNDSVEMPGFPLIHSSDLPMSLFYRKTNVYKH   196
                               QFLYLPTLHEITTQKDLQDPNTYVHIPGIPPIHSLDLPKVLSNRSTVLYKE   197

Antirrhinum-chalcone4'GT  197  FLDTSLNMRKSSGILVNTFVALEFRAKEALSNGLYGP---TPPLYLLSH
NmGT8                     198  LINTANQMAKCSGILLINAFEETLEPKAVKALKEGLCTPGMPTPPVYYCIGP
                               TIAEPHDTKV-LVNQHECLSWLDLQPSKSVIFLCFGRRGAFSAQQLKEIAI   292
                               LIASGDKGNNDAHGHEILTWLNSQPSKSVVFLCFGSLGTFKEDQLKEIAI   297

Antirrhinum-chalcone4'GT  293  GLEKSGCRFLWLARIS------PEMDLNALLPEGFLSRTKGVG
NmGT8                     298  GLENSGHRFLWVMKSPPIDDKTKRFLPPPEPDFNVLLPEGFLERTKERG
                               FVTNTWVPQKEVLSHDAVGGFVTHCGWSSVLEALSFGVPMIGWPLYAEQRI   380
                               VIVKSWAPQLAILNHDAIGGFVTHCGWNSVLEAICGGVPMLAWPLYAEQRV   397

Antirrhinum-chalcone4'GT  381  NRVFMVEEIKVALPLDE-EDGFVTAMELEKRVRELMESVKGKEVKRRVA
NmGT8                     398  NRVCMVEEMKVALPLEESVDGFVMASEIEKRVKELVDYESSEAIRDQVK
                               ELKISTKAAVSKGGSSLASLEKFINSVTR-      457
                               IMSEKAKTAVAVSGSSHDALTKLLDGWK-       474
```

FIG. 14

```
rose_Anthocyanidin_5,3-GT    1  M G G D A I V L Y P Y P G L G H L I S M V E L G K L L L T H H P S F S I T I L A S T A P T T I A A  99
NmGT8                        1  M E K K T I I L L Y P S P G I G H L V S M V E L A K L I L N R E P S Y S I I L F I S S A P Y S T G S  89 rose_Anthocyanidin_5,3-GT  100  T A K L V A S S N D Q L T N Y I K A V S A D N P A I N F H H L P T I S S L P E H I E K L N - L P F E Y  194
NmGT8                       90  S A P - - - - - - - - - - - Y I S H V S A T T S G I S F H H L P V L P P N T F S S F E E I A Y K I      188 rose_Anthocyanidin_5,3-GT  195  A R L Q I P N I L Q V L Q T L K - - S S L E K A L I L D M F C D A L F D V T K D L N I P T F Y F Y     290
NmGT8                       189 P Q L N N P N L K L A L Q T I S K E S S D L K A F I I D F F C T A A V E V S S N L E I P T Y F F F     288 rose_Anthocyanidin_5,3-GT  291  T S A G R S L A V L L N I P T F H R - - T T N S L S D F G D V P I S I S G M P P I P V S A M P K L L F 385
NmGT8                       289 T S G S S A M C Q F L Y L P T L H E T I T Q K D L Q D P - N T Y V H I P G I P P I H S L D L P K V L L S 388 rose_Anthocyanidin_5,3-GT  386  D R S T N F Y K S F L S T S T H M A K S N G I I L N T F D L L E E R A L K A L R A G L C L P N Q P T P P
NmGT8                       389 N R S T V L Y K E L I N T A N Q M A K C S G I L I N A F E T L E P K A V K A L K E G L C T P G M P T P P rose_Anthocyanidin_5,3-GT       I F T V G P L I S - - - - G K S G D N D E H E S L K W L N N Q P K D S V V F L C F G S M G V F S       290
NmGT8                           V Y C I G P L I A S G D K G N V N D A H G H E E I L T W L N S Q P S K S V V F L C F G S L G T F K       288 rose_Anthocyanidin_5,3-GT       I K Q L E A M A L G L E K S G Q R F L W V V R N P P I E E - - - - - L P V E E P S L E E I L P K G F   385
NmGT8                           E D Q L K E I A I G L E N S G H R F L W V M K S P P I D D K T K R F L P P P E P D F N V L L P E G F   388 rose_Anthocyanidin_5,3-GT       V E R T K D R G L V V R K W A P Q V E V L S H D S V G G F V T H C G W N S V L E A V C N G V P M V A   385
NmGT8                           L E R T K E R G V I V K S W A P Q L A I L N H D A I G G F V T H C G W N S V L E A I C G G V P M L A   388 rose_Anthocyanidin_5,3-GT       W P L Y A E Q K L G R V F L V E E M K V A V G V K E S E T G F V S A D E L E K R V R E L M D S E S      473
NmGT8                           W P L Y A E Q R V N R V C M V E E M K V A L P L E E S V D G F V M A S E I E K R V K E L V D Y E S      474 rose_Anthocyanidin_5,3-GT       G D E I R G R V S E F S N G G V K A K E E G G S S V A S L A K L A Q L W K Q K - -  473
NmGT8                           S E A I R D Q V K I M S E K A K T A V A V S G S S H D A L T K L L D G W K - -      474
```

GLYCOSYLTRANSFERASE GENE AND USE THEREOF

CROSS REFERENCE TO RELATED APPLICATIONS:

This application is the National Stage of International Application No. PCT/JP2013/050689 filed Jan. 16, 2013 and claims benefit of Japanese Application No. 2012-007105 filed on Jan. 17, 2012.

SEQUENCE LISTING

The instant application contains a Sequence Listing which has been submitted electronically in ASCII format and is hereby incorporated by reference in its entirety. Said ASCII copy, created on Mar. 19, 2015, is named 047237-5034-00-US-514550_SL.txt and is 81,993 bytes in size.

TECHNICAL FIELD

The present invention relates to a polynucleotide that encodes a protein having activity that transfers a sugar to the hydroxyl group at the 4'-position of a flavone.

BACKGROUND ART

Flowers having new traits are always valued in the flower industry. In particular, the development of plants in which "color", which is considered to be the most important trait of a flower, has been altered is considered to be industrially important, and various flower colors have been developed through selective breeding using the classical method of crossbreeding. Although crossbreeding is an effective method for selective breeding, since there are genetic restrictions unique to plants, this method has the shortcoming of only being able to use genetic resources possessed by related species capable of crossbreeding. For example, despite many years of selective breeding, violet to blue-colored varieties of roses, carnations, chrysanthemums and lilies, vivid red-colored varieties of gentians and irises, and yellow varieties of morning glories have yet to be produced.

Flower color originates in four types of pigments consisting of flavonoids, carotenoids, chlorophyll and betalain. Among these, flavonoids exhibit a diverse range of colors such as yellow, red, violet and blue. The group that exhibits red, violet and blue color is generically referred to as anthocyanins, and the diverse structure of anthocyanins is one of the causes of the diverse range of flower color. Anthocyanins can be broadly divided into three groups according to their aglycon structure in consideration of the biosynthesis pathway thereof. Flowers having a vivid red color in the manner of carnations and geraniums contain a large amount of pelargonidin-based anthocyanins, while flowers having a blue or violet color contain a large amount of delphinidin-based anthocyanins. The reason for the absence of blue or violet varieties of roses, carnations, chrysanthemums and lilies is because these plants do not have the ability to synthesize delphinidin-based anthocyanins.

In addition to the accumulation of delphinidin, any of (i) the modification of anthocyanin by one or a plurality of aromatic acyl groups, (ii) the presence of a co-pigment such as flavone or flavonol together with anthocyanin, (iii) the presence of iron ions or aluminum ions together with anthocyanin, (iv) a rise in the pH of vacuoles where anthocyanin is localized from neutral to weakly alkaline, or (v) the formation of a complex by anthocyanin, co-pigment and metal ions (and this type of anthocyanin is referred to as metalloanthocyanin) is thought to be required in order for flower color to become blue (see Non-Patent Document 1).

Considerable research has been conducted on flavonoid and anthocyanin biosynthesis, and related biosynthetic enzymes and genes encoding those enzymes have been identified (see Non-Patent Document 2 and FIG. 1). For example, the gene of flavonoid 3',5'-hydroxylase (F3'5'H), which hydroxylates the B ring of flavonoids required for the biosynthesis of delphinidin, is obtained from numerous plants. In addition, transgenic plants that accumulate delphinidin in the petals thereof causing flower color to change to blue have been produced (see Non-Patent Document 4) by introducing these F3'5'H genes into carnations (see Patent Document 1), roses (see Non-Patent Document 3 and Patent Documents 2 and 3) and chrysanthemums (see Patent Document 4). Such carnations and roses are available commercially.

Flavone is a type of organic compound that is a cyclic ketone of a flavane derivative, and in the narrow sense, refers to the compound 2,3-dehydroflavan-4-one represented by the chemical formula $C_{15}H_{10}O_2$ and having a molecular weight of 222.24. In the broad sense, derivatives classified as flavones are generically referred to as "flavones". Flavone in the broad sense (flavones) refers to a category of flavonoids that are classified as having a flavone structure for the basic skeleton but not having a hydroxyl group at the 3-position. Examples of typical flavones include apigenin (4',5,7-trihydroxyflavone and luteolin (3',4',5,7-tetrahydroxyflavone). In the description of the present application, the term "flavone" refers to flavones in the broad sense, namely derivatives classified as flavones.

Genes of flavone synthases (FNS) required for biosynthesis of flavone are obtained from numerous plants. Flavones are known to have the effect of changing the color of anthocyanins to a deep blue color when present with anthocyanins, and these FNS genes have attracted attention in the modification of flower color. Simultaneous to the accumulation of delphinidin in flower petals, flavones were also accumulated and flower color changed to an even deeper blue color as a result of introducing F3'5'H and FNS gene into roses not having the ability to synthesize flavones (see Patent Document 5). In addition, since flavones also absorb ultraviolet rays in addition to causing flower color to become blue, they protect plants from ultraviolet rays or function as a visual signal to insects in the case of insect-pollinated flowers. In addition, flavones are also involved in the interaction between plants and soil microbes. Moreover, flavones are also used as an ingredient of foods and cosmetics as components beneficial to health. For example, flavones are said to have anticancer activity, and the ingestion of foods containing large amounts of flavones has been demonstrated to treat and prevent cancer.

In addition, genes that modify anthocyanins and flavones have also been obtained from numerous plants. Although these include glycosyltransferases, acyltransferases and methyltransferases, the following provides a description of glycosyltransferases (GT) that catalyze glycosylation reactions. For example, a gene encoding a protein having activity that transfers glucose to the hydroxyl group at the 3-position of anthocyanin has been isolated from plants such as gentian, perilla, petunia, rose and snapdragon (see Non-Patent Documents 4 to 6 and Patent Document 6). A gene encoding a protein having activity that transfers glucose to the hydroxyl group at the 5-position of anthocyanin has been isolated from such plants as perilla, petunia, gentian, verbena or torenia (see Non-Patent Documents 5 to 7 and Patent Document 7). A gene encoding a protein having activity that transfers glucose to the hydroxyl group at the 7-position of a flavone has been isolated from thale cress (see Non-Patent Document 8). A gene encoding a protein having activity that transfers glucose to the hydroxyl group at the 7-position of baicalein has been isolated from Baikal skullcap, and protein expressed by this gene in *Escherichia coli* has been reported to catalyze a reaction demonstrating activity that transfers glucose to the hydroxyl group at the 7-position of flavonoids (see Non-Patent Document 9). A gene encoding a protein having activity that transfers glucose to the hydroxyl group at the 3'-position of anthocyanin has been isolated from gentian, butterfly pea and cineria (see Patent Document 8). In addition, a gene encoding a protein having activity that successively transfers glucose to hydroxyl groups at two different locations of the A ring and C ring of anthocyanin has been isolated from rose (see Patent Document 9). A gene encoding a protein having activity that successively transfers glucose to hydroxyl groups at two different locations of the B ring of anthocyanin has been isolated from butterfly pea (see Patent Document 10).

Although the aforementioned glycosyltransferases use UDP-glucose as a sugar donor, glycosyltranferases have recently been identified that use acyl-glucose as a sugar donor. A gene encoding a protein having activity that transfers glucose to the hydroxyl group at the 5-position of anthocyanin 3-glucoside has been isolated from carnation, while a gene encoding a protein having activity that transfers glucose to the hydroxyl group at the 7-position has been isolated from delphinium (see Non-Patent Document 10).

In this manner, a large number of proteins exist as glycosyltransferases having activity that transfers glucose to various hydroxyl groups.

However, a large number of glycosyltransferases are thought to remain for which the function thereof has yet to be identified. For example, a gene encoding a protein having activity that transfers a sugar to the 4'-position of a flavonoid, and a gene encoding a protein having activity that successively transfers a sugar to hydroxyl groups at two locations of the A ring and B ring of a flavonoid have yet to be identified. Although a glycosyltransferase gene derived from Livingstone daisy has been reported to demonstrate activity that transfers glucose to one of the hydroxyl groups at the 4'-position or 7-position of a flavonoid in vitro, the inherent activity of this glycosyltransferase in plants transfers glucose to the hydroxyl group at the 5-position of betanidine (see Non-Patent Document 11).

However, metalloanthocyanins represented by the pigments of dayflower, cornflower, salvia and *nemophila* are composed of six anthocyanin molecules, six flavone molecules and two metal ion atoms, and each component is assembled to form a stable blue pigment (see FIG. 2 and Non-Patent Document 1). For example, the metalloanthocyanin of *nemophila* is formed from nemophilin (see FIG. 3), malonyl apigenin 4',7'-diglucoside (see FIG. 4), $Mg^{2+}$ and $Fe^{3+}$. Salvia metalloanthocyanin is formed from cyanosalvianin (see FIG. 5), apigenin 4,7'-diglucoside (see FIG. 6) and $Mg^{2+}$. According to previous research, all blue flowers that form metalloanthocyanins biosynthesize a flavone in which a sugar is added to the hydroxyl groups at both the 4'-position and 7-position, and the sugar added to that flavone has been determined to play an important role in molecular recognition during metalloanthocyanin formation. The sugar coordinated at the 4'-position of a flavone is important in molecular recognition during formation, while the sugar at the 7-position has been indicated to be involved in the stability thereof (see Non-Patent Document 1). Only after these two sugars have been added to a flavone is a metalloanthocyanin formed which results in the expression of an attractive blue color. In addition, the petals of blue Dutch iris contain a flavone in which a sugar has been added to the 4'-position. In addition, since solubility increases and physical properties change as a result of adding two sugars to flavones, their applications to health foods, pharmaceuticals and cosmetic ingredients are expected to expand.

PRIOR ART DOCUMENTS

Patent Documents

Patent Document 1: International Publication No. WO 2006/105598
Patent Document 2: International Publication No. WO 2010/122849
Patent Document 3: International Publication No. WO 2005/017147
Patent Document 4: International Publication No. WO 2009/062253
Patent Document 5: International Publication No. WO 2008/156211
Patent Document 6: International Publication No. WO 2007/094521
Patent Document 7: International Publication No. WO 99/05287
Patent Document 8: International Publication No. WO 001/092509
Patent Document 9: Japanese Unexamined Patent Publication No. 2006-149293
Patent Document 10: Japanese Unexamined Patent Publication No. 2005-95005

Non-Patent Documents

Non-Patent Document 1: Natural Product Reports (2009), 26, 884-915
Non-Patent Document 2: Biosci. Biotechnol. Biochem. (2010), 74(9), 1760-1769
Non-Patent Document 3: Plant Cell Physiol. (2007), 48(11), 1589-1600
Non-Patent Document 4: Plant Cell Physiol. (1996), 37(5), 711-716
Non-Patent Document 5: J. Biol. Chem. (1999), 274(11), 7405-7411
Non-Patent Document 6: Plant Molecular Biology (2002), 48, 401-411
Non-Patent Document 7: Journal of Experimental Botany (2008), 59(6), 1241-1252
Non-Patent Document 8: Biosci. Biotechnol. Biochem. (2006), 70(6), 1471-1477
Non-Patent Document 9: Planta (2010), 210, 1006-1013
Non-Patent Document 10: Plant Cell (2010), 22(10), 3374-89
Non-Patent Document 11: The Plant Journal (1999), 19(5), 509-519

DISCLOSURE OF THE INVENTION

Problems to be Solved by the Invention

Alteration of the physical properties of flavones is required to change flower color and develop materials for foods, pharmaceuticals and cosmetics. For example, although carnations, roses and chrysanthemums that accumulate delphinidin have a bluish-violet color, research is being conducted to make this color even bluer.

With the foregoing in view, an object of the present invention is to provide a polynucleotide that encodes a protein having activity that transfers a sugar to the hydroxyl group at the 4'-position of a flavone, and the use thereof.

Means for Solving the Problems

As a result of conducting extensive research and experimentation to solve the aforementioned problems, the present applicants isolated a polynucleotide that encodes a protein having activity that transfers a sugar to the hydroxyl group at the 4'-position of a flavone and confirmed the use thereof, thereby leading to completion of the present invention.

Namely, the present invention is as described below.

[1] A polynucleotide selected from the group consisting of the following (a) to (e):

(a) a polynucleotide composed of the base sequence of SEQ ID NO: 1;

(b) a polynucleotide that hybridizes under stringent conditions with a polynucleotide composed of a base sequence complementary to the base sequence of SEQ ID NO: 1, and encodes a protein having activity that transfers a sugar to the hydroxyl group at the 4'-position of a flavone;

(c) a polynucleotide encoding a protein composed of the amino acid sequence of SEQ ID NO: 2;

(d) a polynucleotide encoding a protein composed of an amino acid sequence in which one or a plurality of amino acids have been deleted, substituted, inserted and/or added in the amino acid sequence of SEQ ID NO: 2, and having activity that transfers a sugar to the hydroxyl group at the 4'-position of a flavone; and, (e) a polynucleotide encoding a protein having an amino acid sequence having identity of 90% or more with the amino acid sequence of SEQ ID NO: 2, and having activity that transfers a sugar to the hydroxyl group at the 4'-position of a flavone.

[2] The polynucleotide described in [1] above, which is (a) a polynucleotide composed of the base sequence of SEQ ID NO: 1.

[3] The polynucleotide described in [1] above, which is (c) a polynucleotide encoding a protein composed of the amino acid sequence of SEQ ID NO: 2.

[4] The polynucleotide described in [1] above, which is (f) a polynucleotide encoding a protein having an amino acid sequence having identity of 95% or more with the amino acid sequence of SEQ ID NO: 2, and having activity that transfers a sugar to the hydroxyl group at the 4'-position of a flavone.

[5] The polynucleotide described in [4] above, which is (g) a polynucleotide encoding a protein having an amino acid sequence having identity of 97% or more with the amino acid sequence of SEQ ID NO: 2, and having activity that transfers a sugar to the hydroxyl group at the 4'-position of a flavone.

[6] The polynucleotide described in [5] above, which is (h) a polynucleotide encoding a protein having an amino acid sequence having identity of 98% or more with the amino acid sequence of SEQ ID NO: 2, and having activity that transfers a sugar to the hydroxyl group at the 4'-position of a flavone.

[7] The polynucleotide described in any of [1] to [6] above, which is DNA.

[8] A protein encoded by the polynucleotide described in any of [1] to [7] above.

[9] A vector containing the polynucleotide described in any of [1] to [7] above.

[10] A non-human host introduced with the vector described in [9] above.

[11] A method for adding a sugar to the hydroxyl group at the 4'-position of a flavone using the polynucleotide described in any of [1] to [7] above.

[12] A plant, a progeny thereof, or a portion or tissue thereof, introduced with the polynucleotide described in any of [1] to [7] above and containing that polynucleotide.

[13] A portion of the plant described in [12] above that is a cut flower.

[14] A processed cut flower that uses the cut flower described in [13] above.

[15] A method for producing a protein having activity that transfers a sugar to the hydroxyl group at the 4'-position of a flavone, comprising the following steps:

culturing or growing the non-human host described in [10] above, and harvesting protein from the non-human host that has activity that transfers a sugar to the hydroxyl group at the 4'-position of a flavone.

[16] A method for producing a flavone in which a sugar has been added to the hydroxyl group at the 4'-position thereof, comprising the following steps:

culturing or growing the non-human host described in [10] above, and harvesting a flavone from the non-human host in which a sugar has been added to the hydroxyl group at the 4'-position thereof.

[17] A food containing a flavone produced according to the production method described in [16] above in which a sugar has been added to the hydroxyl group at the 4'-position thereof.

[18] A pharmaceutical containing a flavone produced according to the production method described in [16] above in which a sugar has been added to the hydroxyl group at the 4'-position thereof.

[19] A cosmetic containing a flavone produced according to the production method described in [16] above in which a sugar has been added to the hydroxyl group at the 4'-position thereof.

Effects of the Invention

The polynucleotide of the present invention enables the production of a protein having activity that specifically transfers a sugar to the hydroxyl group at the 4'-position of a flavone as a result of being expressed in suitable host cells. According to the present invention, the present invention can be used to alter flower color by constitutively or tissue-specifically expressing in a plant a protein having activity that transfers a sugar to the hydroxyl group at the 4'-position of a flavone.

A flavone in which a sugar has been added to both of the hydroxyl groups at the 4'-position and 7-position is formed by introducing a protein having activity that transfers a sugar to the hydroxyl group at the 4'-position of a flavone into a plant inherently having activity that transfers a sugar to the hydroxyl group at the 7-position of a flavone in the manner of rose, for example. Alternatively, a flavone in which a sugar has been added to both of the hydroxyl groups at the 4'-position and 7-position is formed by expressing in a plant a protein having activity that transfers a sugar to the hydroxyl group at the 4'-position of a flavone together with a protein having activity that transfers a sugar to the hydroxyl group at the 7-position of a flavone.

In addition, according to the present invention, a method for producing a flavone in which a sugar has been added to the hydroxyl group at the 4'position, and a food, pharmaceutical or cosmetic and the like obtained according to that production method, are also provided.

FIG, 10 is a high-performance liquid chromatogram obtained follo ring an enzyme reaction between NmGT8 protein solution and apigenin 7-glucoside.

FIG. 11 is a drawing summarizing the reactivities of NnGT8 protein solution and enzyme in which a sugar has been added to the 5-position of baicalein on various flavonoid substrates.

Figure 1:
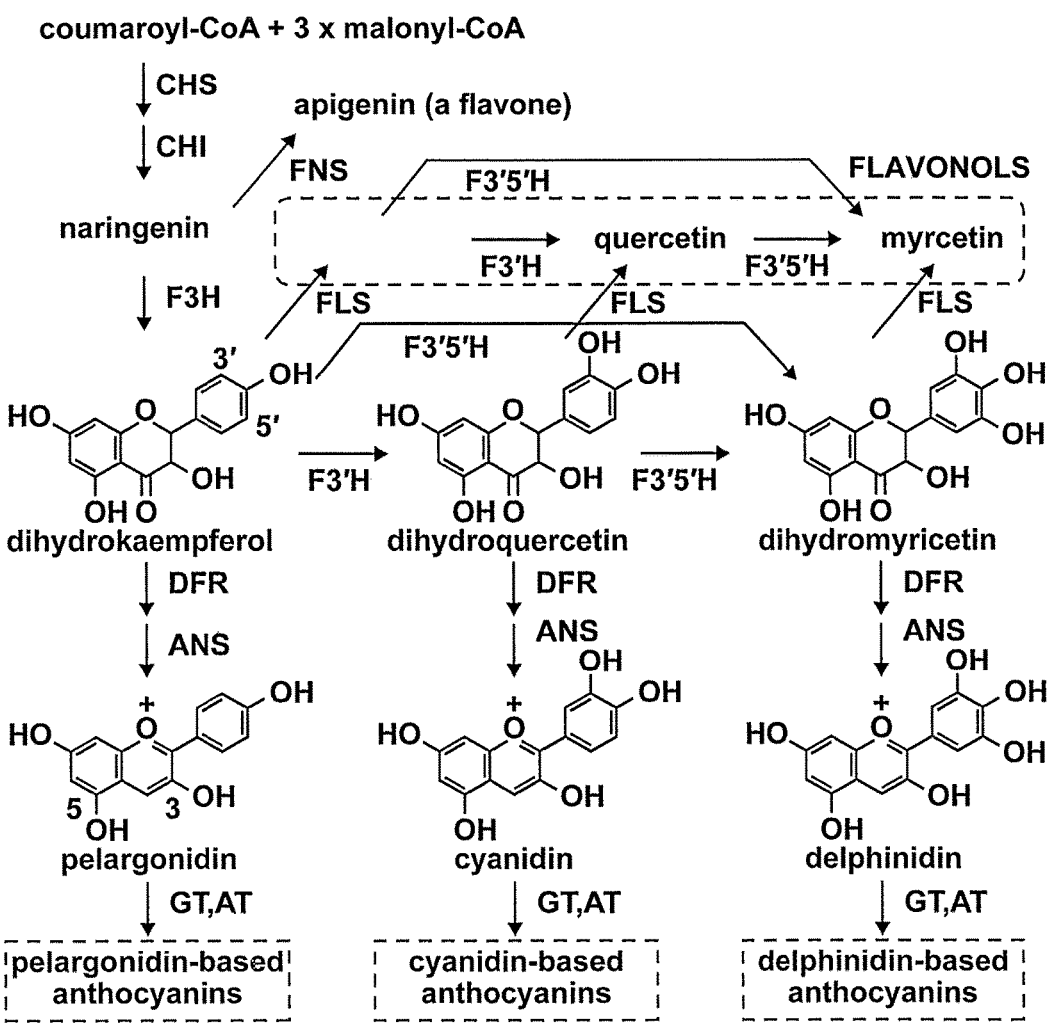
FIG. 1 is a drawing for explaining the biosynthesis pathway of anthocyanins. FIG, 2 is a schematic diagram of the structure of metalloanthocyanin.

FIG. 12-1 is an alignment diagram comparing the amino acid sequences of NmGT8_ (SEQ ID NO: 2) and NmG13 (SEQ ID NO: 11).

Figure 2:
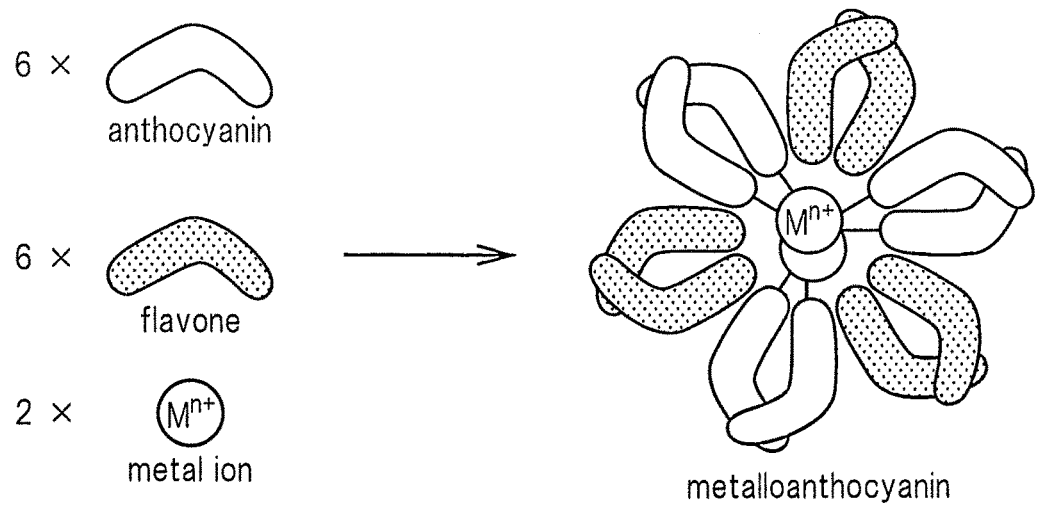

FIG. 12-2 is an alignment diagram comparing the amino acid sequences of NmGT8_ (SEQ ID NO: 2) and NmGT4 (SEQ ID NO: 13).

Figure 3:
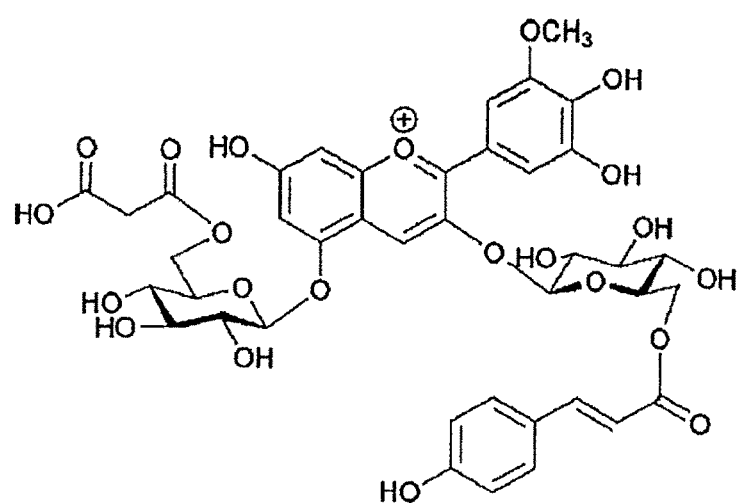
FIG. 3 shows the structural formula of a *nemophila*-derived anthocyanin (nemophilin).
Figure 4:
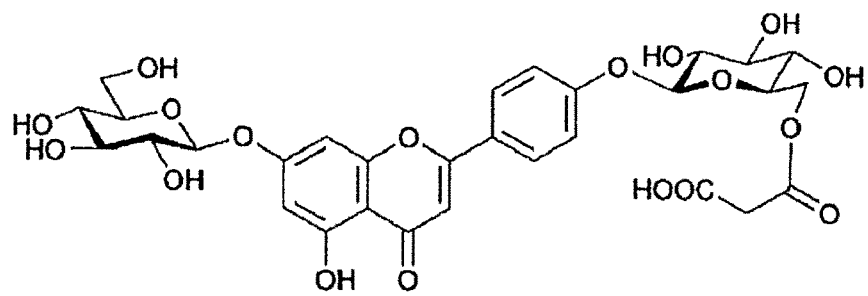
FIG. 4 shows the structural formula of a *nemophila*-derived flavone (malonyl apigenin 4',7'-diglucoside).
Figure 5:
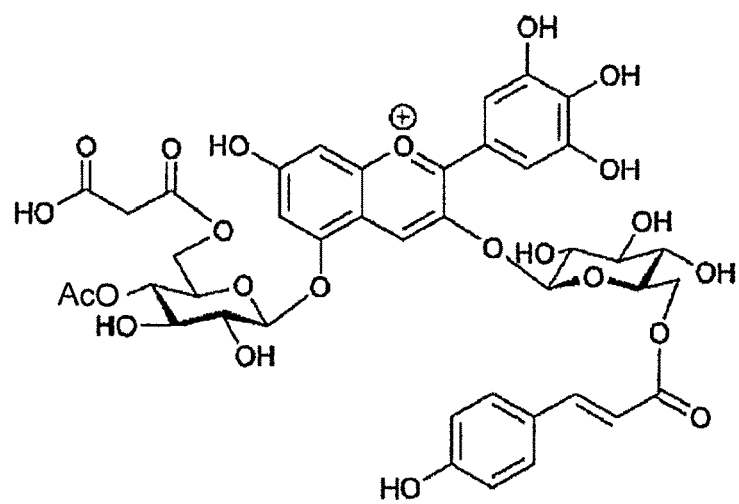
FIG. 5 shows the structural formula of salvia-derived flavone (cyanosalvianin).
Figure 6:
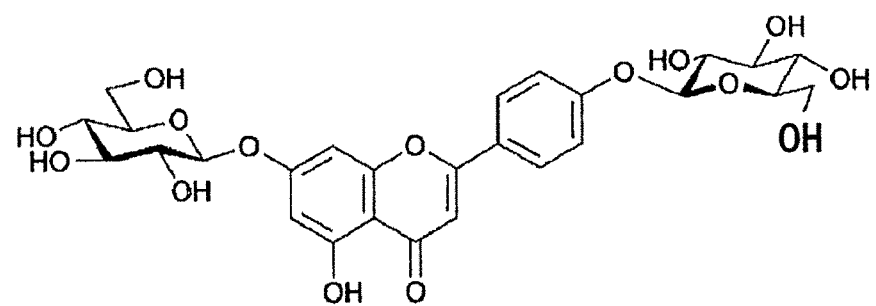
FIG. 6 shows the structural formula of a salvia-derived flavone (apigenin 4',7-diglucoside).

FIG. 12-3 is an alignment diagram comparing the amino acid sequences of NmGT8_ (SEQ ID NO: 2), NmGT3 (SEQ ID NO: 11) and NmGT4 (SEQ ID NO: 13).

FIG. 13 is an alignment diagram comparing the amino acid sequences of NmGT8 (SEQ ID NO: 2) and an enzyme in which a sugar has been added to the 4'-position of snapdragon chalcone (SEQ ID NO: 14).

Figure 15:
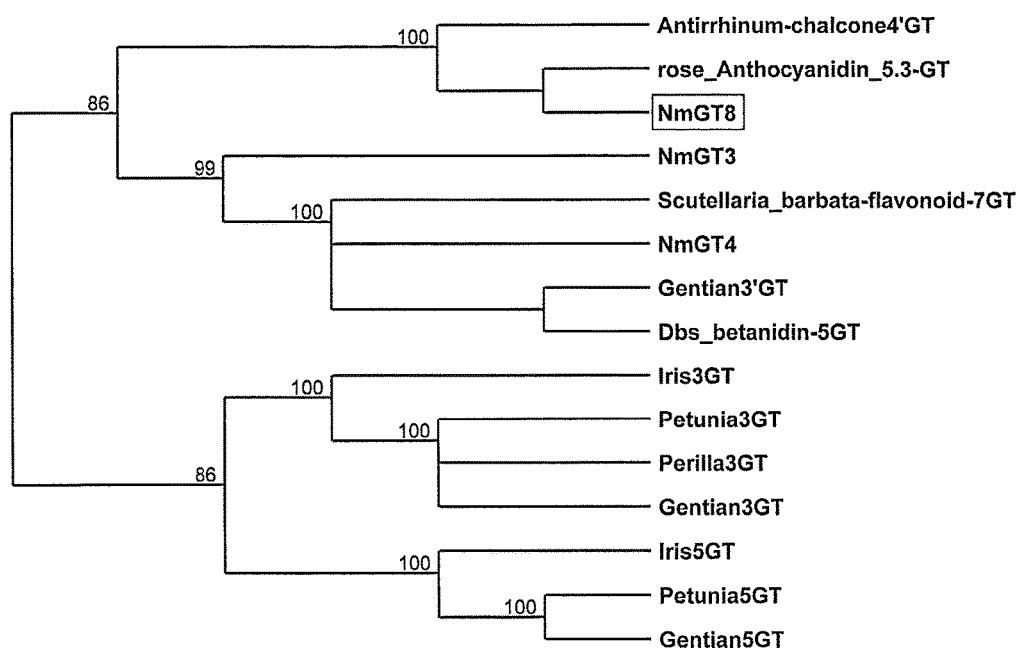

FIG. 14 is an alignment diagram comparing the amino acid sequences of NmGT8 (SEQ ID NO: 2) and an enzyme in which sugars have been added to the 3-position and 5-position of rose anthocyanidin (SEQ ID NO: 15), FIG. 15 is a phylogenetic tree indicating the relationships between the NmGT8of the present invention and the aforementioned enzymes.

Figure 16:
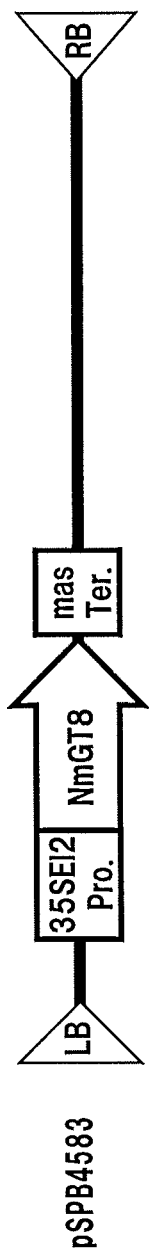

FIG. 16 shows a construct containing NmGT8 introduced into torenia (pSPB4583).

Figure 17:
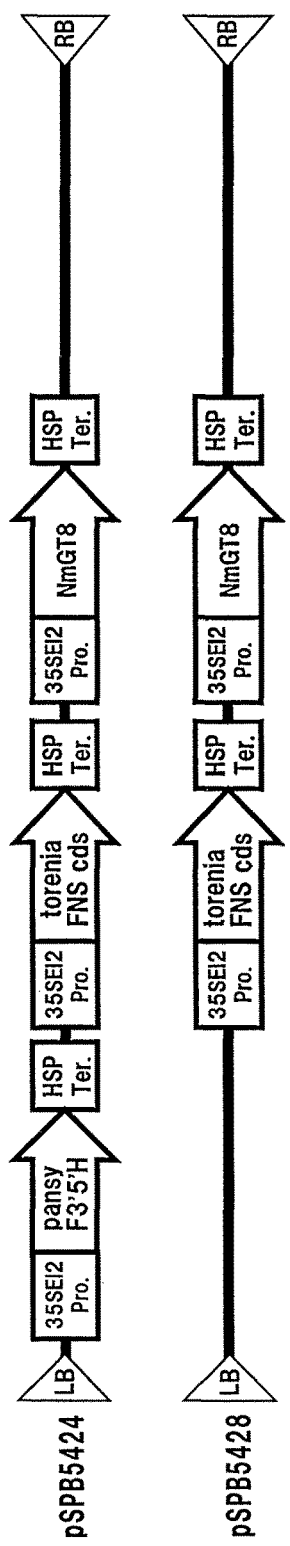

FIG. 17 shows constructs containing NmGT8 introduced into petunia (pSPB5424 and pSPB5428).

Figure 18:
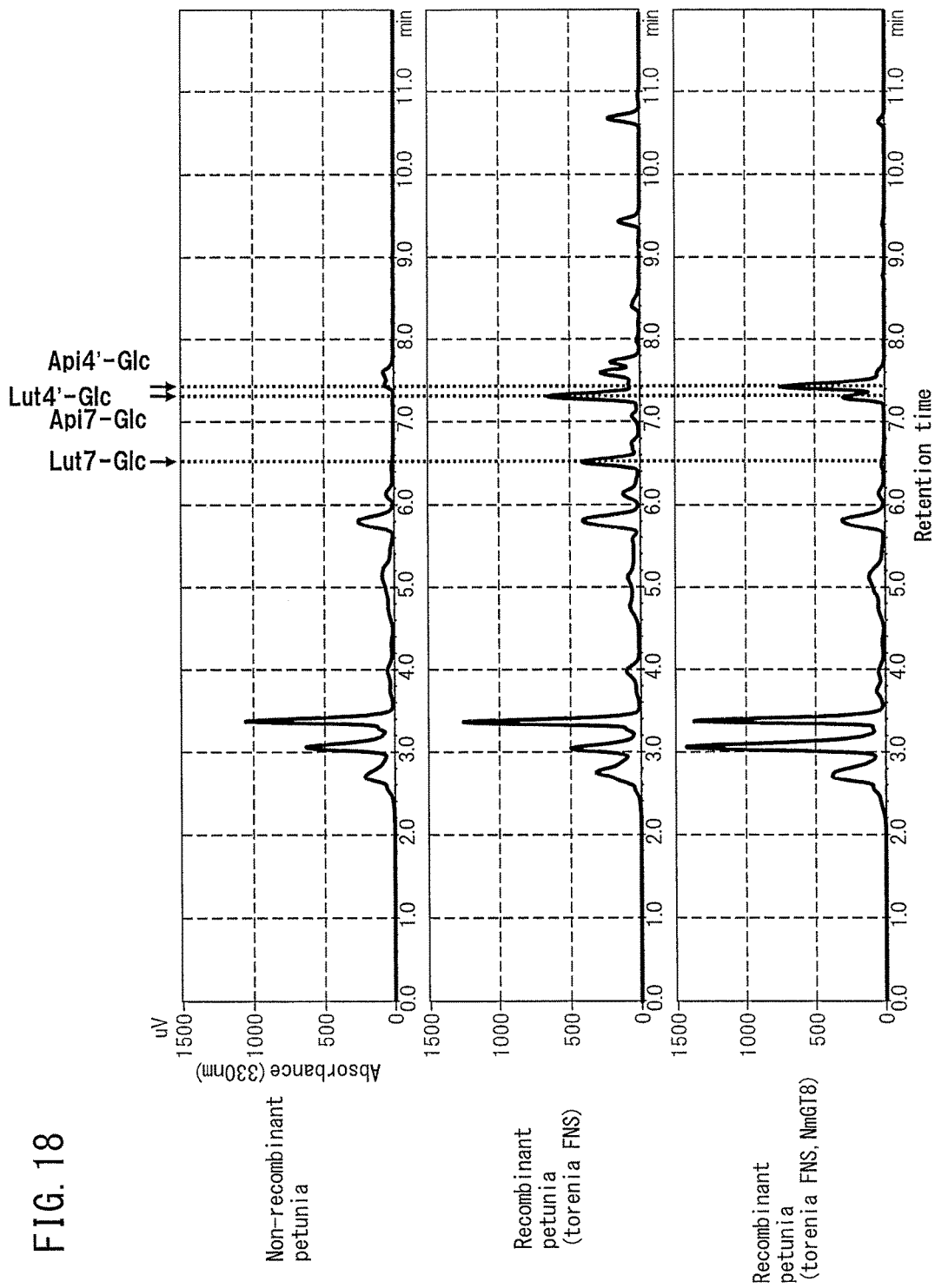

FIG. 18 is a high-performance liquid chromatogram of a flower petal extract of recombinant petunia introduced with NmGT8.

Figure 19:
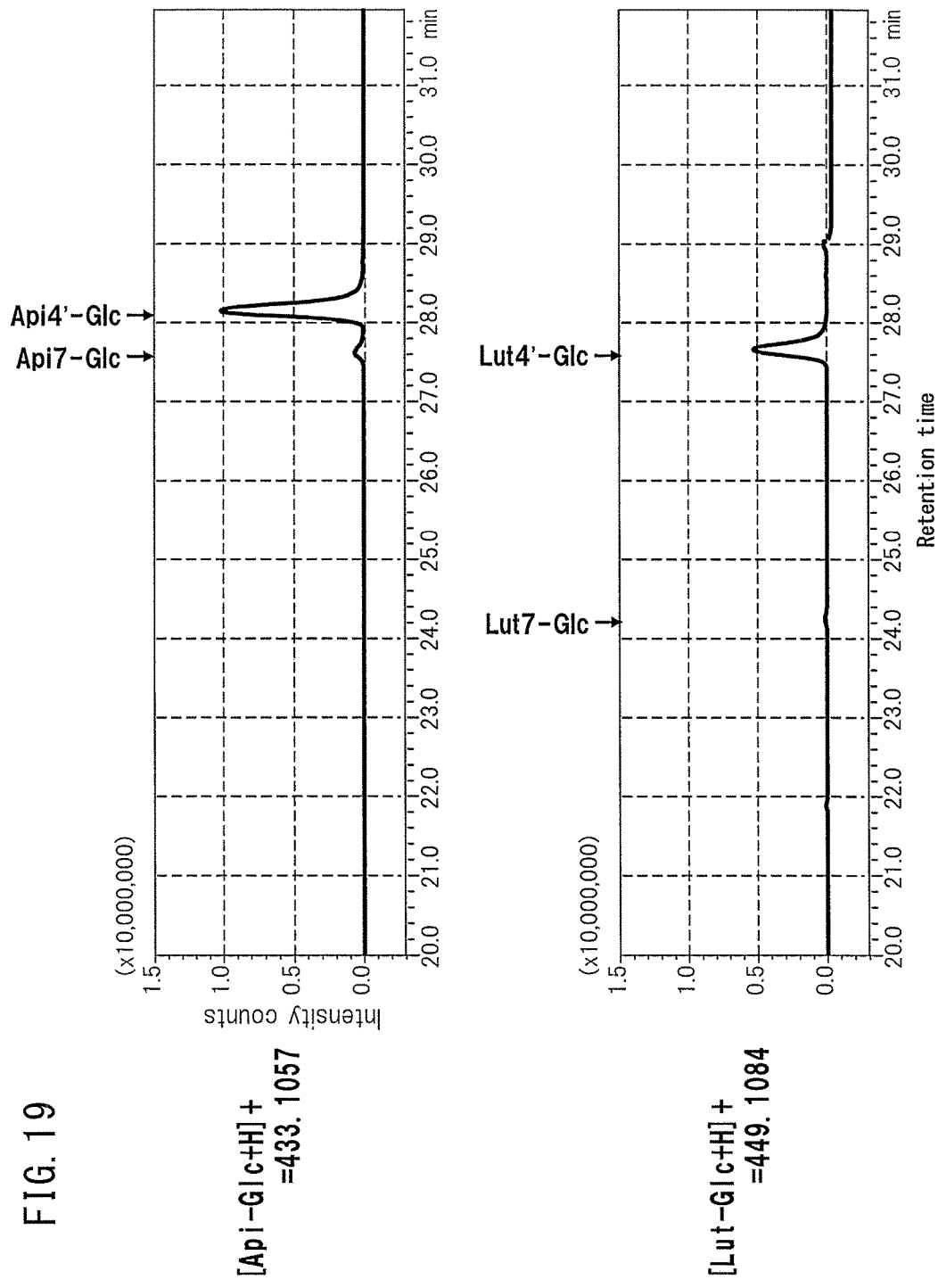

FIG. 19 is an extracted positive ion gas chromatogram of a flower petal extract (250 m/z to 1250 m/z) of recombinant petunia introduced with NmGT8.

Figure 20:
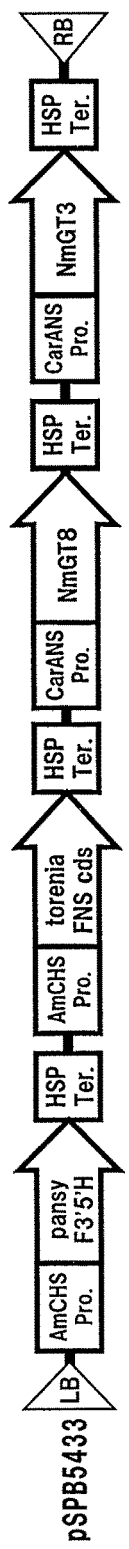
Figure 21:
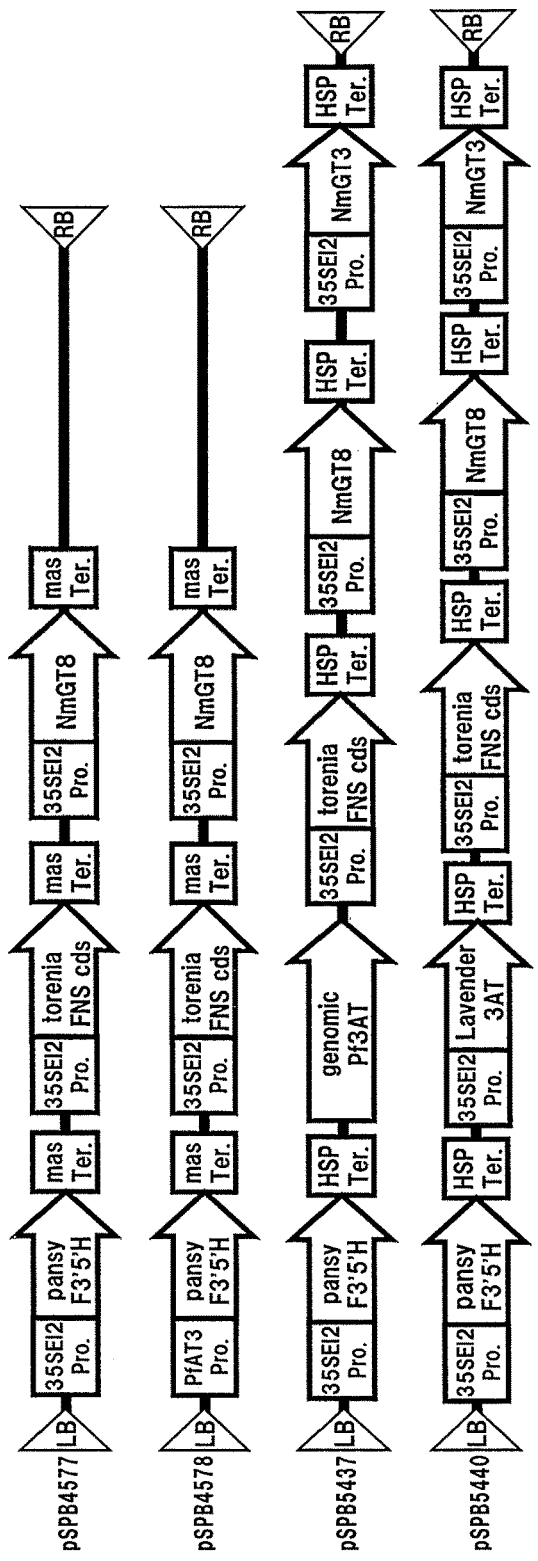

FIG. 20 shows a construct containing NmGT8 introduced into carnation (pSPB5433). FIG. 21 shows constructs containing NmGT8 introduced into rose (pSPB4577, pSPB4578, pSPB5437 and pSPB5440).

Figure 22:
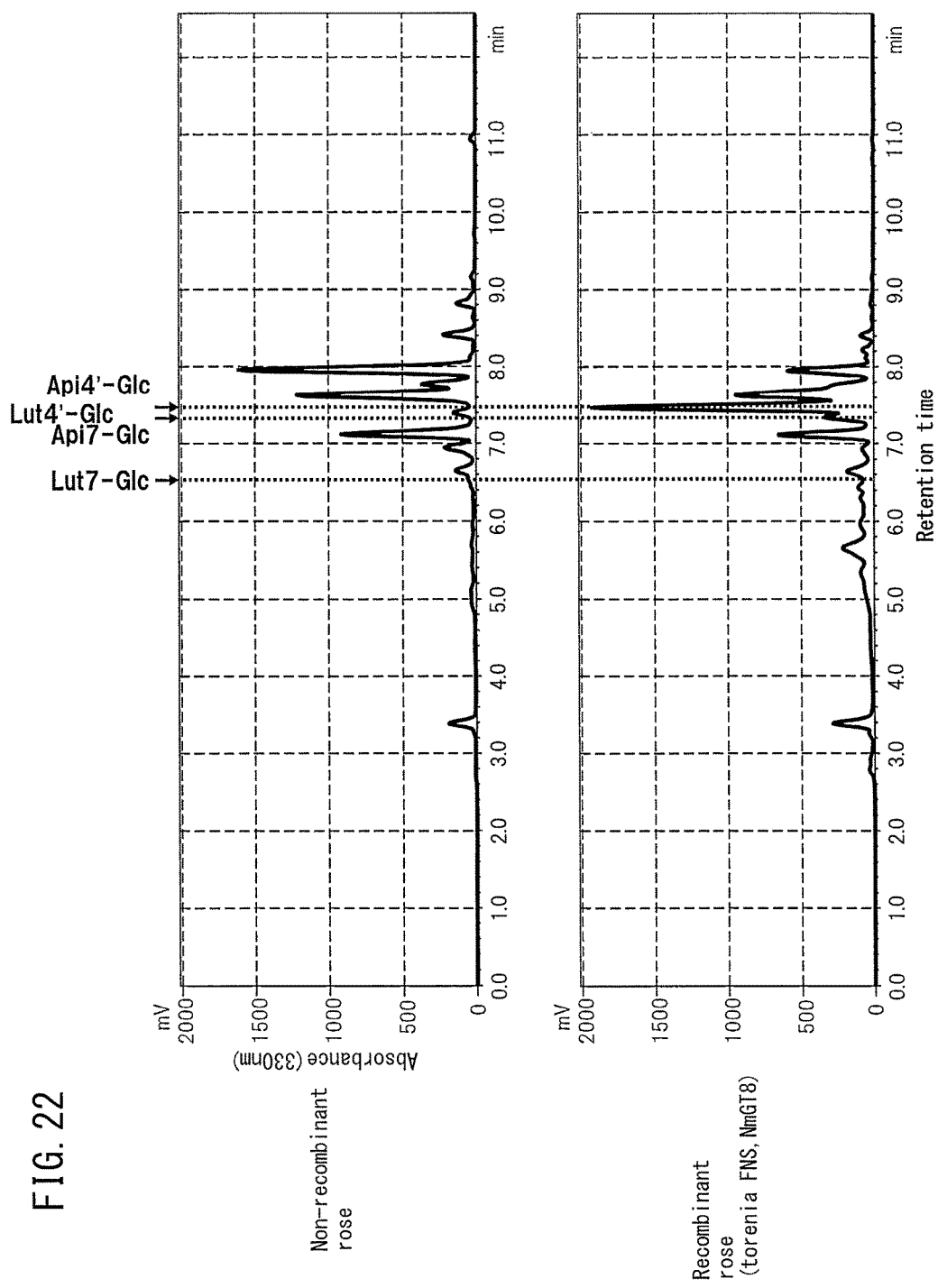

FIG. 22 is a high-performance liquid chromatogram of a flower petal extract of recombinant rose introduced with NmGT8.

FIG, 23 is an extracted positive ion mass chromatogram of a flower petal extract (250 m/z to 1250 m/z) of recombinant rose introduced with NmGT8.

BEST MODE FOR CARRYING OUT THE INVENTION

The present invention relates to a polynucleotide selected from the group consisting of the following (a) to (e):

(a) a polynucleotide composed of the base sequence of SEQ ID NO: 1;

(b) a polynucleotide that hybridizes under stringent conditions with a polynucleotide composed of a base sequence complementary to the base sequence of SEQ ID NO: 1, and encodes a protein having activity that transfers a sugar to the hydroxyl group at the 4'-position of a flavone;

(c) a polynucleotide encoding a protein composed of the amino acid sequence of SEQ ID NO: 2;

(d) a polynucleotide encoding a protein composed of an amino acid sequence in which one or a plurality of amino acids have been deleted, substituted, inserted and/or added in the amino acid sequence of SEQ ID NO: 2, and having activity that transfers a sugar to the hydroxyl group at the 4'-position of a flavone; and, (e) a polynucleotide encoding a protein having an amino acid sequence having identity of 90% or more with the amino acid sequence of SEQ ID NO: 2 and having activity that transfers a sugar to the hydroxyl group at the 4'-position of a flavone.

In the present description, the term "polynucleotide" refers to DNA or RNA.

In the present description, the term "stringent conditions" refers to conditions under which a polynucleotide or oligonucleotide and genomic DNA bind selectively and specifically so as to be able to be detected. Stringent conditions are defined by a suitable combination of salt concentration, organic solvent (such as formaldehyde) concentration, temperature and other known conditions. Namely, stringency is increased by reducing salt concentration, increasing organic solvent concentration or raising hybridization temperature. Moreover, washing conditions following hybridization also influence stringency. These washing conditions are also defined by salt concentration and temperature, and washing stringency increases by reducing salt concentration or raising temperature. Thus, the term "stringent conditions" refers to conditions under which specific hybridization occurs only between base sequences having high homology such that the degree of identity or homology between each base sequence is, for example, an average of about 80% or more, preferably about 90% or more, more preferably about 95% or more, even more preferably about 97% or more, and most preferably 98% or more. An example of "stringent conditions" consists of a sodium concentration of 150 mM to 900 mM, and preferably 600 mM to 900 mM and pH of 6 to 8 at a temperature of 60° C. to 68° C., and more specifically, consists of carrying out hybridization under conditions consisting of 5×SSC (750 mM NaCl, 75 mM trisodium citrate), 1% SDS, 5× Denhardt's solution, 50% formaldehyde and 42° C., followed by washing under conditions consisting of 0.1×SSC (15 mM NaCl, 1.5 mM trisodium citrate), 0.1% SDS and 55° C.

Hybridization can be carried out in accordance with a method known in the art or a method complying therewith, such as the method described in Current Protocols in Molecular Biology (edited by Frederick M. Ausubel, et al., 1987). In addition, in the case of using a commercially available library, hybridization can be carried out in accordance with the method described in the manual provided therewith. Genes selected using such hybridization may be naturally-derived genes such as those derived from plants or those not derived from plants. In addition, genes selected by hybridization may be cDNA, genomic DNA or chemically synthesized DNA.

The aforementioned "amino acid sequence in which one or a plurality of amino acids have been deleted, substituted, inserted and/or added" refers to an amino acid sequence in which an arbitrary number of amino acids, such as 1 to 20, preferably 1 to 5 and even more preferably 1 to 3, have been deleted, substituted, inserted and/or added. A genetic engineering technique in the form of site-specific mutagenesis is useful since it allows the introduction of a specific mutation at a specific site, and can be carried out in compliance with a method such as that described in Molecular Cloning: A Laboratory Manual, 2nd ed., Cold Spring Harbor Laboratory Press, Cold Spring Harbor, N.Y., 1989. By expressing this mutant DNA using a suitable expression system, a protein can be obtained that is composed of an amino acid sequence in which one or a plurality of amino acids have been deleted, substituted, inserted and/or added.

In addition, the DNA according to the present invention can be obtained by a method known among persons with ordinary skill in the art, such as a method consisting of chemical synthesis according to the phosphoamide method, or a nucleic acid amplification method using a nucleic acid sample from a plant as template and using primers designed based on the nucleotide sequence of a target gene.

In the present description, the terms "identity" and "homology" refer to a quantity (number) that makes it possible to determine that corresponding amino acid residues or bases composing two chains in a polypeptide sequence (or amino acid sequence) or polynucleotide sequence (or base sequence) are identical in terms of the relationship of mutual compatibility between the two chains, and "identity" and "homology" can easily be calculated. Numerous methods are known for measuring homology between two polynucleotide sequences or polypeptide sequences, and the terms "identity" and "homology" are widely known among persons with ordinary skill in the art (see, for example, Lesk, A. M. (ed.), Computational Molecular Biology, Oxford University Press, New York (1988); Smith, D. W. (ed.), Biocomputing: Informatics and Genome Projects, Academic Press, New York (1993); Grifin, A. M. & Grifin, H. G. (ed.), Computer Analysis of Sequence Data: Part I, Human Press, New Jersey (1994); von Heinje, G., Sequence Analysis in Molecular Biology, Academic Press, New York (1987); and Gribskov, M. & Devereux, J. (ed.), Sequence Analysis Primer, M-Stockton Press, New York (1991)).

In addition, although the values of "identity" and "homology" described in the present description may be values calculated using a homology search program known among persons with ordinary skill in the art unless specifically indicated otherwise, they are preferably values calculated using the Clustal W Program of the MacVector Application (Version 9.5, Oxford Molecular Ltd., Oxford, England).

The polynucleotide (nucleic acid or gene) of the present invention is that which "encodes" a protein of interest. Here, "encodes" refers to expressing a protein of interest in a state of retaining the activity thereof. In addition, "encodes" includes both the meaning of encoding in the form of a constituent sequence (exon) in which the protein of interest is contiguous, and encoding through an intermediary sequence (intron).

As will be described in the examples to be subsequently described, a gene having a naturally-occurring base sequence is obtained by, for example, analysis with a DNA sequencer. In addition, DNA encoding an enzyme having a modified amino acid sequence can be synthesized using ordinary site-specific mutagenesis or PCR using DNA having a naturally-occurring sequence as a base. For example, after obtaining a DNA fragment desired to be modified by treatment with cDNA or genomic DNA restrictase, site-specific mutagenesis or PCR is carried out using the DNA fragment as a template and using primers introduced with a desired mutation to obtain a desired modified DNA fragment. Subsequently, the DNA fragment introduced with this mutation is linked to a DNA fragment encoding another segment of a target enzyme.

Alternatively, in order to obtain DNA encoding enzyme composed of a shortened amino acid sequence, DNA encoding an amino acid sequence longer than the target amino acid sequence, such as DNA encoding the full-length amino acid sequence, is cleaved with a restrictase, and in the case the resulting DNA fragment does not encode the entire target amino acid sequence, a DNA fragment composed of the insufficient portion of the sequence is synthesized and linked thereto.

In addition, by measuring enzyme activity after expressing the resulting polynucleotide in Escherichia coli or yeast using a gene expression system, the resulting polynucleotide can be confirmed to encode a protein having activity that transfers a sugar to the hydroxyl group at the 4'-position of a flavone. Moreover, the polynucleotide product in the form of a protein having activity that transfers a sugar to the hydroxyl group at the 4'-position of a flavone can be obtained by expressing this polynucleotide. Alternatively, a protein having activity that transfers a sugar to the hydroxyl group at the 4'-position of a flavone can also be acquired by using an antibody to a polypeptide composed of the amino acid sequence described in SEQ ID NO: 2, and a polynucleotide encoding a protein having activity that transfers a sugar to the hydroxyl group at the 4'-position of a flavone originating in another organism can also be cloned using this antibody.

The present invention also relates to a (recombinant) vector containing the aforementioned polynucleotide, and particularly an expression vector, as well as a host transformed by that vector.

Prokaryotes or eukaryotes can be used for the host. Examples of prokaryotes include commonly used prokaryotic hosts such as bacteria, including bacteria belonging to the genus *Escherichia* such as *Escherichia coli,* and bacteria belonging to the genus *Bacillus* such as *Bacillus subtilis.* Examples of eukaryotes that can be used include lower eukaryotes such as eukaryotic organisms in the manner of fungi such as yeast or filamentous fungi.

Examples of yeast include *Saccharomyces* species such as *Saccharomyces cerevisiae,* and examples of filamentous fungi include *Aspergillus* species, such as *Aspergillus oryzae* or *Aspergillus niger,* and *Penicillium* species. Animal cells or plant cells can also be used for the host, examples of animal cell systems used include mouse, hamster, monkey or human cells, and insect cells such as silkworm cells or silkworm adults per se are also used as hosts.

The expression vector of the present invention contains an expression regulatory region, such as a promoter, terminator or replication point, dependent on the type of host into which it is introduced. A commonly used promoter such as a trc promoter, a tac promoter or an lac promoter is used as a promoter of a bacterial expression vector, a glyceraldehyde-3-phosphate dehydrogenase promoter or a PH05 promoter, for example, is used as a yeast promoter, and an amylase promoter or trpC promoter, for example, is used as a filamentous fungi promoter. In addition, examples of promoters for animal cell hosts include viral promoters such as an SV40 early promoter or SV40 late promoter.

Examples of promoters that constitutively express polynucleotide in plant cells include cauliflower mosaic virus 35S RNA promoter, rd29A gene promoter, rbcS promoter and mac-1 promoter. In addition, a promoter of a gene that specifically expresses in that tissue can be used for tissue-specific gene expression.

An expression vector can be produced in accordance with ordinary methods using restrictases, ligases and the like. In addition, transformation of a host with an expression vector can also be carried out in accordance with ordinary methods.

A target protein can be obtained by culturing, cultivating or growing a host transformed by the aforementioned expression vector, and recovering and purifying from the culture or medium in accordance with ordinary methods such as filtration, centrifugal separation, cell disruption, gel filtration chromatography or ion exchange chromatography.

Although the present description describes a gene encoding a protein having activity that transfers a sugar to the hydroxyl group at the 4'-position of a flavone derived from *nemophila*, the polynucleotide according to the present invention is not limited to a gene derived from *nemophila*, but rather can be used to alter flower color in a plant regardless of whether the origin of the gene encoding a protein having activity that transfers a sugar to the hydroxyl group at the 4'-position of a flavone is a plant, animal or microorganism provided it has activity that transfers a sugar to the hydroxyl group at the 4'-position of a flavone.

The present invention also relates to a plant, a progeny thereof, or a portion or tissue thereof, obtained by introducing an exogenous polynucleotide encoding a protein having activity that transfers a sugar to the hydroxyl group at the 4'-position of a flavone, and causing that exogenous polynucleotide to be contained in the plant. An example of the form of the portion or tissue is a cut flower. The 4'-position of a flavone can be glycosylated or glycosylation of the 4'-position of a flavone can be inhibited by using the polynucleotide according to the present invention that encodes a protein having activity that transfers a sugar to the hydroxyl group at the 4'-position of a flavone, and flower color in a plant can be altered as a result thereof.

At the present level of technology, technology can be used that enables a polynucleotide to be introduced into a plant, and enables that polynucleotide to be expressed constitutively or tissue-specifically. Introduction of DNA into a plant can be carried out by a method known among persons with ordinary skill in the art, such as the *Agrobacterium* method, binary vector method, electroporation method, PEG method or particle gun method.

Examples of plants able to be transformed include, but are not limited to, rose, carnation, chrysanthemum, snapdragon, cyclamen, orchid, bluebell, freesia, Transvaal daisy, gladiola, baby's breath, kalanchoe, lily, pelargonium, geranium, petunia, torenia, tulip, arithurium, moth orchid, rice, barley, wheat, rape, potato, tomato, poplar, banana, eucalyptus, sweet potato, soybean, alfalfa, rubin basil, corn, cauliflower and dahlia.

The present invention also relates to a processed product using the aforementioned cut flower (processed cut flower).

Here, examples of processed cut flowers include, but are not limited to, pressed flowers, preserved flowers, dry flowers and resin-sealed flowers using these cut flowers.

In addition, a flavone produced according to the production method of the present invention in which a sugar has been added to the hydroxyl group at the 4'-position thereof can be used in applications such as the production methods of foods, pharmaceuticals or cosmetics.

In the present invention, expression of a target gene in a plant can be suppressed by an antisense method, co-suppression method or RNAi method. Although suppression of the expression of a target gene can be carried out in accordance with a method known among persons with ordinary skill in the art, examples thereof include the antisense RNA/DNA technique (Bioscience and Industry, 50, 322 (1992); Chemistry, 46, 681 (1991); Biotechnology, 9, 358 (1992); Trends in Biotechnology, 10, 152 (1992); Cellular Engineering, 16, 1463 (1997)), and the triple helix technique (Trends in Biotechnology, 10, 132 (1992)). For example, suppression of gene expression is carried out using a single-stranded nucleic acid molecule comprising all or a portion of a nucleotide sequence identical to the antisense strand of the gene according to the present invention. This type of method is known as the antisense method. In the antisense method, expression of a target gene is suppressed by expressing a high level of RNA having a sequence complementary to the gene for which expression is desired to be suppressed. In this method, single-stranded RNA can be used that comprises the entirety of a nucleotide sequence identical to the antisense strand of the polynucleotide (gene) according to the present invention. In addition, in the aforementioned method, single-stranded RNA can also be used that comprises a portion of a nucleotide sequence identical to the antisense strand of the gene according to the present invention. Although this type of partial single-stranded RNA can be suitably designed by a person with ordinary skill in the art provided it is able to suppress expression of the gene according to the present invention, it is preferably specific for the gene according to the present invention, and the length thereof is preferably 5 nucleotides to 100 nucleotides, more preferably 5 nucleotides to 50 nucleotides, and even more preferably 10 nucleotides to 20 nucleotides.

Suppression of gene expression is carried out using a single-stranded nucleic acid molecule comprising all or a portion of a nucleotide sequence identical to a sense strand of the gene according to the present invention. Namely, this sense single-stranded nucleic acid can be used to suppress expression of the gene according to the present invention in the same manner as the aforementioned antisense single-stranded nucleic acid. In this method, single-stranded RNA can be used that comprises the entirety of a nucleotide sequence identical to a sense strand of the gene according to the present invention. In addition, in the aforementioned method, single-stranded RNA can be used that comprises a portion of a nucleotide sequence identical to a sense strand of a gene. Although this type of partial single-stranded RNA can be suitably designed by a person with ordinary skill in the art provided it is able to suppress expression of the gene according to the present invention, it preferably specific for the gene according to the present invention, and the length thereof is preferably 5 nucleotides to 100 nucleotides, more preferably 5 nucleotides to 50 nucleotides and even more preferably 10 nucleotides to 20 nucleotides.

Moreover, suppression of gene expression is carried out using a double-stranded nucleic acid molecule comprising all or a portion of a nucleotide sequence identical to the gene according to the present invention. For example, an antisense or sense single-stranded nucleic acid of a gene according to the present invention can be suppressed in an angiosperm by using this double-stranded nucleic acid molecule. The double-stranded nucleic acid molecule according to the present invention is preferably DNA, and the strand length and specific nucleotide sequence thereof correspond to the strand length and nucleotide sequence of the target single-stranded nucleic acid molecule. For example, in the case of expressing the aforementioned antisense single-stranded nucleic acid, the double-stranded nucleic acid molecule according to the present invention contains an antisense strand of the gene according to the present invention as the coding strand. In addition, in the case of expressing the aforementioned sense single-stranded nucleic acid, the double-stranded nucleic acid according to the present invention contains a sense strand of the gene according to the present invention as the coding strand.

A double-stranded nucleic acid molecule can be expressed in a plant using a method known among persons with ordinary skill in the art. For example, a double-stranded nucleic acid molecule can be expressed by introducing an expression vector containing a promoter, the double-stranded nucleic acid molecule according to the present invention, and a transcription terminator into a target plant followed by cultivating the, resulting plant body. Introduction of the expression vector into the plant can be carried out according to a method known among persons with ordinary skill in the art, such as the *Agrobacterium* method, binary vector method, electroporation method, PEG method or particle gun method.

Another example of a method for suppressing gene expression using the nucleic acid molecule according to the present invention is the co-suppression method. In this method, sense double-stranded DNA having the complete nucleotide sequence of the gene according to the present invention is introduced into a target plant. As a result, sense single-stranded RNA according to the present invention is expressed, and gene expression is suppressed considerably by this RNA (Plant Cell, 9: 1357-1368, 1997).

EXAMPLES

The following provides a detailed explanation of the invention according to examples thereof.

Example 1

Detection of Activity that Transfers a Sugar to the Hydroxyl Group at the 4'-Position of Flavone in *Nemophila* Flower Petals Flower petals of nemophila (*Nemophila menziesii*) were collected by dividing into developmental stages defined in the manner indicated below followed by freezing with liquid nitrogen and storing in a freezer at −80° C.

Stage 1: Uncolored, tightly closed bud (approx. 2 to 5 mm)
Stage 2: Colored, tightly closed bud (approx. 2 to 5 mm)
Stage 3: Colored, closed bud with calyx about to open (approx. 5 to 10 mm)
Stage 4: Bud with flower petals about to open (approx. 10 to 15 mm)
Stage 5: Completely open flower <Preparation of *Nemophila* Flower Petal Extract>

Flavone glycosyltransferase activity is expected to be detected in flower petals in stage 1 and stage 2 prior to biosynthesis of anthocyanin. Therefore, flower petal extracts were prepared using flower petals in stages 1 and 2. 500 mg of sample flower petals (250 mg each of flower petals in stages 1 and 2 stored at −80° C.) were crushed with a mortar and pestle while cooling with liquid nitrogen followed by dissolving in 1.5 ml of extraction buffer (composition: potassium phosphate buffer (pH 7.5): 100 mM, dithiothreitol (DTT): 1 mM, polyvinylpyrrolidone 40: 50 mg/ml, sucrose: 100 mg/ml). The resulting protein solution was centrifuged (10,000 rpm, 4° C., 10 minutes), and ammonium sulfate was added to the resulting supernatant to a saturated concentration of 30%. After stirring for 1 hour at 4° C., the solution was centrifuged (10,000 rpm, 4° C., 10 minutes) followed by recovery of the supernatant. Ammonium sulfate was added to the resulting supernatant to a saturated concentration of 70%, and after stirring for 1 hour at 4° C., the solution was centrifuged (10,000 rpm, 4° C., 10 minutes) to obtain a precipitate. This precipitate was dissolved in 500 µl of elution buffer (composition: Tris HCl (pH 7.5): 2.5 mM, DTT: 1 mM, amidinophenylmethanesulfonyl fluoride hydrochloride (APMSF): 10 µM) followed by column purification using NAP-5 Columns Sephadex G-25 DNA Grade (GE Healthcare Inc.) and removal of the ammonium sulfate. This liquid was then used as "flower petal extract". The Avanti HP-26XP (rotor: JA-2) (Beckman Coulter Inc.) was used for centrifugation.

<Measurement of Enzyme Activity>

A reaction liquid prepared by mixing 40 µl of flower petal extract, 20 µl of 5 mM UDP-glucose, 20 µl of 1 M Tris HCl (pH 7.5) and 1 µl of 500 ng/µl apigenin on ice and bringing to a volume of 200 µl with water was held for 1 hour at 30° C. Subsequently, 200 µl of stop buffer (90% aqueous acetonitrile solution containing 0.1% TFA) were added to stop the reaction followed by analyzing the reaction liquid by high-performance liquid chromatography (Prominence (Shimadzu Corp.)). The Shimadzu PDA SPD-M10AVP was used for the detector and flavone was detected at 330 nm. The Shim-Pack ODS 150 mm×4.6 mm column (Shimadzu Corp.) was used for the column. A Solution A (0.1% aqueous TFA solution) and a Solution B (90% aqueous acetonitrile solution containing 0.1% TFA) were used for elution. Elution was carried out using a linear concentration gradient from an 8:2 mixture of the two solutions to a 3:7 mixture of the two solutions over the course of 10 minutes followed by a 3:7 mixture for 5 minutes. The flow rate was 0.6 ml/min. A reaction liquid obtained by allowing enzyme to react under the same conditions using a flower petal extract obtained by heat-treating the flower petal extract for 20 minutes at 100° C. was used as a control.

Figure 7:
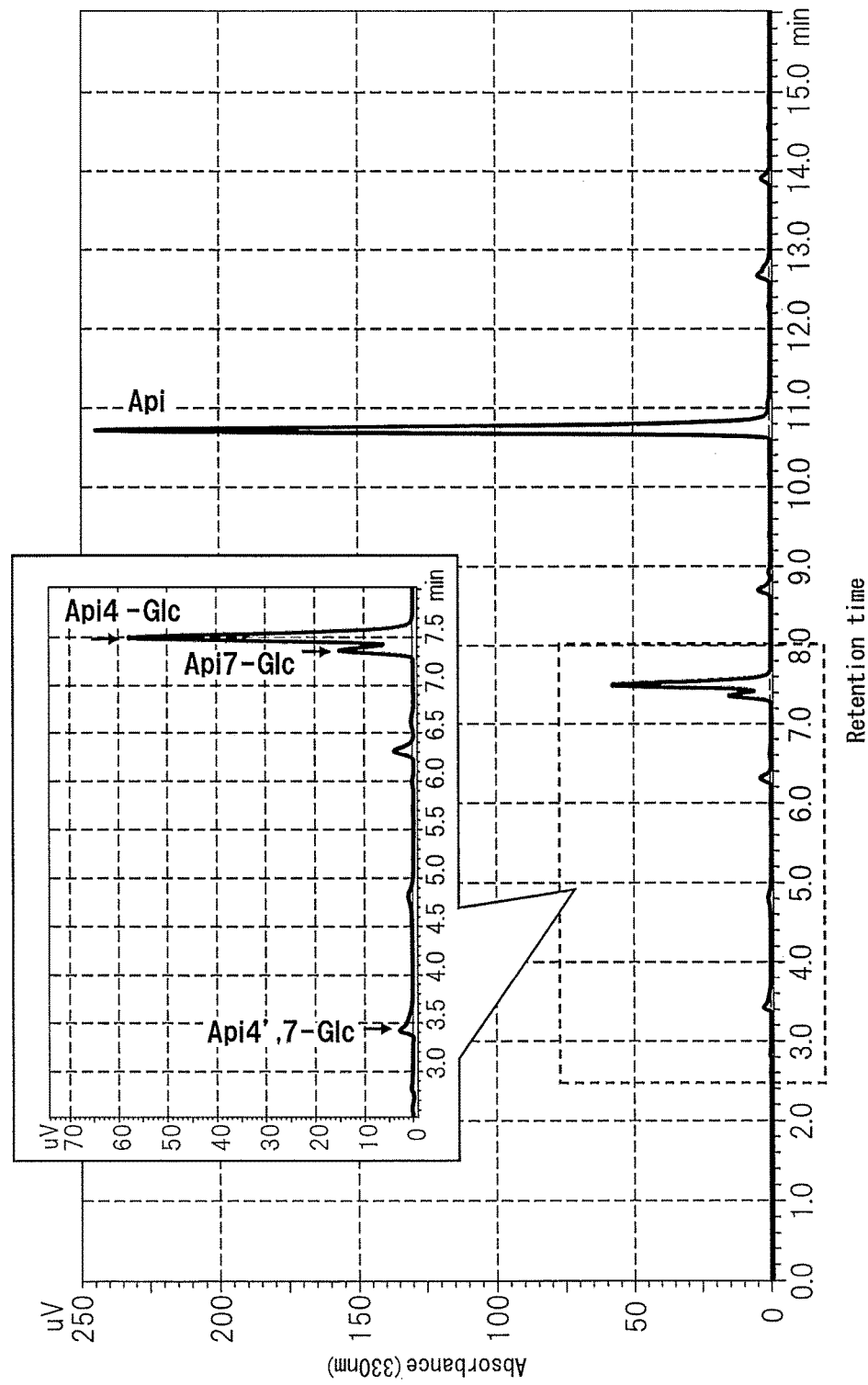
FIG. 7 is a high-performance liquid chromatogram obtained following an enzyme reaction between a flower petal extract and apigenin.

As a result, flavone demonstrating the same retention time and absorption maximum as purified apigenin 4',7-diglucoside and apigenin 7-glucoside standard was biosynthesized in addition to flavone demonstrating retention time close to that of apigenin 7-glucoside (see FIG. 7). Neither of these products was formed when the enzyme was allowed to react without adding UDP-glucose.

Example 2

Determination of Retention Time and Absorption Maximum of Apigenin 4'-Glucoside

Figure 8:
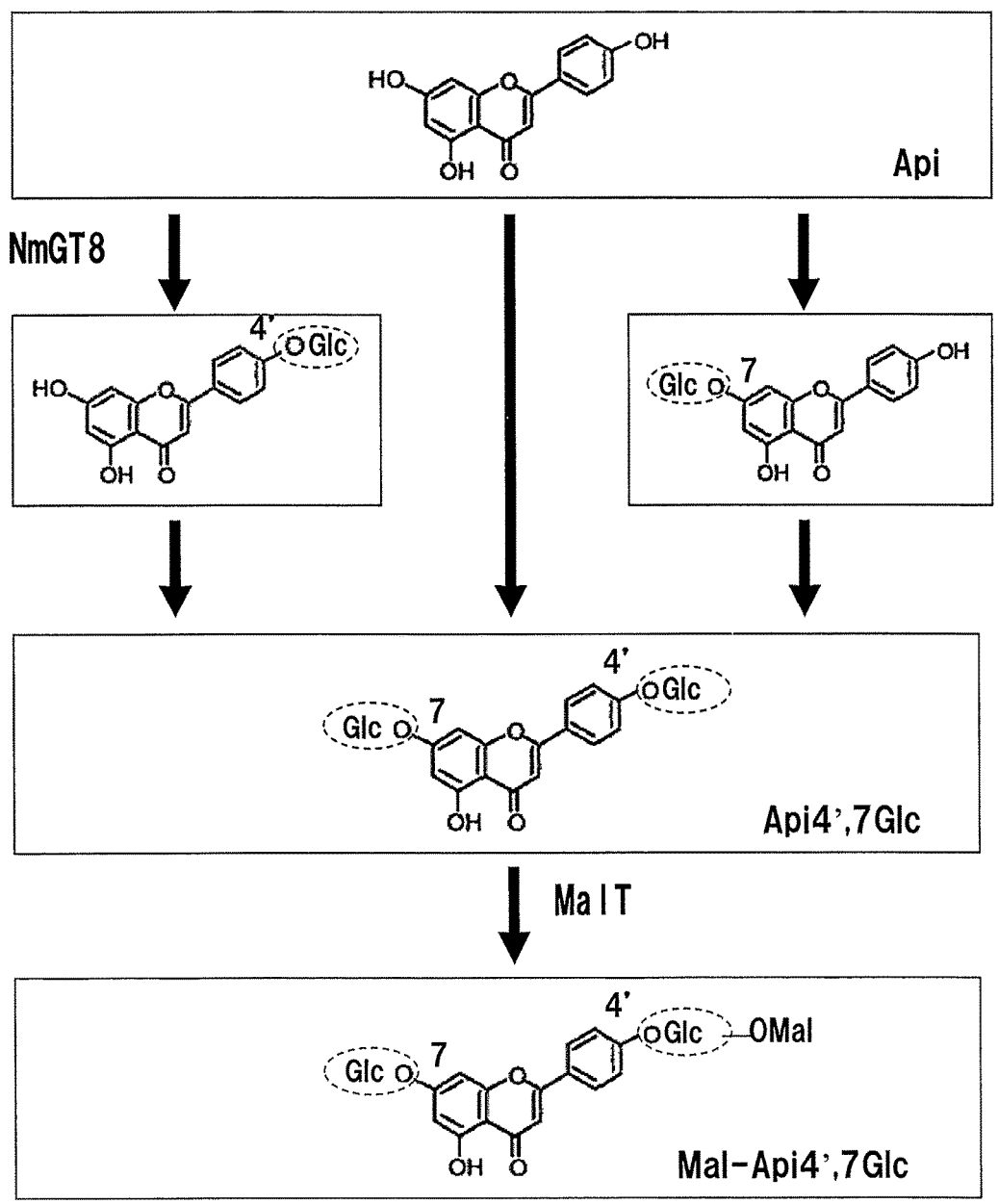
FIG. 8 is a drawing for explaining the biosynthesis pathway of apigenin4',7-diglucoside.

In consideration of the biosynthesis pathway of apigenin 4',7-diglucoside in *nemophila* flower petals, apigenin 4'-glucoside and apigenin 7-glucoside ought to be formed as intermediate products during course of biosynthesis of apigenin 4',7-diglucoside (see FIG. 8). On the basis thereof, the flavone demonstrating retention time close to that of apigenin 7-glucoside detected in Example 1 was judged to be apigenin 4'-glucoside (see FIG. 7). The retention time and absorption maximum of apigenin 4'-glucoside were able to be determined.

On the basis of these results, a protein having activity that transfers a sugar to the hydroxyl groups at the 4'-position and 7-position of a flavone that is dependent on UDP-glucose was clearly determined to be present in the flower petals of nemophila. Two possibilities were considered for the glycosylation of the hydroxyl groups at the 4'-position and 7-position, one possibility being that a single enzyme carries out glycosylation of both hydroxyl groups, and the other possibility being that glycosylation of the hydroxyl groups at the 4'-position and 7-position is respectively carried out by different enzymes.

Example 3

Acquisition of Candidate Genes for Gene Encoding Protein having Activity that Transfers a Sugar to the Hydroxyl Group at the 4'-Position of Flavone <Isolation of Total RNA>

Total RNA was isolated from stage 1 and stage 2 flower petals of nemophila using the Plant RNAeasy Kit (Qiagen Corp.) in accordance with the protocol recommended by the manufacturer.

<Analysis of Expression of cDNA Derived from Nemophila Flower Petals>

A reverse transcription reaction was carried out on 30 µg of total RNA derived from Nemophila flower petals followed by the production of a normalized cDNA library. After amplifying the resulting library for each clone by emulsion PCR, the base sequences were determined using an FLX Genome Sequencer (Roche Diagnostics K.K.). In addition, the resulting sequence data was translated to amino acid sequences followed by extraction of those sequences that demonstrated homology with the amino acid sequence of snapdragon anthocyanin 3'-glycosyltransferase. These sequences were then assembled to obtain candidate genes encoding glycosyltransferase.

Example 4

Acquisition of Full-Length cDNA Sequence of Candidate Genes Encoding Protein having Activity that Transfers a Sugar to the Hydroxyl Group at the 4'-Position of Flavone 25 types of sequences of glycosyltransferase gene were obtained in Example 3. Experiments were conducted to acquire full-length cDNA sequences for 10 of those sequences (NmGT0 to NmGT9).

Acquisition of full-length cDNA was carried out using GeneRacer (Invitrogen Corp.) in accordance with the protocol recommended by the manufacturer. Regions specific to the clones were selected from the cDNA partial sequences obtained in Example 3 and RACE primers were designed based on the sequences of these regions to obtain 5'- and 3'-terminal sequences by RACE PCR. Primers for amplifying the full-length cDNA sequence were designed based on these sequences, and a PCR reaction was carried out on 50 µl using nemophila cDNA as template and using KOD-Plus Polymerase (Toyobo Co., Ltd.) in accordance with the protocol recommended by the manufacturer (consisting of repeating 30 cycles of holding at 94° C. for 2 minutes, 94° C. for 15 seconds, 55° C. for 30 seconds and 68° C. for 2 minutes followed by holding at 4° C.). Nemophila cDNA was synthesized using the total RNA isolated in Example 2 using SuperScript II Reverse Transcriptase (Invitrogen Corp.) in accordance with the protocol recommended by the manufacturer. The primers were designed so as to contain restrictase sites on both ends of the full-length cDNA so as to enable the insertion of NmGT0 to NmGT9 genes into E. coli expression vector pET15b (Novagen Inc.). Plasmids containing the full length of the NmGT genes (pTOPO-NmGT0 to pTOPO-NmGT9) were acquired using the Zero Blunt TOPO PCR Cloning Kit for Sequencing (Invitrogen Corp.) in accordance with the protocol recommended by the manufacturer. Base sequences inserted with the plasmids were analyzed to acquire a full-length cDNA sequence (NmGT8: SEQ ID NO: 1) from among candidate genes (NmGT0 to NmGT9) for a gene encoding a protein having activity that transfers a sugar to the hydroxyl group at the 4'-position of a flavone.

Example 5

Experiment on Measurement of Enzyme Activity of Protein Candidates having Activity that Transfers a Sugar to the Hydroxyl Group at the 4'-Position of Flavone (Case of Using Crude Enzyme)

<Preparation of E. Coli Expression Constructs>

3 µg aliquots of each of pTOPO-NmGT0 to pTOPO-NmGT9 were treated with their corresponding restrictases followed by recovery of the resulting approximately 1.5 kb DNA fragments. 2 µg of vector pET15b was also treated with restrictase and ligated with the resulting DNA fragments to prepare E. coli expression constructs (pET-NmGT0 to pET-NmGT9).

<Expression of Glycosyltransferase in E. Coli> pET-NmGT0 to pET-NmGT9 were introduced into E. coli strain BL2 using One Shot BL21 (DE3) (Invitrogen Corp.) in accordance with the protocol recommended by the manufacturer to acquire transformed E. coli. This E. coli was then cultured using the Overnight Express Autoinduction System 1 (Novagen Inc.) in accordance with the protocol recommended by the manufacturer. The transformed E. coli were cultured at 37° C. to an OD600 value of 0.5 in 2 ml of the prepared culture liquid (approx. 4 hours). This E. coli culture liquid was then used as a pre-culture liquid and added to 50 ml of culture liquid followed by final culturing overnight at 27° C.

Following final culturing overnight, the E. coli culture liquid was centrifuged (3000 rpm, 4° C., 15 minutes), the collected cells were suspended in 5 ml of sonic buffer (composition: Tris HCl (pH 7.0): 2.5 mM, dithiothreitol (DTT): 1 mM, amidinophenylmethanesulfonyl fluoride hydrochloride (APMSF): 10 µl ), and after crushing the E. coli by ultrasonic treatment, the crushed cells were centrifuged (15,000 rpm, 4° C., 10 minutes) followed by recovery of the supernatant. This supernatant was used as a crude enzyme liquid. The Avanti HP-26XP (rotor: JA-2) (Beckman Coulter Inc.) was used for centrifugation.

<Measurement of Enzyme Activity>

A reaction liquid prepared by mixing 80 µl of crude enzyme liquid, 20 µl of 5 mM UDP-glucose, 20 µl of 1 M Tris HCl (pH 7.5) and 1 µl of 500 ng/µl apigenin on ice and bringing to a volume of 200 µl with water was held for 1 hour at 30° C. Subsequently, 200 µl of stop buffer (90% aqueous acetonitrile solution containing 0.1% TFA) were added to stop the reaction followed by analyzing the reaction liquid by high-performance liquid chromatography (Prominence (Shimadzu Corp.)). The Shimadzu PDA SPD-M10AVP was used for the detector and flavone was detected at 330 nm. The Shim-Pack ODS 150 mm×4.6 mm column (Shimadzu Corp.) was used for the column. A Solution A (0.1% aqueous TFA solution) and a Solution B (90% aqueous acetonitrile solution containing 0.1% TFA) were used for elution. Elution was carried out using a linear concentration gradient from an 8:2 mixture of the two solutions to a 3:7 mixture of the two solutions over the course of 10 minutes followed by a 3:7 mixture for 5 minutes. The flow rate was 0.6 ml/min. A reaction liquid obtained by allowing enzyme to react under the same conditions using a crude enzyme liquid of *E. coli* introduced with a pET vector not inserted with an insert was used as a control.

As a result, a peak other than that of the substrate was observed for NmGT8.

Descriptions starting with that of Example 6 are described with respect to NmGT8 (SEQ ID NO: 1).

Example 6

Experiment on Measurement of Enzyme Activity of Protein having Activity that Transfers a Sugar to the Hydroxyl Group at the 4'-Position of Flavone (Case of Using His-Tag-Added Protein <Expression of Glycosyltransferase in *E. coli* and Protein Purification>

*E. coli* strain BL2 introduced with the pET-NmGT8 described in Example 5 was cultured using the Overnight Express Autoinduction System 1 (Novagen Inc.) in accordance with the protocol recommended by the manufacturer. The transformed *E. coli* were cultured at 37° C. to an OD600 value of 0.5 in 8 ml of the prepared culture liquid (approx. 4 hours). This *E. coli* culture liquid was then used as a pre-culture liquid and added to 200 ml of culture liquid followed by final culturing overnight at 25° C.

Following final culturing overnight, the *E. coli* culture liquid was centrifuged (1000×g, 4° C., 10 minutes), the collected cells were suspended in 20 ml of extract (composition: buffer (KCl: 300 mM, $KH_2PO_4$: 50 mM, imidazole: 5 mm) (pH 8.0), amidinophenylmethanesulfonyl fluoride hydrochloride (APMSF): 10 µM), and after crushing the *E. coli* by ultrasonic treatment, the crushed cells were centrifuged (1400×g, 4° C., 20 minutes) followed by recovery of the supernatant. This supernatant was passed through a 0.45 µm filter and purified by His-Tag protein purification using Profinia (Bio-Rad Laboratories, Inc.) in accordance with the protocol recommended by the manufacturer. The resulting purified protein solution was centrifuged (7500×g, 4° C., 15 minutes) using centrifugal filters (Ultracel-10K, Amicon Corp.) and the concentrated protein solution was designated as "NmGT8 Protein Solution". The Avanti HP-26XP (rotor: JA-2) (Beckman Coulter Inc.) was used for centrifugation.

<Measurement of Enzyme Activity>

A reaction liquid prepared by mixing 10 µl of protein solution, 2 µl of 50 mM UDP-glucose, 10 µl of 1 M Tris HCl (pH 7.5) and 5 µl of 1 mM apigenin on ice and bringing to a volume of 100 µl with water was held for 20 minutes at 30° C. Subsequently, 100 µl of stop buffer (90% aqueous acetonitrile solution containing 0.1% TFA) were added to stop the reaction followed by analyzing the reaction liquid by high-performance liquid chromatography (Prominence (Shimadzu Corp.)). The Shimadzu PDA SPD-M10AVP was used for the detector and flavone was detected at 330 nm. The Shim-Pack ODS 150 mm×4.6 mm column (Shimadzu Corp.) was used for the column. A Solution A (0.1% aqueous TFA solution) and a Solution B (90% aqueous methanol solution containing 0.1% TFA) were used for elution. Elution was carried out using a linear concentration gradient from an 8:2 mixture of the two solutions to a 3:7 mixture of the two solutions over the course of 10 minutes followed by a 3:7 mixture for 6 minutes. The flow rate was 0.6 ml/min.

Figure 9:
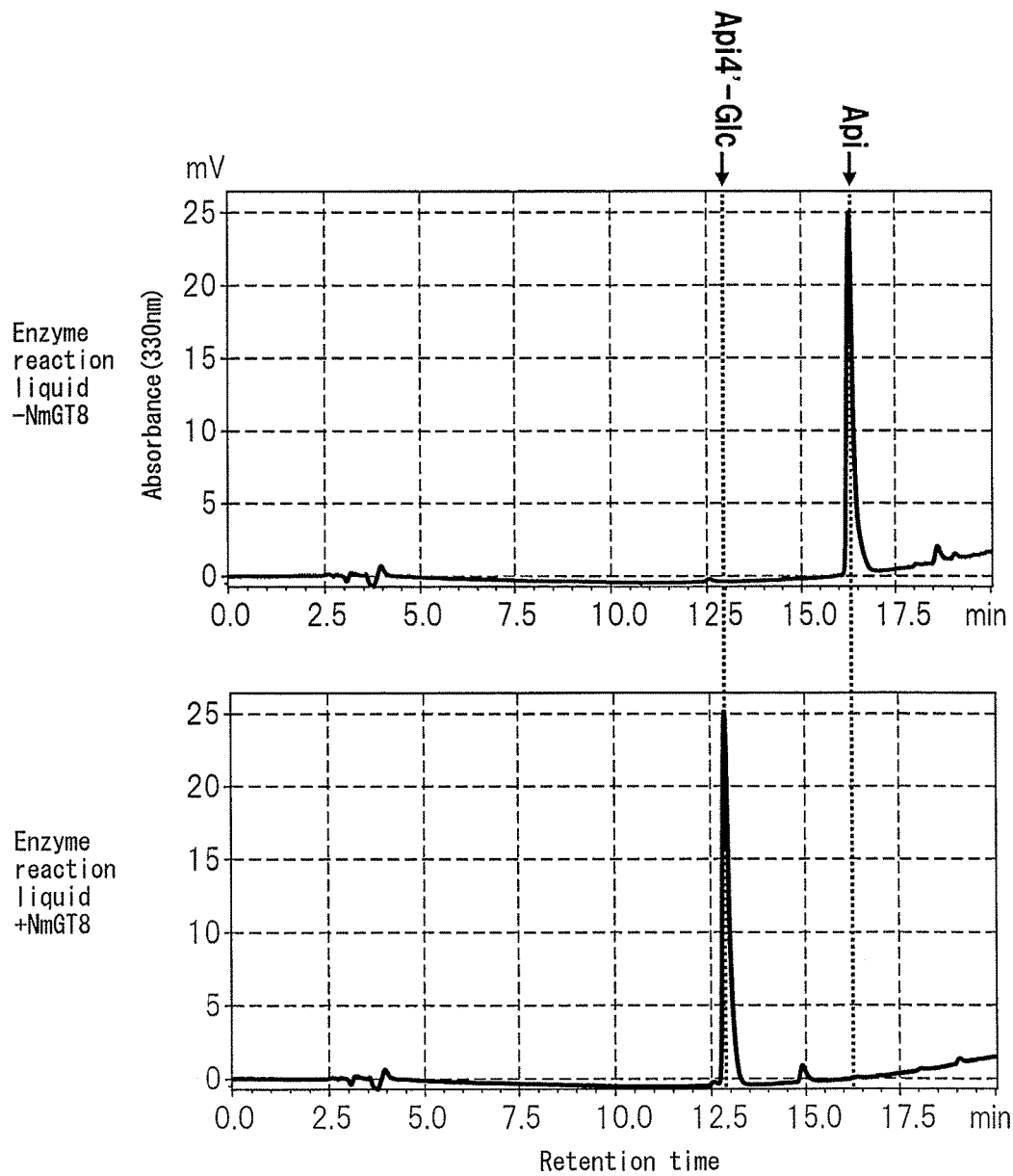
FIG. 9 is a high-performance liquid chromatogram obtained following an enzyme reaction between NmGT8 protein solution and apigenin.
Figure 10:
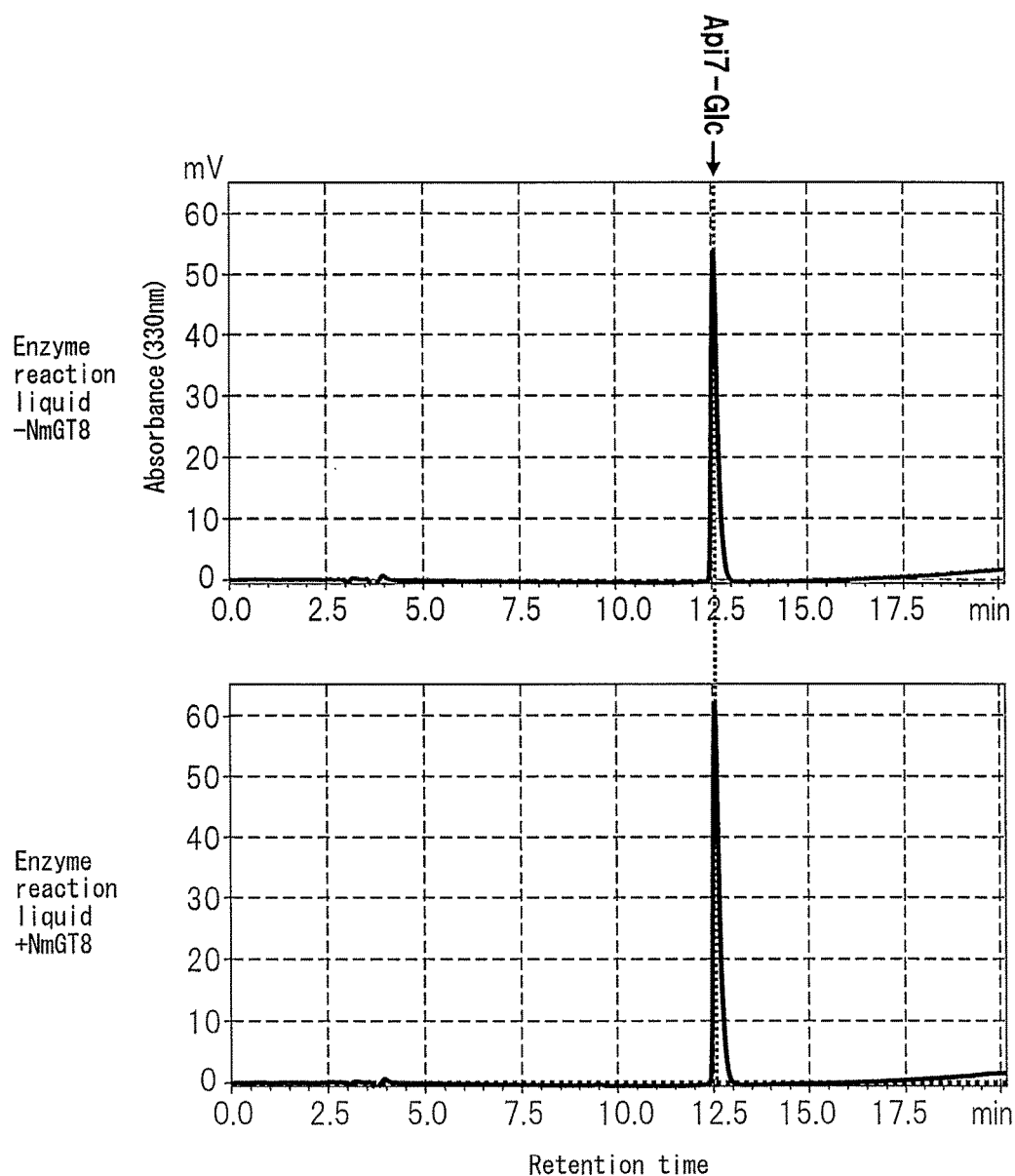

As a result, flavone demonstrating the same retention time and absorption maximum as purified apigenin 4'-glucoside was biosynthesized (see FIG. 9). Luteolin 4'-glucoside was biosynthesized in the case of carrying out an enzyme reaction under the same conditions by replacing the substrate with another flavone in the form of luteolin (see FIG. 11). On the other hand, apigenin 4',7-diglucoside was not biosynthesized in the case of carrying out the enzyme reaction under the same conditions by replacing the substrate with 1 mM apigenin 7-glucoside (see FIG. 10). Similarly, luteolin 4',7-diglucoside was also not biosynthesized in the case of carrying out the enzyme reaction under the same conditions by replacing the substrate with 1 mM luteolin 7-glucoside (see FIG. 11). On the basis thereof, NmGT8 protein was clearly determined to carry out glycosylation of the 4'-position prior to glycosylation of the 7-position of apigenin and luteolin (see FIG. 8). Moreover, when reactivity to the various types of flavone compounds described in FIG. 11 and betanidine was investigated, NmGT8 protein was clearly determined to demonstrate high substrate specificity and selectively glycosylate the 4'-position of flavones in the manner of apigenin and luteolin (see FIG. 11).

Furthermore, although glycosyltransferase gene derived from Livingstone daisy (Dbs5GT) transfers glucose to the hydroxyl group at the 5-position of betanidine, it has also been reported to demonstrate activity in vitro that transfers glucose to the hydroxyl group at one of either the 4'-position or 7-position of a flavonoid. This glycosyltransferase derived from Livingstone daisy was clearly determined to differ considerably from the NmGT8 protein of the present invention with respect to reactivity to flavonoid compounds and betanidine (see FIG. 11).

Amino acid sequence identities between NmGT8 and NmGT3 and between NmGT8 and NmGT4 were 32% and 32%, respectively (see FIGS. 12-1 to 12-3). The Clustal W Program of the MacVector Application (Version 11.02, Oxford Molecular Ltd., Oxford, England) was used for this analysis. Among previously identified glycosyltransferases, the amino acid sequence having the highest identity with NmGT8 was that of an enzyme that adds a sugar to the 3-position and 5-position of rose anthocyanidin (GenBank Accession No, Q4R19) (SEQ ID NO: 15), and demonstrated amino acid sequence identity of 52% (see FIG. 14). Next, an amino add sequence having high identity with NmGT8 was that of an enzyme that adds a sugar to the 4'-position of snapdragon chalcone (described in PCT/JP2004/1019461) (SEQ ID NO: 14), and this demonstrated identity of 51% (see FIG. 13).

In addition, FIG. 15 shows a phylogenetic tree indicating the relationships between the NmGT8 of the present invention and the aforementioned enzymes.

Example 7

Expression of Gene Encoding Peptide Having Activity that Transfers a Sugar to the Hydroxyl Group at the 4'-Position of Flavone in Torenia A binary vector pSPB4583 for expressing NmGT8 was constructed and introduced into torenia (Summer Wave) in

19 order to confirm whether or not the NmGT8 gene of the present invention translates a protein having activity that transfers a sugar to the hydroxyl group at the 4'-position of a flavone in plants. Details of the introduced construct are described below (see FIG. 16).

<Preparation of Construct>

The binary vector pBINPLUS for introduction into plants (van Engel, et al., Transgenic Research, 4, p. 288) was used for the basic skeleton of pSPB4583, and EI235S promoter having two repetitions of an enhancer sequence upstream from cauliflower mosaic virus 35S promoter (Mitsuhara, et al., (1996) Plant Cell Physiol., 37, p. 49), full-length cDNA NmGT8 and mas terminator were contained therein.

<Gene Expression Analysis>

Gene expression analysis was carried out by forming chutes in selective media containing kanamycin, acclimating individuals in which rooting was observed, and using the petals of buds of each recombinant torenia in which the calyx had not yet split. Isolation of total RNA was carried out in the same manner as that described in Example 3, and synthesis of cDNA was carried out in the same manner as the method described in Example 4. A reverse transcription PCR reaction was carried out on 30 μl using the cDNA as template and using ExTaq Polymerase (Takara Co., Ltd.) in accordance with the protocol recommended by the manufacturer (consisting of repeating 25 cycles of holding at 94° C. for 2 minutes, 94° C. for 1 minute, 55° C. for 1 minute and 72° C. for 2 minutes followed by holding at 4° C.). Buffers were designed so as to specifically amplify each full-length cDNA. As a result, NmGT8 was confirmed to be transcribed in Torenia.

Example 8

Expression of Gene Encoding Protein Having Activity that Transfers a Sugar to the Hydroxyl Group at the 4'-Position of Flavone in Petunia Binary vectors pSPB5424 and pSBP5428 for expressing NmGT8 were constructed and introduced into petunia (Surfinia Bouquet Red). Since petunia does not biosynthesize flavones naturally, the vectors were introduced together with torenia flavone synthase and evaluated as to whether or not NmGT8 has activity that transfers a sugar to the hydroxyl group at the 4'-position of a flavone in petunia. Details of the introduced constructs are described below (see FIG. 17).

<Preparation of Constructs> pBINPLUS was used for the basic skeleton of pSPB5424, and three expression cassettes were contained therein (consisting of 1: EI235S promoter, full-length cDNA pansy F3'5'H (described in PCT/JP2004/011958, SEQ ID NO: 3) and HSP terminator (Plant Cell Physiology (2010), 51, 328-332); 2: EI235S promoter, full-length cDNA torenia flavone synthase and HSP terminator; and 3: EI235S promoter, full-length cDNA NmGT8 and HSP terminator).

pBINPLUS was also used for the basic skeleton of pSPB5428, and two expression cassettes were contained therein (consisting of 1: EI235S promoter, full-length cDNA torenia flavone synthase and HSP terminator; and 2: EI235S promoter, full-length cDNA NmGT8 and HSP terminator).

<Gene Expression Analysis>

Gene expression analysis was carried out in the same manner as the method described in Example 7 by forming chutes in selective media containing kanamycin, acclimating individuals in which rooting was observed, and using the petals of flowers of each recombinant petunia that had completely opened. As a result, NmGT8 was confirmed to be transcribed in petunia.

<Flower Petal Pigment Analysis>

Pigments in the flower petals were analyzed for full-length cDNA torenia flavone synthase and full-length cDNA NmGT8 in those stains in which transcription products were confirmed. 0.2 g of completely open flower petals were freeze-dried for 24 hours or more and finely crushed with a spatula, followed by the addition of 4 ml of extract buffer (composition: 50% aqueous acetonitrile solution containing 0.1% TFA) and subjecting to ultrasonic treatment for 20 minutes. The flower petal extract was analyzed by high-performance liquid chromatography (Prominence (Shimadzu Corp.)). Analyses were carried out under the conditions and in the same manner as in Example 5. Non-recombinant petunia not introduced with genes and recombinant petunia introduced only with torenia flavone synthase that biosynthesizes flavone were analyzed in the same manner as controls (FIG. 18). Moreover, flower petal extract diluted 50-fold was also analyzed with a high-performance liquid chromatograph (Shimadzu Corp.). The Shimadzu LCMS-IF-TOF was used for the detector and flavones were detected at 433.1057 ([Api-Glc+H]) and 449.1084 ([Lut-Glc+H]). The Inertsil ODS-4 (250×4.6 mm, 5 Shimadzu Corp.) was used for the column. A Solution A (0.1% aqueous formic acid solution) and a Solution B (90% aqueous acetonitrile solution containing 0.1% formic acid) were used for elution. Elution was carried out using a linear concentration gradient from a 9:1 mixture of the two solutions to an 11:9 mixture of the two solutions over the course of 35 minutes and a linear concentration gradient from an 11:9 mixture of the two solutions to a 0:10 mixture of the two solutions over the course of 10 minutes followed by a 0:10 mixture for 5 minutes. The flow rate was 0.6 ml/min (FIG. 19).

As a result, apigenin 4'-glucoside and luteolin 4'-glucoside were detected in the recombinant petunia introduced with flavone synthase and NmGT8 (FIG. 18), and flavone 4'-glucoside was determined to account for 95.6% of the biosynthesized flavones. The remaining 4.4% was determined to consist of flavone 7-glucoside biosynthesized by the intrinsic activity of petunia that transfers a sugar to the hydroxyl group at the 7-position of a flavone (FIG. 19). On the other hand, flavones were not detected in the non-recombinant petunia, and flavone 7-glucoside was determined to account for 82.8% of the biosynthesized flavones in the recombinant petunia introduced only with torenia flavone synthase. On the basis thereof, NmGT8 was clearly demonstrated to be a protein having activity that transfers a sugar to the hydroxyl group at the 4'-position of a flavone that functions preferentially over protein having activity that transfers a sugar to the hydroxyl group at the 7-position of a flavone that is intrinsic to petunia. The use of NmGT8 makes it possible to efficiently biosynthesize flavone 4'-glucoside in petunia.

Example 9

Expression of Gene Encoding Protein Having Activity that Transfers a Sugar to the Hydroxyl Group at the 4'-Position of Flavone in Carnation A binary vector pSPB5433 for expressing NmGT8 was constructed and introduced into carnation (Cream Cinderella). Since carnation does not biosynthesize flavones naturally, the vector was introduced together with torenia flavone synthase and evaluated as to whether or not NmGT8 has activity that transfers a sugar to the hydroxyl group at the 4'-position of a flavone in carnation. Details of the introduced construct are described below (see FIG. 20).

The binary vector pWTT2132 for introduction into plants (DNA Plant Technologies, USA=DNAP) was used for the basic skeleton of pSPB5433, and four expression cassettes were contained therein (consisting of 1: snapdragon chalcone synthase promoter (described in PCT/AU94/00265), full-length cDNA pansy F3'5'H and HSP terminator; 2: snapdragon chalcone synthase promoter, full-length cDNA torenia flavone synthase and HSP terminator; 3: carnation anthocyanin synthase promoter (described in PCT/AU/2009/001659), full-length cDNA NmGT8 and HSP terminator; and, 4: carnation anthocyanin synthase promoter, full-length cDNA NmGT3 (Japanese Patent Application No. 2011-006317) and HSP terminator).

Example 10

Expression of Gene Encoding Protein Having Activity that Transfers a Sugar to the Hydroxyl Group at the 4'-Position of Flavone in Rose Binary vectors pSPB4577, pSBP4578, pSBP5437 and pSBP5440 for expressing NmGT8 were constructed and introduced into rose (Noblesse, Ritapa Humera). Since rose does not biosynthesize flavones naturally, the vectors were introduced together with torenia flavone synthase and evaluated as to whether or not NmGT8 has activity that transfers a sugar to the hydroxyl group at the 4'-position of a flavone in rose. Details of the introduced constructs are described below (see FIG. 21).

pBINPLUS was used for the basic skeleton of pSPB5477, and three expression cassettes were contained therein (consisting of 1: EI235S promoter, full-length cDNA pansy F3'5'H and mas terminator; 2: EI235S promoter, full-length cDNA torenia flavone synthase and mas terminator; and, 3: EI235S promoter, full-length cDNA NmGT8 and mas terminator).

pBINPLUS was used for the basic skeleton of pSPB4578, and three expression cassettes were contained therein (consisting of 1: perilla anthocyanin 3-acyltransferase promoter (described in PCT/JP2010/053909), full-length cDNA pansy F3'5'H and mas terminator; 2: EI235S promoter, full-length cDNA torenia flavone synthase and mas terminator; and, 3: EI235S promoter, full-length cDNA NmGT8 and mas terminator).

pBINPLUS was used for the basic skeleton of pSPB5437, and five expression cassettes were contained therein (consisting of 1: EI235S promoter, full-length cDNA pansy F3'5'H and HSP terminator; 2: perilla anthocyanin 3-.acyltransferase chromogene (described in PCT/JP2010/053886, see SEQ ID NO: 7); 3: EI235S promoter, full-length cDNA torenia flavone synthase and HSP terminator; 4: EI235S promoter, full-length cDNA NmGT8 and HSP terminator); and, 5: EI235S promoter, full-length cDNA NmGT3 and HSP terminator).

pBINPLUS was used for the basic skeleton of pSPB5440, and five expression cassettes were contained therein (consisting of 1: EI235S promoter, full-length cDNA pansy F3'5'H and HSP terminator; 2: EI235S promoter, cDNA lavender anthocyanin 3-acyltransferase (described in PCT/JP1996/000348, see SEQ ID NO: 8); 3: EI235S promoter, full-length cDNA torenia flavone synthase and HSP terminator; 4: EI235S promoter, full-length cDNA NmGT8 and HSP terminator); and, 5: EI235S promoter, full-length cDNA NmGT3 and HSP terminator).

<Gene Expression Analysis>

Gene expression analysis was carried out in the same manner as the method described in Example 7 by forming chutes in selective media containing kanamycin, acclimating individuals in which rooting was observed, and using the petals of flowers of each recombinant rose that had completely opened. As a result, NmGT8 was confirmed to be transcribed in rose.

<Flower Petal Pigment Analysis>

Figure 23:
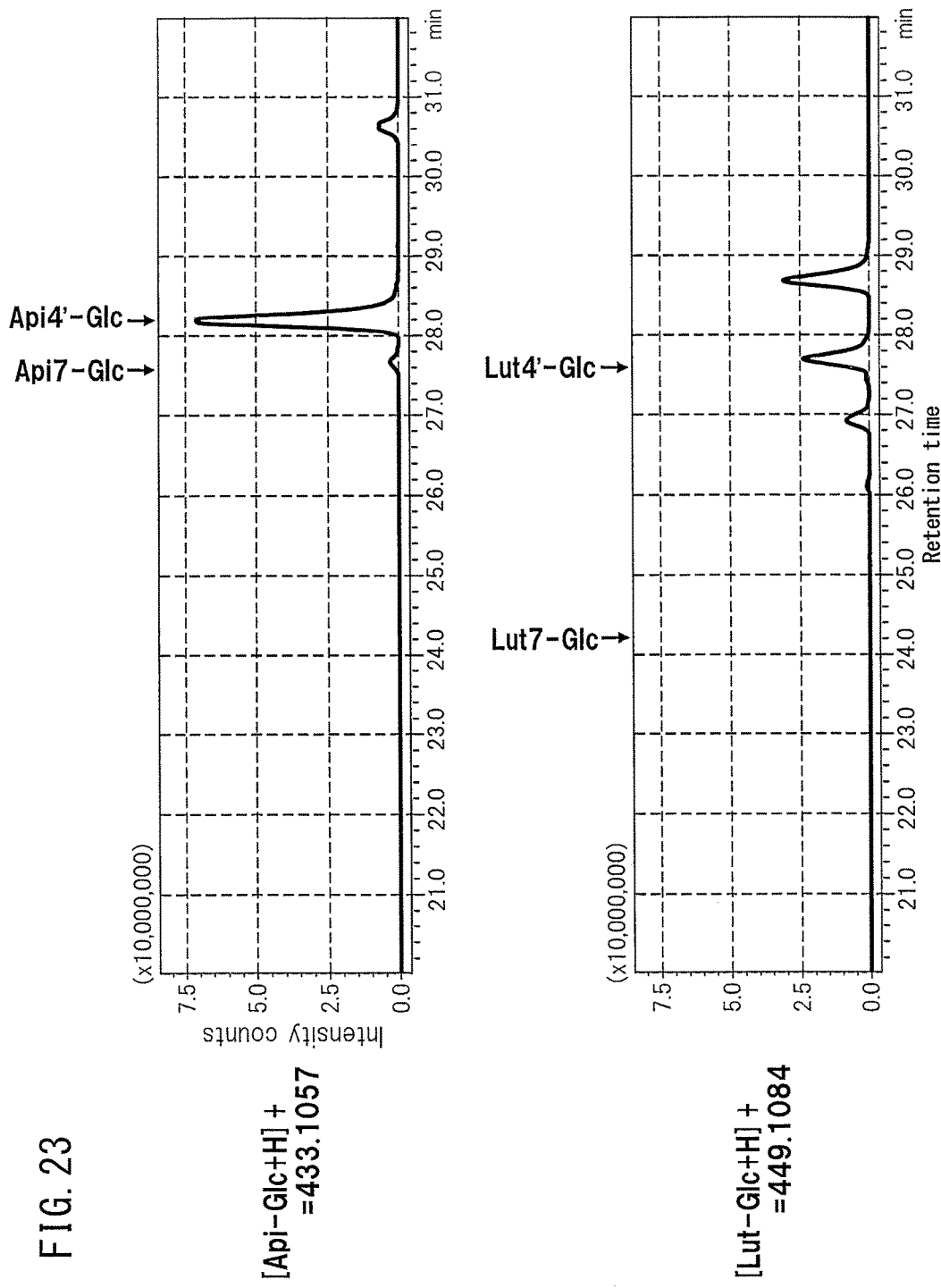

Pigments in the flower petals were analyzed for full-length cDNA torenia flavone synthase and full-length cDNA NmGT8 in those strains in which transcription products were confirmed. 0.2 g of completely open flower petals were freeze-dried for 24 hours or more and finely crushed with a spatula, followed by the addition of 4 ml of extract buffer (composition: 50% aqueous acetonitrile solution containing 0.1% TFA) and subjecting to ultrasonic treatment for 20 minutes. The flower petal extract was analyzed by high-performance liquid chromatography (Prominence (Shimadzu Corp.)). Analyses were carried out under the conditions and in the same manner as in Example 5. Non-recombinant rose not introduced with the genes was analyzed in the same manner as a control (FIG. 22). Flower petal extract diluted 50-fold was also analyzed with a high-performance liquid chromatograph (Shimadzu Corp.). The Shimadzu LCMS-IF-TOF was used for the detector and flavones were detected at 433.1057 nm ([Api-Glc+H]) and 449.1084 nm ([Lut-Glc+H]). The Inertsil ODS-4 (250×4.6 mm, 5 μm, Shimadzu Corp.) was used for the column. A Solution A (0.1% aqueous formic acid solution) and a Solution B (90% acetonitrile solution containing 0.1% formic acid) were used for elution. Elution was carried out using a linear concentration gradient from a 9:1 mixture of the two solutions to an 11:9 mixture of the two solutions over the course of 35 minutes and a linear concentration gradient from an 11:9 mixture of the two solutions to a 0:10 mixture of the two solutions over the course of 10 minutes followed by a 0:10 mixture for 5 minutes. The flow rate was 0.6 ml/min (FIG. 23).

As a result, apigenin 4'-glucoside and luteolin 4'-glucoside were detected in the recombinant rose introduced with flavone synthase and NmGT8 (FIG. 22), and flavone 4'-glucoside was determined to account for 97.0% of the biosynthesized flavones. The remaining 3.0% was determined to consist of flavone 7-glucoside biosynthesized by the intrinsic activity of rose that transfers a sugar to the hydroxyl group at the 7-position of a flavone (FIG. 23). On the other hand, flavones were not detected in the non-recombinant rose. On the basis thereof, NmGT8 was clearly demonstrated to be a protein having activity that transfers a sugar to the hydroxyl group at the 4'-position of a flavone that functions preferentially over protein having activity that transfers a sugar to the hydroxyl group at the 7-position of a flavone that is intrinsic to rose. The use of NmGT8 makes it possible to efficiently biosynthesize flavone 4'-glucoside in rose.

INDUSTRIAL APPLICABILITY

In the present invention, a polynucleotide encoding a protein having activity that transfers a sugar to the hydroxyl group at the 4'-position of a flavone was identified for the first time. Expression of the polynucleotide of the present invention in suitable host cells makes it possible to produce a protein having activity that specifically transfers a sugar to the hydroxyl group at the 4'-position of a flavone. According to the present invention, constitutively or tissue-specifically expressing a protein having activity that transfers a sugar to the hydroxyl group at the 4'-position of a flavone in a plant can be used to alter flower color. In addition, according to the present invention, a method for producing a flavone in which a sugar has been added to the hydroxyl group at the 4'-position thereof, and a food, pharmaceutical or cosmetic obtained according to that production method, are provided.

The invention claimed is:

1. A recombinant expression vector comprising a polynucleotide operably linked to a heterologous promoter, wherein the polynucleotide is selected from the group consisting of the following (a) to (d):
   (a) a polynucleotide comprising the nucleotide sequence of SEQ ID NO: 1;
   (b) a polynucleotide encoding a protein comprising the amino acid sequence of SEQ ID NO: 2;
   (c) a polynucleotide encoding a protein having one to five amino acids deleted, substituted, or inserted in the amino acid sequence of SEQ ID NO: 2, and having an activity of transferring a sugar group to the hydroxyl group at the 4'-position of a flavone; and,
   (d) a polynucleotide encoding a protein having an amino acid sequence identity of 95% or more with SEQ ID NO: 2, and having an activity of transferring a sugar group to the hydroxyl group at the 4'-position of a flavone.

2. A non-human host transformed by the recombinant expression vector of claim 1.

3. A plant transformed by the recombinant expression vector of claim 1, a progeny thereof, a portion of the transformed plant or the progeny, or a tissue of the transformed plant or the progeny, wherein each of the plant, the progeny, the portion, and the tissue comprises the recombinant vector.

4. A portion of the plant of claim 3, wherein the portion is a cut flower.

5. A processed cut flower obtained from the cut flower of claim 4.

6. A method for producing a protein having an activity of transferring a sugar group to the hydroxyl group at the 4'-position of a flavone, comprising the following steps:
   culturing or growing the non-human host of claim 2, and
   harvesting, from the non-human host, the protein having the activity of transferring a sugar group to the hydroxyl group at the 4'-position of a flavone.

7. A method for producing a flavone in which a sugar group has been added to the hydroxyl group at the 4'-position thereof, comprising the following steps:
   culturing or growing the non-human host of claim 2, and
   harvesting, from the non-human host, the flavone in which a sugar group has been added to the hydroxyl group at the 4'-position thereof.

8. The recombinant expression vector of claim 1, wherein the heterologous promoter is selected from the group consisting of a bacterial promoter, a yeast promoter, a filamentous fungi promoter, and a promoter for animal cell hosts.

9. The recombinant expression vector of claim 1, wherein the heterologous promoter constitutively expresses a gene in plant cells.

10. The recombinant expression vector of claim 9, wherein the heterologous promoter is selected from the group consisting of cauliflower mosaic virus 35S RNA promoter, rd29A gene promoter, rbcS promoter, and mac-1 promoter.

11. The recombinant expression vector of claim 1, wherein the heterologous promoter specifically expresses a gene in a plant tissue.

* * * * *

```
                         SEQUENCE LISTING

<160> NUMBER OF SEQ ID NOS: 15

<210> SEQ ID NO 1
<211> LENGTH: 1425
<212> TYPE: DNA
<213> ORGANISM: Nemophila menziesii
<220> FEATURE:
<221> NAME/KEY: misc_feature
<222> LOCATION: (1)..(1425)
<223> OTHER INFORMATION: NmGT8
<220> FEATURE:
<221> NAME/KEY: CDS
<222> LOCATION: (1)..(1422)

<400> SEQUENCE: 1 atg gag aaa aaa act att att ctg tat ccc tct cca ggc ata ggt cac      48
Met Glu Lys Lys Thr Ile Ile Leu Tyr Pro Ser Pro Gly Ile Gly His
1               5                   10                  15 tta gtt tcc atg gtt gag ctt gct aag ctc att ctt aat cgt gaa cca      96
Leu Val Ser Met Val Glu Leu Ala Lys Leu Ile Leu Asn Arg Glu Pro
            20                  25                  30 tca tac tcc atc att atc ttt att tct tca gca cca tac tct act ggc     144
Ser Tyr Ser Ile Ile Ile Phe Ile Ser Ser Ala Pro Tyr Ser Thr Gly
        35                  40                  45 tca agt gcc cct tat att agc cat gtt tca gcc acc aca tca ggc atc     192
Ser Ser Ala Pro Tyr Ile Ser His Val Ser Ala Thr Thr Ser Gly Ile
    50                  55                  60 tcc ttc cac cac ctc cct gtc ctc gtc ctt ccc ccc aac acc ttc agc     240
Ser Phe His His Leu Pro Val Leu Val Leu Pro Pro Asn Thr Phe Ser
65                  70                  75                  80 tcc ttc gaa gaa ata gca tat aaa att cct caa ctt aac aat ccc aat     288
Ser Phe Glu Glu Ile Ala Tyr Lys Ile Pro Gln Leu Asn Asn Pro Asn
                85                  90                  95 tta aaa cta gcc ctt caa aca atc tcc aaa gaa tca agt gat ctc aaa     336
Leu Lys Leu Ala Leu Gln Thr Ile Ser Lys Glu Ser Ser Asp Leu Lys
            100                 105                 110 gcc ttc atc ata gac ttc ttc tgc act gct gca gtt gaa gtc tct tca     384
Ala Phe Ile Ile Asp Phe Phe Cys Thr Ala Ala Val Glu Val Ser Ser
        115                 120                 125 aac ctt gaa att cct acc tat ttc ttc ttt aca tct ggt tct tct gct     432
Asn Leu Glu Ile Pro Thr Tyr Phe Phe Phe Thr Ser Gly Ser Ser Ala
    130                 135                 140 atg tgt caa ttc cta tac ctt cca act ctt cat gaa acc ata acc caa     480
Met Cys Gln Phe Leu Tyr Leu Pro Thr Leu His Glu Thr Ile Thr Gln
145                 150                 155                 160 aaa gac ttg caa gat cct aac act tac gtt cac att cca ggt att cca     528
Lys Asp Leu Gln Asp Pro Asn Thr Tyr Val His Ile Pro Gly Ile Pro
                165                 170                 175 cct atc cat tct tta gac ttg cct aag gtt tta tcc aat agg agt acc     576
Pro Ile His Ser Leu Asp Leu Pro Lys Val Leu Ser Asn Arg Ser Thr
            180                 185                 190 gtg tta tat aaa gag ctt ata aac act gca aac cag atg gca aag tgt     624
Val Leu Tyr Lys Glu Leu Ile Asn Thr Ala Asn Gln Met Ala Lys Cys
        195                 200                 205 tct gga atc ttg ata aac gca ttt gaa aca ctt gaa cca aaa gct gtc     672
Ser Gly Ile Leu Ile Asn Ala Phe Glu Thr Leu Glu Pro Lys Ala Val
    210                 215                 220
```

```
aaa gca tta aaa gaa ggt tta tgc acc cct ggt atg cca act cca cct         720
Lys Ala Leu Lys Glu Gly Leu Cys Thr Pro Gly Met Pro Thr Pro Pro
225                 230                 235                 240 gtt tat tgt atc gga ccg ctt atc gct agc ggt gat aaa gga aat gtc         768
Val Tyr Cys Ile Gly Pro Leu Ile Ala Ser Gly Asp Lys Gly Asn Val
            245                 250                 255 aat gat gct cat ggg cat gag att tta act tgg tta aac tct caa cct         816
Asn Asp Ala His Gly His Glu Ile Leu Thr Trp Leu Asn Ser Gln Pro
        260                 265                 270 agt aaa agt gtt gtg ttt cta tgc ttt ggt agt tta ggt act ttt aag         864
Ser Lys Ser Val Val Phe Leu Cys Phe Gly Ser Leu Gly Thr Phe Lys
    275                 280                 285 gaa gat cag ttg aag gaa att gct ata ggg ttg gaa aat agt ggc cat         912
Glu Asp Gln Leu Lys Glu Ile Ala Ile Gly Leu Glu Asn Ser Gly His
290                 295                 300 agg ttt tta tgg gta atg aaa agt ccc cct att gat gac aaa acc aag         960
Arg Phe Leu Trp Val Met Lys Ser Pro Pro Ile Asp Asp Lys Thr Lys
305                 310                 315                 320 cgt ttc tta cca cca cca gag cca gat ttt aat gta tta ttg cct gaa        1008
Arg Phe Leu Pro Pro Pro Glu Pro Asp Phe Asn Val Leu Leu Pro Glu
            325                 330                 335 ggt ttt ttg gag aga act aaa gaa aga gga gtt att gtg aag tca tgg        1056
Gly Phe Leu Glu Arg Thr Lys Glu Arg Gly Val Ile Val Lys Ser Trp
        340                 345                 350 gcg cct caa ttg gct ata ttg aat cat gat gca ata ggc gga ttt gtt        1104
Ala Pro Gln Leu Ala Ile Leu Asn His Asp Ala Ile Gly Gly Phe Val
    355                 360                 365 act cat tgc ggt tgg aac tca gtt ttg gaa gct att tgt ggt ggt gtg        1152
Thr His Cys Gly Trp Asn Ser Val Leu Glu Ala Ile Cys Gly Gly Val
370                 375                 380 cca atg tta gca tgg cca tta tat gct gag caa agg gtg aat aga gta        1200
Pro Met Leu Ala Trp Pro Leu Tyr Ala Glu Gln Arg Val Asn Arg Val
385                 390                 395                 400 tgt atg gtg gaa gag atg aag gtg gcg ctg cca ttg gag gag tct gta        1248
Cys Met Val Glu Glu Met Lys Val Ala Leu Pro Leu Glu Glu Ser Val
            405                 410                 415 gat ggg ttt gta atg gca tcg gag att gag aaa aga gtt aag gaa ttg        1296
Asp Gly Phe Val Met Ala Ser Glu Ile Glu Lys Arg Val Lys Glu Leu
        420                 425                 430 gtg gat tat gag agt agt gaa gca att aga gat caa gtt aag ata atg        1344
Val Asp Tyr Glu Ser Ser Glu Ala Ile Arg Asp Gln Val Lys Ile Met
    435                 440                 445 agt gaa aaa gct aaa act gca gtt gca gtt agt gga tca tcc cat gat        1392
Ser Glu Lys Ala Lys Thr Ala Val Ala Val Ser Gly Ser Ser His Asp
450                 455                 460 gca ttg acc aaa cta ctg gat ggt tgg aaa tag                            1425
Ala Leu Thr Lys Leu Leu Asp Gly Trp Lys
465                 470

<210> SEQ ID NO 2
<211> LENGTH: 474
<212> TYPE: PRT
<213> ORGANISM: Nemophila menziesii

<400> SEQUENCE: 2

Met Glu Lys Lys Thr Ile Ile Leu Tyr Pro Ser Pro Gly Ile Gly His
1               5                   10                  15

Leu Val Ser Met Val Glu Leu Ala Lys Leu Ile Leu Asn Arg Glu Pro
            20                  25                  30
```

-continued

```
Ser Tyr Ser Ile Ile Ile Phe Ile Ser Ser Ala Pro Tyr Ser Thr Gly
         35                  40                  45

Ser Ser Ala Pro Tyr Ile Ser His Val Ser Ala Thr Thr Ser Gly Ile
 50                  55                  60

Ser Phe His His Leu Pro Val Leu Val Leu Pro Pro Asn Thr Phe Ser
 65              70                  75                  80

Ser Phe Glu Glu Ile Ala Tyr Lys Ile Pro Gln Leu Asn Asn Pro Asn
                 85                  90                  95

Leu Lys Leu Ala Leu Gln Thr Ile Ser Lys Glu Ser Ser Asp Leu Lys
             100                 105                 110

Ala Phe Ile Ile Asp Phe Phe Cys Thr Ala Ala Val Glu Val Ser Ser
             115                 120                 125

Asn Leu Glu Ile Pro Thr Tyr Phe Phe Phe Thr Ser Gly Ser Ser Ala
 130                 135                 140

Met Cys Gln Phe Leu Tyr Leu Pro Thr Leu His Glu Thr Ile Thr Gln
145                 150                 155                 160

Lys Asp Leu Gln Asp Pro Asn Thr Tyr Val His Ile Pro Gly Ile Pro
                 165                 170                 175

Pro Ile His Ser Leu Asp Leu Pro Lys Val Leu Ser Asn Arg Ser Thr
             180                 185                 190

Val Leu Tyr Lys Glu Leu Ile Asn Thr Ala Asn Gln Met Ala Lys Cys
             195                 200                 205

Ser Gly Ile Leu Ile Asn Ala Phe Glu Thr Leu Glu Pro Lys Ala Val
             210                 215                 220

Lys Ala Leu Lys Glu Gly Leu Cys Thr Pro Gly Met Pro Thr Pro Pro
225                 230                 235                 240

Val Tyr Cys Ile Gly Pro Leu Ile Ala Ser Gly Asp Lys Gly Asn Val
                 245                 250                 255

Asn Asp Ala His Gly His Glu Ile Leu Thr Trp Leu Asn Ser Gln Pro
             260                 265                 270

Ser Lys Ser Val Val Phe Leu Cys Phe Gly Ser Leu Gly Thr Phe Lys
             275                 280                 285

Glu Asp Gln Leu Lys Glu Ile Ala Ile Gly Leu Glu Asn Ser Gly His
290                 295                 300

Arg Phe Leu Trp Val Met Lys Ser Pro Pro Ile Asp Asp Lys Thr Lys
305                 310                 315                 320

Arg Phe Leu Pro Pro Pro Glu Pro Asp Phe Asn Val Leu Leu Pro Glu
                 325                 330                 335

Gly Phe Leu Glu Arg Thr Lys Glu Arg Gly Val Ile Val Lys Ser Trp
             340                 345                 350

Ala Pro Gln Leu Ala Ile Leu Asn His Asp Ala Ile Gly Gly Phe Val
             355                 360                 365

Thr His Cys Gly Trp Asn Ser Val Leu Glu Ala Ile Cys Gly Gly Val
             370                 375                 380

Pro Met Leu Ala Trp Pro Leu Tyr Ala Glu Gln Arg Val Asn Arg Val
385                 390                 395                 400

Cys Met Val Glu Glu Met Lys Val Ala Leu Pro Leu Glu Glu Ser Val
                 405                 410                 415

Asp Gly Phe Val Met Ala Ser Glu Ile Glu Lys Arg Val Lys Glu Leu
             420                 425                 430

Val Asp Tyr Glu Ser Ser Glu Ala Ile Arg Asp Gln Val Lys Ile Met
             435                 440                 445

Ser Glu Lys Ala Lys Thr Ala Val Ala Val Ser Gly Ser Ser His Asp
```

```
                    450                 455                 460
Ala Leu Thr Lys Leu Leu Asp Gly Trp Lys
465                 470

<210> SEQ ID NO 3
<211> LENGTH: 1521
<212> TYPE: DNA
<213> ORGANISM: Viola x wittrockiana
<220> FEATURE:
<221> NAME/KEY: misc_feature
<222> LOCATION: (1)..(1521)
<223> OTHER INFORMATION: complete length Pansy F3'5'H cDNA
<220> FEATURE:
<221> NAME/KEY: CDS
<222> LOCATION: (1)..(1518)

<400> SEQUENCE: 3 atg gca att cta gtc acc gac ttc gtt gtc gcg gct ata att ttc ttg      48
Met Ala Ile Leu Val Thr Asp Phe Val Val Ala Ala Ile Ile Phe Leu
1               5                   10                  15 atc act cgg ttc tta gtt cgt tct ctt ttc aag aaa cca acc cga ccg      96
Ile Thr Arg Phe Leu Val Arg Ser Leu Phe Lys Lys Pro Thr Arg Pro
            20                  25                  30 ctc ccc ccg ggt cct ctc ggt tgg ccc ttg gtg ggc gcc ctc cct ctc     144
Leu Pro Pro Gly Pro Leu Gly Trp Pro Leu Val Gly Ala Leu Pro Leu
        35                  40                  45 cta ggc gcc atg cct cac gtc gca cta gcc aaa ctc gct aag aag tat     192
Leu Gly Ala Met Pro His Val Ala Leu Ala Lys Leu Ala Lys Lys Tyr
    50                  55                  60 ggt ccg atc atg cac cta aaa atg ggc acg tgc gac atg gtg gtc gcg     240
Gly Pro Ile Met His Leu Lys Met Gly Thr Cys Asp Met Val Val Ala
65                  70                  75                  80 tcc acc ccc gag tcg gct cga gcc ttc ctc aaa acg cta gac ctc aac     288
Ser Thr Pro Glu Ser Ala Arg Ala Phe Leu Lys Thr Leu Asp Leu Asn
                85                  90                  95 ttc tcc aac cgc cca ccc aac gcg ggc gca tcc cac cta gcg tac ggc     336
Phe Ser Asn Arg Pro Pro Asn Ala Gly Ala Ser His Leu Ala Tyr Gly
            100                 105                 110 gcg cag gac tta gtc ttc gcc aag tac ggt ccg agg tgg aag act tta     384
Ala Gln Asp Leu Val Phe Ala Lys Tyr Gly Pro Arg Trp Lys Thr Leu
        115                 120                 125 aga aaa ttg agc aac ctc cac atg cta ggc ggg aag gcg ttg gat gat     432
Arg Lys Leu Ser Asn Leu His Met Leu Gly Gly Lys Ala Leu Asp Asp
    130                 135                 140 tgg gca aat gtg agg gtc acc gag cta ggc cac atg ctt aaa gcc atg     480
Trp Ala Asn Val Arg Val Thr Glu Leu Gly His Met Leu Lys Ala Met
145                 150                 155                 160 tgc gag gcg agc cgg tgc ggg gag ccc gtg gtg ctg gcc gag atg ctc     528
Cys Glu Ala Ser Arg Cys Gly Glu Pro Val Val Leu Ala Glu Met Leu
                165                 170                 175 acg tac gcc atg gcg aac atg atc ggt caa gtg ata ctc agc cgg cgc     576
Thr Tyr Ala Met Ala Asn Met Ile Gly Gln Val Ile Leu Ser Arg Arg
            180                 185                 190 gtg ttc gtg acc aaa ggg acc gag tct aac gag ttc aaa gac atg gtg     624
Val Phe Val Thr Lys Gly Thr Glu Ser Asn Glu Phe Lys Asp Met Val
        195                 200                 205 gtc gag ttg atg acg tcc gcc ggg tac ttc aac atc ggt gac ttc ata     672
Val Glu Leu Met Thr Ser Ala Gly Tyr Phe Asn Ile Gly Asp Phe Ile
    210                 215                 220 ccc tcg atc gct tgg atg gat ttg caa ggg atc gag cga ggg atg aag     720
Pro Ser Ile Ala Trp Met Asp Leu Gln Gly Ile Glu Arg Gly Met Lys
225                 230                 235                 240
```

```
aag ctg cac acg aag ttt gat gtg tta ttg acg aag atg gtg aag gag      768
Lys Leu His Thr Lys Phe Asp Val Leu Leu Thr Lys Met Val Lys Glu
            245                 250                 255 cat aga gcg acg agt cat gag cgc aaa ggg aag gca gat ttc ctc gac      816
His Arg Ala Thr Ser His Glu Arg Lys Gly Lys Ala Asp Phe Leu Asp
        260                 265                 270 gtt ctc ttg gaa gaa tgc gac aat aca aat ggg gag aag ctt agt att      864
Val Leu Leu Glu Glu Cys Asp Asn Thr Asn Gly Glu Lys Leu Ser Ile
    275                 280                 285 acc aat atc aaa gct gtc ctt ttg aat cta ttc acg gcg ggc acg gac      912
Thr Asn Ile Lys Ala Val Leu Leu Asn Leu Phe Thr Ala Gly Thr Asp
290                 295                 300 aca tct tcg agc ata atc gaa tgg gcg tta acg gag atg atc aag aat      960
Thr Ser Ser Ser Ile Ile Glu Trp Ala Leu Thr Glu Met Ile Lys Asn
305                 310                 315                 320 ccg acg atc tta aaa aag gcg caa gag gag atg gat cga gtc atc ggt     1008
Pro Thr Ile Leu Lys Lys Ala Gln Glu Glu Met Asp Arg Val Ile Gly
            325                 330                 335 cgt gat cgg agg ctg ctc gaa tcg gac ata tcg agc ctc ccg tac cta     1056
Arg Asp Arg Arg Leu Leu Glu Ser Asp Ile Ser Ser Leu Pro Tyr Leu
        340                 345                 350 caa gcc att gct aaa gaa acg tat cgc aaa cac ccg tcg acg cct ctc     1104
Gln Ala Ile Ala Lys Glu Thr Tyr Arg Lys His Pro Ser Thr Pro Leu
    355                 360                 365 aac ttg ccg agg att gcg atc caa gca tgt gaa gtt gat ggc tac tac     1152
Asn Leu Pro Arg Ile Ala Ile Gln Ala Cys Glu Val Asp Gly Tyr Tyr
370                 375                 380 atc cct aag gac gcg agg ctt agc gtg aac att tgg gcg atc ggt cgg     1200
Ile Pro Lys Asp Ala Arg Leu Ser Val Asn Ile Trp Ala Ile Gly Arg
385                 390                 395                 400 gac ccg aat gtt tgg gag aat ccg ttg gag ttc ttg ccg gaa aga ttc     1248
Asp Pro Asn Val Trp Glu Asn Pro Leu Glu Phe Leu Pro Glu Arg Phe
            405                 410                 415 ttg tct gaa gag aat ggg aag atc aat ccc ggt ggg aat gat ttt gag     1296
Leu Ser Glu Glu Asn Gly Lys Ile Asn Pro Gly Gly Asn Asp Phe Glu
        420                 425                 430 ctg att ccg ttt gga gcc ggg agg aga att tgt gcg ggg aca agg atg     1344
Leu Ile Pro Phe Gly Ala Gly Arg Arg Ile Cys Ala Gly Thr Arg Met
    435                 440                 445 gga atg gtc ctt gta agt tat att ttg ggc act ttg gtc cat tct ttt     1392
Gly Met Val Leu Val Ser Tyr Ile Leu Gly Thr Leu Val His Ser Phe
450                 455                 460 gat tgg aaa tta cca aat ggt gtc gct gag ctt aat atg gat gaa agt     1440
Asp Trp Lys Leu Pro Asn Gly Val Ala Glu Leu Asn Met Asp Glu Ser
465                 470                 475                 480 ttt ggg ctt gca ttg caa aag gcc gtg ccg ctc tcg gcc ttg gtc agc     1488
Phe Gly Leu Ala Leu Gln Lys Ala Val Pro Leu Ser Ala Leu Val Ser
            485                 490                 495 cca cgg ttg gcc tca aac gcg tac gca acc tga                         1521
Pro Arg Leu Ala Ser Asn Ala Tyr Ala Thr
            500                 505
```

<210> SEQ ID NO 4
<211> LENGTH: 506
<212> TYPE: PRT
<213> ORGANISM: Viola x wittrockiana

<400> SEQUENCE: 4

```
Met Ala Ile Leu Val Thr Asp Phe Val Val Ala Ala Ile Ile Phe Leu
1               5                   10                  15
```

-continued

Ile Thr Arg Phe Leu Val Arg Ser Leu Phe Lys Lys Pro Thr Arg Pro
         20                  25                  30

Leu Pro Pro Gly Pro Leu Gly Trp Pro Leu Val Gly Ala Leu Pro Leu
         35                  40                  45

Leu Gly Ala Met Pro His Val Ala Leu Ala Lys Leu Ala Lys Lys Tyr
    50                  55                  60

Gly Pro Ile Met His Leu Lys Met Gly Thr Cys Asp Met Val Val Ala
65                  70                  75                  80

Ser Thr Pro Glu Ser Ala Arg Ala Phe Leu Lys Thr Leu Asp Leu Asn
             85                  90                  95

Phe Ser Asn Arg Pro Pro Asn Ala Gly Ala Ser His Leu Ala Tyr Gly
            100                 105                 110

Ala Gln Asp Leu Val Phe Ala Lys Tyr Gly Pro Arg Trp Lys Thr Leu
        115                 120                 125

Arg Lys Leu Ser Asn Leu His Met Leu Gly Gly Lys Ala Leu Asp Asp
130                 135                 140

Trp Ala Asn Val Arg Val Thr Glu Leu Gly His Met Leu Lys Ala Met
145                 150                 155                 160

Cys Glu Ala Ser Arg Cys Gly Glu Pro Val Val Leu Ala Glu Met Leu
                165                 170                 175

Thr Tyr Ala Met Ala Asn Met Ile Gly Gln Val Ile Leu Ser Arg Arg
            180                 185                 190

Val Phe Val Thr Lys Gly Thr Glu Ser Asn Glu Phe Lys Asp Met Val
        195                 200                 205

Val Glu Leu Met Thr Ser Ala Gly Tyr Phe Asn Ile Gly Asp Phe Ile
        210                 215                 220

Pro Ser Ile Ala Trp Met Asp Leu Gln Gly Ile Glu Arg Gly Met Lys
225                 230                 235                 240

Lys Leu His Thr Lys Phe Asp Val Leu Leu Thr Lys Met Val Lys Glu
                245                 250                 255

His Arg Ala Thr Ser His Glu Arg Lys Gly Lys Ala Asp Phe Leu Asp
            260                 265                 270

Val Leu Leu Glu Glu Cys Asp Asn Thr Asn Gly Glu Lys Leu Ser Ile
        275                 280                 285

Thr Asn Ile Lys Ala Val Leu Leu Asn Leu Phe Thr Ala Gly Thr Asp
    290                 295                 300

Thr Ser Ser Ser Ile Ile Glu Trp Ala Leu Thr Glu Met Ile Lys Asn
305                 310                 315                 320

Pro Thr Ile Leu Lys Lys Ala Gln Glu Glu Met Asp Arg Val Ile Gly
                325                 330                 335

Arg Asp Arg Arg Leu Leu Glu Ser Asp Ile Ser Ser Leu Pro Tyr Leu
            340                 345                 350

Gln Ala Ile Ala Lys Glu Thr Tyr Arg Lys His Pro Ser Thr Pro Leu
        355                 360                 365

Asn Leu Pro Arg Ile Ala Ile Gln Ala Cys Glu Val Asp Gly Tyr Tyr
    370                 375                 380

Ile Pro Lys Asp Ala Arg Leu Ser Val Asn Ile Trp Ala Ile Gly Arg
385                 390                 395                 400

Asp Pro Asn Val Trp Glu Asn Pro Leu Glu Phe Leu Pro Glu Arg Phe
                405                 410                 415

Leu Ser Glu Glu Asn Gly Lys Ile Asn Pro Gly Gly Asn Asp Phe Glu
            420                 425                 430

-continued

```
Leu Ile Pro Phe Gly Ala Gly Arg Ile Cys Ala Gly Thr Arg Met
        435                 440                 445

Gly Met Val Leu Val Ser Tyr Ile Leu Gly Thr Leu Val His Ser Phe
450                 455                 460

Asp Trp Lys Leu Pro Asn Gly Val Ala Glu Leu Asn Met Asp Glu Ser
465                 470                 475                 480

Phe Gly Leu Ala Leu Gln Lys Ala Val Pro Leu Ser Ala Leu Val Ser
                485                 490                 495

Pro Arg Leu Ala Ser Asn Ala Tyr Ala Thr
            500                 505

<210> SEQ ID NO 5
<211> LENGTH: 1539
<212> TYPE: DNA
<213> ORGANISM: Torenia fournier
<220> FEATURE:
<221> NAME/KEY: misc_feature
<222> LOCATION: (1)..(1539)
<223> OTHER INFORMATION: complete length Trenia FNS
<220> FEATURE:
<221> NAME/KEY: CDS
<222> LOCATION: (1)..(1536)

<400> SEQUENCE: 5 atg gac aca gtc tta atc aca ctc tac acc gcc ctg ttc gtc atc acc     48
Met Asp Thr Val Leu Ile Thr Leu Tyr Thr Ala Leu Phe Val Ile Thr
1               5                   10                  15 acc acc ttc ctc ctc ctc ctc cgc cga agg gga cca ccg tct ccg ccc     96
Thr Thr Phe Leu Leu Leu Leu Arg Arg Arg Gly Pro Pro Ser Pro Pro
                20                  25                  30 ggt cct ctc tcc cta ccc ata att ggc cac ctc cac ctc ctc ggc cca    144
Gly Pro Leu Ser Leu Pro Ile Ile Gly His Leu His Leu Leu Gly Pro
            35                  40                  45 aga ctc cac cac acg ttc cat gaa ttc tca ctc aaa tac ggc cca ttg    192
Arg Leu His His Thr Phe His Glu Phe Ser Leu Lys Tyr Gly Pro Leu
    50                  55                  60 atc cag ctc aag ctc ggc tcg atc ccg tgc gtc gtg gcc tcg acg ccc    240
Ile Gln Leu Lys Leu Gly Ser Ile Pro Cys Val Val Ala Ser Thr Pro
65                  70                  75                  80 gag ctc gcg aga gag ttt ctt aag acg aac gag ctc gcg ttc tcc tct    288
Glu Leu Ala Arg Glu Phe Leu Lys Thr Asn Glu Leu Ala Phe Ser Ser
                85                  90                  95 cgc aag cac tct acg gcc ata gac atc gtc acc tac gac tcg tcc ttt    336
Arg Lys His Ser Thr Ala Ile Asp Ile Val Thr Tyr Asp Ser Ser Phe
                100                 105                 110 gct ttc tct ccg tac gga ccc tac tgg aag tac atc aag aaa ctg tgt    384
Ala Phe Ser Pro Tyr Gly Pro Tyr Trp Lys Tyr Ile Lys Lys Leu Cys
            115                 120                 125 acc tac gag ctg ctc gga gcg agg aac ctc gga cac ttt cag ccc att    432
Thr Tyr Glu Leu Leu Gly Ala Arg Asn Leu Gly His Phe Gln Pro Ile
130                 135                 140 agg aat ctc gag gtc agg tcc ttt ctg cag ctt ctg atg cac aag agc    480
Arg Asn Leu Glu Val Arg Ser Phe Leu Gln Leu Leu Met His Lys Ser
145                 150                 155                 160 ttt aag ggc gag agt gtg aat gtg aca gac gag ctg gtg agg ctg acg    528
Phe Lys Gly Glu Ser Val Asn Val Thr Asp Glu Leu Val Arg Leu Thr
                165                 170                 175 agc aat gtg ata tcc cac atg atg ctg agc ata agg tgc tcg gaa gat    576
Ser Asn Val Ile Ser His Met Met Leu Ser Ile Arg Cys Ser Glu Asp
                180                 185                 190 gaa ggc gat gct gag gcg gcg aga aca gtg ata cgc gag gtg acg cag    624
```

```
                Glu Gly Asp Ala Glu Ala Ala Arg Thr Val Ile Arg Glu Val Thr Gln
                            195                 200                 205 ata ttt ggg gaa ttc gat gtt acg gac ata ata tgg ttt tgc aag aaa        672
Ile Phe Gly Glu Phe Asp Val Thr Asp Ile Ile Trp Phe Cys Lys Lys
210                 215                 220 ttc gat ctg cag ggg ata aag aag agg tca gag gat att cag agg agg        720
Phe Asp Leu Gln Gly Ile Lys Lys Arg Ser Glu Asp Ile Gln Arg Arg
225                 230                 235                 240 tat gat gct ttg ctc gag aag att att agt gat aga gag aga tcg agg        768
Tyr Asp Ala Leu Leu Glu Lys Ile Ile Ser Asp Arg Glu Arg Ser Arg
                245                 250                 255 agg caa aat cgt gat aag cat ggt ggc ggt aac aat gag gag gcc aag        816
Arg Gln Asn Arg Asp Lys His Gly Gly Gly Asn Asn Glu Glu Ala Lys
            260                 265                 270 gat ttt ctt gat atg ttg ctt gat gtg atg gag agt ggg gac acg gag        864
Asp Phe Leu Asp Met Leu Leu Asp Val Met Glu Ser Gly Asp Thr Glu
        275                 280                 285 gtc aaa ttc act aga gag cat ctc aag gct ttg att ctg gat ttc ttc        912
Val Lys Phe Thr Arg Glu His Leu Lys Ala Leu Ile Leu Asp Phe Phe
    290                 295                 300 acg gcc ggt acg gac aca aca gcc ata gcc acc gag tgg gcc atc gcc        960
Thr Ala Gly Thr Asp Thr Thr Ala Ile Ala Thr Glu Trp Ala Ile Ala
305                 310                 315                 320 gag ctc atc aac aac ccg aac gtc ttg aag aag gcc caa gaa gaa ata       1008
Glu Leu Ile Asn Asn Pro Asn Val Leu Lys Lys Ala Gln Glu Glu Ile
                325                 330                 335 tcc cgg atc atc gga acc aag cgg atc gta caa gaa tcc gac gcc cca       1056
Ser Arg Ile Ile Gly Thr Lys Arg Ile Val Gln Glu Ser Asp Ala Pro
            340                 345                 350 gac cta ccc tac ctc cag gcc atc atc aag gag acg ttc cgg ctc cac       1104
Asp Leu Pro Tyr Leu Gln Ala Ile Ile Lys Glu Thr Phe Arg Leu His
        355                 360                 365 cca ccg atc ccg atg ctc tcg cgt aag tcc acc tcc gat tgc acg gtc       1152
Pro Pro Ile Pro Met Leu Ser Arg Lys Ser Thr Ser Asp Cys Thr Val
    370                 375                 380 aac ggc tac aaa atc caa gcc aag agc ctc ttg ttc gtg aac ata tgg       1200
Asn Gly Tyr Lys Ile Gln Ala Lys Ser Leu Leu Phe Val Asn Ile Trp
385                 390                 395                 400 tcc atc ggt cga aac cct aat tac tgg gaa agc cct atg gag ttc agg       1248
Ser Ile Gly Arg Asn Pro Asn Tyr Trp Glu Ser Pro Met Glu Phe Arg
                405                 410                 415 ccc gag cgg ttc ttg gag aag gga cgc gag tcc atc gac gtc aag ggc       1296
Pro Glu Arg Phe Leu Glu Lys Gly Arg Glu Ser Ile Asp Val Lys Gly
            420                 425                 430 cag cac ttt gag ctc ttg cct ttt ggg acg ggc cgc agg ggc tgt ccc       1344
Gln His Phe Glu Leu Leu Pro Phe Gly Thr Gly Arg Arg Gly Cys Pro
        435                 440                 445 ggt atg ttg ctg gct ata caa gag gtg gtc agc atc att ggg acc atg       1392
Gly Met Leu Leu Ala Ile Gln Glu Val Val Ser Ile Ile Gly Thr Met
    450                 455                 460 gtt cag tgc ttc gac tgg aaa ttg gca gat ggt tcg ggc aat aat gtg       1440
Val Gln Cys Phe Asp Trp Lys Leu Ala Asp Gly Ser Gly Asn Asn Val
465                 470                 475                 480 gac atg acc gaa cgg tct gga ttg acc gct ccg aga gcg ttc gat ctg       1488
Asp Met Thr Glu Arg Ser Gly Leu Thr Ala Pro Arg Ala Phe Asp Leu
                485                 490                 495 gtt tgc cgg ttg tat cca cgg gtt gac ccg gcc aca ata tcg ggt gct       1536
Val Cys Arg Leu Tyr Pro Arg Val Asp Pro Ala Thr Ile Ser Gly Ala
            500                 505                 510
``` tga                                                                1539

<210> SEQ ID NO 6
<211> LENGTH: 512
<212> TYPE: PRT
<213> ORGANISM: Torenia fournier

<400> SEQUENCE: 6

Met Asp Thr Val Leu Ile Thr Leu Tyr Thr Ala Leu Phe Val Ile Thr
1               5                   10                  15

Thr Thr Phe Leu Leu Leu Arg Arg Arg Gly Pro Pro Ser Pro Pro Pro
            20                  25                  30

Gly Pro Leu Ser Leu Pro Ile Ile Gly His Leu His Leu Leu Gly Pro
        35                  40                  45

Arg Leu His His Thr Phe His Glu Phe Ser Leu Lys Tyr Gly Pro Leu
    50                  55                  60

Ile Gln Leu Lys Leu Gly Ser Ile Pro Cys Val Val Ala Ser Thr Pro
65                  70                  75                  80

Glu Leu Ala Arg Glu Phe Leu Lys Thr Asn Glu Leu Ala Phe Ser Ser
                85                  90                  95

Arg Lys His Ser Thr Ala Ile Asp Ile Val Thr Tyr Asp Ser Ser Phe
            100                 105                 110

Ala Phe Ser Pro Tyr Gly Pro Tyr Trp Lys Tyr Ile Lys Lys Leu Cys
        115                 120                 125

Thr Tyr Glu Leu Leu Gly Ala Arg Asn Leu Gly His Phe Gln Pro Ile
    130                 135                 140

Arg Asn Leu Glu Val Arg Ser Phe Leu Gln Leu Leu Met His Lys Ser
145                 150                 155                 160

Phe Lys Gly Glu Ser Val Asn Val Thr Asp Glu Leu Val Arg Leu Thr
                165                 170                 175

Ser Asn Val Ile Ser His Met Met Leu Ser Ile Arg Cys Ser Glu Asp
            180                 185                 190

Glu Gly Asp Ala Glu Ala Ala Arg Thr Val Ile Arg Glu Val Thr Gln
        195                 200                 205

Ile Phe Gly Glu Phe Asp Val Thr Asp Ile Ile Trp Phe Cys Lys Lys
    210                 215                 220

Phe Asp Leu Gln Gly Ile Lys Lys Arg Ser Glu Asp Ile Gln Arg Arg
225                 230                 235                 240

Tyr Asp Ala Leu Leu Glu Lys Ile Ile Ser Asp Arg Glu Arg Ser Arg
                245                 250                 255

Arg Gln Asn Arg Asp Lys His Gly Gly Asn Glu Glu Ala Lys
            260                 265                 270

Asp Phe Leu Asp Met Leu Leu Asp Val Met Glu Ser Gly Asp Thr Glu
    275                 280                 285

Val Lys Phe Thr Arg Glu His Leu Lys Ala Leu Ile Leu Asp Phe Phe
290                 295                 300

Thr Ala Gly Thr Asp Thr Thr Ala Ile Ala Thr Glu Trp Ala Ile Ala
305                 310                 315                 320

Glu Leu Ile Asn Asn Pro Asn Val Leu Lys Lys Ala Gln Glu Ile
                325                 330                 335

Ser Arg Ile Ile Gly Thr Lys Arg Ile Val Gln Glu Ser Asp Ala Pro
            340                 345                 350

Asp Leu Pro Tyr Leu Gln Ala Ile Ile Lys Glu Thr Phe Arg Leu His
    355                 360                 365

```
Pro Pro Ile Pro Met Leu Ser Arg Lys Ser Thr Ser Asp Cys Thr Val
            370                 375                 380

Asn Gly Tyr Lys Ile Gln Ala Lys Ser Leu Leu Phe Val Asn Ile Trp
385                 390                 395                 400

Ser Ile Gly Arg Asn Pro Asn Tyr Trp Glu Ser Pro Met Glu Phe Arg
                405                 410                 415

Pro Glu Arg Phe Leu Lys Gly Arg Glu Ser Ile Asp Val Lys Gly
            420                 425                 430

Gln His Phe Glu Leu Leu Pro Phe Gly Thr Gly Arg Arg Gly Cys Pro
            435                 440                 445

Gly Met Leu Leu Ala Ile Gln Glu Val Val Ser Ile Ile Gly Thr Met
    450                 455                 460

Val Gln Cys Phe Asp Trp Lys Leu Ala Asp Gly Ser Gly Asn Asn Val
465                 470                 475                 480

Asp Met Thr Glu Arg Ser Gly Leu Thr Ala Pro Arg Ala Phe Asp Leu
                485                 490                 495

Val Cys Arg Leu Tyr Pro Arg Val Asp Pro Ala Thr Ile Ser Gly Ala
            500                 505                 510

<210> SEQ ID NO 7
<211> LENGTH: 4087
<212> TYPE: DNA
<213> ORGANISM: Perilla frutescens
<220> FEATURE:
<221> NAME/KEY: gene
<222> LOCATION: (1)..(4087)
<223> OTHER INFORMATION: Perilla 3AT

<400> SEQUENCE: 7
aactattatg atcccacaga gtttttgaca gatgagtctt caggaggaga tgctgaacct      60
tttcactact ctactgaacg catcacaagt ttatcggctt atatgactaa tagggatcaa     120
cttcacaaca gagaggctca tagagctctt aaagaggatt tgatcgagca catatggaaa     180
aaattcggca ctaactaaat atataattta cgttttatgc actcgtaatt taaaatttca     240
tgtgtctcat tgtagtttat ttaattatgt tttcactctt gtaattttta ttttgttgtg     300
aagtaaatta tgaatttata attatatggg taatttttg ataattatgc aattaaaaat     360
aattaatatt tttaaatgc aagagaaaaa tgttatttta ataacatgtt cttattaaaa     420
aataaaatga taaatatttt atgtaggttg ggagaaaatg aaaaaataat atttatttg     480
aaggttgggt tggatgaggt cactgatggg agtataaata atactccctc cgtcccataa     540
ttattgtcca ttattccttt tgggatgtc ccaaaattat agtcctattc taaattggga     600
ttgtatttaa atattctttt acaaatataa ccctatttga tatagtatga atgcaattaa     660
tatagtaaaa aaataagggc aatataggat aattattgta aattgtatat ttccaataca     720
tattaaatgt gatttcttaa tctgtgtgaa aataggaagt ggactataat tatgggacgg     780
agggagtata aagttggagg ttgtggatgt ggaggagaaa gaaattaata ttttatttaa     840
agattggatt aaaggaggtc actgatgtgg gtagtcttag aggaaatgta gtcttagagg     900
aaatctgccc agcaaaataa aataataagt aaataaataa actaaatatg tattgaatgc     960
gacatctagc aatatagcca catatatagt gcagtagcac gcagcgctcg ttactcgtca    1020
gtcgtcaaag aatggtaagt atagaaaagc atctttaaat aacacaccaa aaaccacagc    1080
tacgttcaac accgccatga ccaccaccgt gatcgaaacg tgtagagttg gccaccgcc     1140
ggactcggtg gcggagcaat cgttgccgct cacattcttc gacatgacgt ggctgcattt    1200
```

```
tcatcccatg cttcagctcc tcttctacga attcccttgt tccaagcaac atttctcaga   1260
atccatcatt ccaaaactca aacaatctct ctctaaaact ctcatacact tcttccctct   1320
ctcatgcaat ttaatctacc cttcatctcc ggagaaaatg cccgagtttc ggtatctatc   1380
gggggactcg gtttctttca ctatcgcaga atctagcgac gacttcgatg atctcgtcgg   1440
aaatcgcgca gaatctcccg ttaggctcta caacttcgtc cctaaattgc cgcagattgt   1500
cgaagaatct gatagaaaac tcttccaagt tttcgccgtg caggtgactc ttttcccagg   1560
tcgaggcgtc ggtattggaa tagcaacgca tcacaccgtt agcgatgccc cgtcgtttct   1620
cgcctttata acggcttggg cttggatgag caaacacatt gaagatgaag atgaagagtt   1680
taaatctttg ccagttttcg atagatccgt cataaaatat ccgacgaaat ttgactcgat   1740
ttattggaaa aaggcgctaa aatttccttt gcaatctcgt catccctcat taccgacgga   1800
ccgcattcga accacgttcg ttttcaccca atccgaaatt aagaaattga agggttcgat   1860
tcagtccaga gttccaagtt tagtccatct ctcatctttt gtagcgattg cagcttatat   1920
gtgggctggc gtaacgaaat cactcacagc agatgaagac cacgacgacg gggatgcatt   1980
tttcttgatt ccgtcgatc taaggccacg attagatccg ccagttcccg aaaattactt   2040
cgggaactgc ttatcgtacg cgctgccgag aatgcggcgg cgagagctgg tgggagagaa   2100
agggtgttt ctggcggctg aggcaatcgc ggcggagatc aaaaaaagga tcaacgacaa   2160
gagaatatta gaaacggtgg agaaatggtc gctggagatt cgtgaagcgt tgcagaaatc   2220
atatttttcg gtggcaggat cgagcaagct agatctttac ggtgcagatt ttggatgggg   2280
gaaggcgaga aagcaagaaa tattgtcgat tgatggggag aaatatgcaa tgacgctttg   2340
taaagccagg gatttcgaag gaggattgga ggtttgcttg tctttgccta aggacaaaat   2400
ggatgctttt gctgcttatt tttcagcggg aattaatggt taataaatgt atgtaattaa   2460
actaatatta ttatgtaaca attaattaag tgttgagtaa cgtgaagaat aatatctttt   2520
acctattata tatttatgag ttggttcaaa taaaatcact tcatttattg tattaaccgt   2580
ttagtgttct tctcaccata ttttggtgct atttttttaaa aaatgttttt tttattgtat   2640
tttagtatta attgttttac cactaaaatt acagtaaaat gcaagatagt ttaatttta    2700
catttacata tgaaacacat tctctttata accaacctct ctatatatat aatatgtgtg   2760
tatgtatgta tacacatgta tgaatactag aaatatatct taaaccatcc atccttcaaa   2820
aatttcgggg ccatattgca tggtgacatt ataatatttg ataatttctt cgaacacgtt   2880
attaattcaa tttaataatt ctaataaaaa gacgctcaga caatatatgt agataggatc   2940
ggcccaaagg ggtgtctggg tgggctgtcg cccatgggcc ccgaaatctt aggggcaaaa   3000
aaaaaaaaat tcattatacc tagggcaaaa aaattaccgc tcttcacttc tctgcctctc   3060
tccctcatcc ctcgttcctc ctctctcttc cctatgtacg cctcttcac tccctccccc    3120
tctctcagtt ctctatcact tgtatttgt attgaaaact tgttgaaaac taaaccaaaa    3180
atagaaaaag gtatagaaaa tttgaaaaca aaggttgttt ttttgtgttg ctgcagttcc   3240
caaacttgcc gagttgccga cttgccgtgt tgaattgtta tatatgttaa aagcctaaaa   3300
tatatccttt cagaattgag atggattgtt gtaactatca ggttttttt attgagaatt    3360
ttagatcaat tagttatctt gtaatttttt attctttta atacaatact ccctccatcc    3420
caatagcaag gtccccttgc tattgggcac gggtattaag gaggaggatt attataatga   3480
aaattaatat aaagtaagtg gattccactt tattaaggaa tattataatc aaaagtaata   3540
taaagtaagt ggattccact ttaattagga cactaattat tttctttttt ggtatgagac   3600
```

-continued

```
tttgctattg ggacatccca aaaaggcaaa agagaccttg ctattaggac ggtggacgtg    3660
ctgccgaggc acgcaaatta atttaccttt cctcttctat actaactcgt agtagcggcg    3720
agtaaaggtc gaaccctcaa ggagcaattg aactagatgt gctattagaa ataaaataaa    3780
cacaagtgag aggggagttt ttggtttcaa tttaactaaa actaattatg aaaatgaaaa    3840
aacaaatata aaacataaac aggtagacga aatatgataa agatagaatt ctagttctcg    3900
gttcagttat caccttttctc caagtatttc atgaataatg caacgcctct tttcatacaa    3960
cttagaatcg atgtccaaag gttaatatca agctttattt acctaattgt ctcgtacgat    4020
tagttaacta aaacaagctc tttaattaac tctactcaat tagataacct agaataagct    4080
ctctaga                                                              4087
```

```
<210> SEQ ID NO 8
<211> LENGTH: 1356
<212> TYPE: DNA
<213> ORGANISM: Lavender officinallis
<220> FEATURE:
<221> NAME/KEY: misc_feature
<222> LOCATION: (1)..(1356)
<223> OTHER INFORMATION: Lavender 3AT
<220> FEATURE:
<221> NAME/KEY: CDS
<222> LOCATION: (1)..(1353)

<400> SEQUENCE: 8
```

```
atg acc acc ctc ctc gaa tcc tcc cga gtg gcg ccg cct cca ggc acg        48
Met Thr Thr Leu Leu Glu Ser Ser Arg Val Ala Pro Pro Pro Gly Thr
1               5                   10                  15 gtg gct gag cag tca ctc ccg ctc acc ttc ttc gac atg acg tgg ctg        96
Val Ala Glu Gln Ser Leu Pro Leu Thr Phe Phe Asp Met Thr Trp Leu
            20                  25                  30 cat ttc cac ccc atg ctt cag ctt ctc ttc tac gaa ctc ccc tgt tcc       144
His Phe His Pro Met Leu Gln Leu Leu Phe Tyr Glu Leu Pro Cys Ser
        35                  40                  45 aaa ccc gcc ttc ctc gaa acc gtc gtt ccg aaa ctc aaa caa tcc tta       192
Lys Pro Ala Phe Leu Glu Thr Val Val Pro Lys Leu Lys Gln Ser Leu
    50                  55                  60 tct cta acc ctc aaa cac ttc ttc ccc ctt tca tgc aat cta atc tac       240
Ser Leu Thr Leu Lys His Phe Phe Pro Leu Ser Cys Asn Leu Ile Tyr
65                  70                  75                  80 cct cta tcg ccg gag aaa atg ccg gag ttc cgg tat cag aac ggt gac       288
Pro Leu Ser Pro Glu Lys Met Pro Glu Phe Arg Tyr Gln Asn Gly Asp
                85                  90                  95 tcg gtt tct ttc acg att atg gag tct agc gac gat tat gaa gat ctc       336
Ser Val Ser Phe Thr Ile Met Glu Ser Ser Asp Asp Tyr Glu Asp Leu
            100                 105                 110 gtc gga gat cat ccg cat tcc gct cat aaa tac tac tgc ttt gcc cct       384
Val Gly Asp His Pro His Ser Ala His Lys Tyr Tyr Cys Phe Ala Pro
        115                 120                 125 cag ctg ccg ccg ata gtc gag gaa tct gat cgg aaa ttg ttt caa gtt       432
Gln Leu Pro Pro Ile Val Glu Glu Ser Asp Arg Lys Leu Phe Gln Val
    130                 135                 140 tta gcc gtg caa gtg act ctg ttt ccc ggt cgc ggg gtg tgc atc gga       480
Leu Ala Val Gln Val Thr Leu Phe Pro Gly Arg Gly Val Cys Ile Gly
145                 150                 155                 160 ata acg acg cac cac acc gtt agc gat gct cca tcg ttt gta ggg ttt       528
Ile Thr Thr His His Thr Val Ser Asp Ala Pro Ser Phe Val Gly Phe
                165                 170                 175 atg aag agt tgg gct tcc atc act aaa ttc gga gga gat gat gaa ttc       576
Met Lys Ser Trp Ala Ser Ile Thr Lys Phe Gly Gly Asp Asp Glu Phe
```

```
              Met Lys Ser Trp Ala Ser Ile Thr Lys Phe Gly Gly Asp Glu Phe
                          180                 185                 190 ttg gac gga aaa ggt gaa tgt ttg ccg gtt ttc gac cga tcg ctc gtg         624
Leu Asp Gly Lys Gly Glu Cys Leu Pro Val Phe Asp Arg Ser Leu Val
            195                 200                 205 aat tat ccg cct aaa ttg gac aca tat tta tgg aac aac gcg cag aaa         672
Asn Tyr Pro Pro Lys Leu Asp Thr Tyr Leu Trp Asn Asn Ala Gln Lys
        210                 215                 220 cgt ccg ttg gaa tcg cag cat cca tct tta ccg acg gat cgg att cga         720
Arg Pro Leu Glu Ser Gln His Pro Ser Leu Pro Thr Asp Arg Ile Arg
225                 230                 235                 240 gct acc tac ctt ttc acc caa tct gaa att aag aaa ttg aag ggt ttg         768
Ala Thr Tyr Leu Phe Thr Gln Ser Glu Ile Lys Lys Leu Lys Gly Leu
                245                 250                 255 att cag aga aaa gcc cca aat gta gtt aat ctc tct tcc ttc gtc gcg         816
Ile Gln Arg Lys Ala Pro Asn Val Val Asn Leu Ser Ser Phe Val Ala
            260                 265                 270 atc gca gct tat atc tgg acc ggc atc gcc aaa tcg gtc gga gat tac         864
Ile Ala Ala Tyr Ile Trp Thr Gly Ile Ala Lys Ser Val Gly Asp Tyr
        275                 280                 285 aaa gac gtg gat gac gac aaa cgc gct ttc ttt tta att ccg atc gat         912
Lys Asp Val Asp Asp Asp Lys Arg Ala Phe Phe Leu Ile Pro Ile Asp
290                 295                 300 tta agg ccg cgt ttg gat ccg ccg gct ccg ggg aac tac ttc gga aac         960
Leu Arg Pro Arg Leu Asp Pro Pro Ala Pro Gly Asn Tyr Phe Gly Asn
305                 310                 315                 320 tgt cta tcg ttt gcg atg gcg aag atc ctg cgg cgg gat ttg gtc gga        1008
Cys Leu Ser Phe Ala Met Ala Lys Ile Leu Arg Arg Asp Leu Val Gly
                325                 330                 335 gat gaa ggg gtg ttt cgg gca gct gag gcg atc gcg gcg gaa ata gag        1056
Asp Glu Gly Val Phe Arg Ala Ala Glu Ala Ile Ala Ala Glu Ile Glu
            340                 345                 350 aag agg acg agc gac aag aag att cta gaa act gtg gag aac tgg ccg        1104
Lys Arg Thr Ser Asp Lys Lys Ile Leu Glu Thr Val Glu Asn Trp Pro
        355                 360                 365 tct gag att cgc gaa gcc ttg caa aac tgt tat ttc tcg gtg gcg gga        1152
Ser Glu Ile Arg Glu Ala Leu Gln Asn Cys Tyr Phe Ser Val Ala Gly
370                 375                 380 tcg agc agg ctt gat ctt tac ggc gcg gat ttt gga tgg ggt aag gcg        1200
Ser Ser Arg Leu Asp Leu Tyr Gly Ala Asp Phe Gly Trp Gly Lys Ala
385                 390                 395                 400 gtg aag caa gag ata ctg tcg att gat gga gag aag ttt acg atg tcg        1248
Val Lys Gln Glu Ile Leu Ser Ile Asp Gly Glu Lys Phe Thr Met Ser
                405                 410                 415 ttg tgt aaa ccg agg gat gct gcc gga gga ttg gag gtt gga ttg tct        1296
Leu Cys Lys Pro Arg Asp Ala Ala Gly Gly Leu Glu Val Gly Leu Ser
            420                 425                 430 ttg cca aag gag gaa ttg caa gct ttt gat gat tat ttt gcg gag gga        1344
Leu Pro Lys Glu Glu Leu Gln Ala Phe Asp Asp Tyr Phe Ala Glu Gly
        435                 440                 445 ata aag ggt tga                                                         1356
Ile Lys Gly
    450

<210> SEQ ID NO 9
<211> LENGTH: 451
<212> TYPE: PRT
<213> ORGANISM: Lavender officinallis

<400> SEQUENCE: 9
```

```
Met Thr Thr Leu Leu Glu Ser Ser Arg Val Ala Pro Pro Gly Thr
1               5                   10                  15

Val Ala Glu Gln Ser Leu Pro Leu Thr Phe Phe Asp Met Thr Trp Leu
            20                  25                  30

His Phe His Pro Met Leu Gln Leu Leu Phe Tyr Glu Leu Pro Cys Ser
        35                  40                  45

Lys Pro Ala Phe Leu Glu Thr Val Pro Lys Leu Lys Gln Ser Leu
50                      55                  60

Ser Leu Thr Leu Lys His Phe Phe Pro Leu Ser Cys Asn Leu Ile Tyr
65                  70                  75                  80

Pro Leu Ser Pro Glu Lys Met Pro Glu Phe Arg Tyr Gln Asn Gly Asp
                85                  90                  95

Ser Val Ser Phe Thr Ile Met Glu Ser Ser Asp Asp Tyr Glu Asp Leu
                100                 105                 110

Val Gly Asp His Pro His Ser Ala His Lys Tyr Tyr Cys Phe Ala Pro
            115                 120                 125

Gln Leu Pro Pro Ile Val Glu Glu Ser Asp Arg Lys Leu Phe Gln Val
        130                 135                 140

Leu Ala Val Gln Val Thr Leu Phe Pro Gly Arg Gly Val Cys Ile Gly
145                 150                 155                 160

Ile Thr Thr His His Thr Val Ser Asp Ala Pro Ser Phe Val Gly Phe
                165                 170                 175

Met Lys Ser Trp Ala Ser Ile Thr Lys Phe Gly Gly Asp Asp Glu Phe
            180                 185                 190

Leu Asp Gly Lys Gly Glu Cys Leu Pro Val Phe Asp Arg Ser Leu Val
        195                 200                 205

Asn Tyr Pro Pro Lys Leu Asp Thr Tyr Leu Trp Asn Asn Ala Gln Lys
    210                 215                 220

Arg Pro Leu Glu Ser Gln His Pro Ser Leu Pro Thr Asp Arg Ile Arg
225                 230                 235                 240

Ala Thr Tyr Leu Phe Thr Gln Ser Glu Ile Lys Lys Leu Lys Gly Leu
            245                 250                 255

Ile Gln Arg Lys Ala Pro Asn Val Val Asn Leu Ser Ser Phe Val Ala
        260                 265                 270

Ile Ala Ala Tyr Ile Trp Thr Gly Ile Ala Lys Ser Val Gly Asp Tyr
    275                 280                 285

Lys Asp Val Asp Asp Lys Arg Ala Phe Phe Leu Ile Pro Ile Asp
290                 295                 300

Leu Arg Pro Arg Leu Asp Pro Pro Ala Pro Gly Asn Tyr Phe Gly Asn
305                 310                 315                 320

Cys Leu Ser Phe Ala Met Ala Lys Ile Leu Arg Arg Asp Leu Val Gly
            325                 330                 335

Asp Glu Gly Val Phe Arg Ala Ala Glu Ala Ile Ala Ala Glu Ile Glu
        340                 345                 350

Lys Arg Thr Ser Asp Lys Lys Ile Leu Glu Thr Val Glu Asn Trp Pro
    355                 360                 365

Ser Glu Ile Arg Glu Ala Leu Gln Asn Cys Tyr Phe Ser Val Ala Gly
370                 375                 380

Ser Ser Arg Leu Asp Leu Tyr Gly Ala Asp Phe Gly Trp Gly Lys Ala
385                 390                 395                 400

Val Lys Gln Glu Ile Leu Ser Ile Asp Gly Glu Lys Phe Thr Met Ser
            405                 410                 415

Leu Cys Lys Pro Arg Asp Ala Ala Gly Gly Leu Glu Val Gly Leu Ser
```

```
                       420                 425                 430
Leu Pro Lys Glu Glu Leu Gln Ala Phe Asp Asp Tyr Phe Ala Glu Gly
                435                 440                 445

Ile Lys Gly
        450

<210> SEQ ID NO 10
<211> LENGTH: 1395
<212> TYPE: DNA
<213> ORGANISM: Nemophila menziesii
<220> FEATURE:
<221> NAME/KEY: misc_feature
<222> LOCATION: (1)..(1395)
<223> OTHER INFORMATION: NmGT3
<220> FEATURE:
<221> NAME/KEY: CDS
<222> LOCATION: (1)..(1392)

<400> SEQUENCE: 10 atg cca tca atc ctg agc aat agc gca cac att cta ctc ttt cca ttt     48
Met Pro Ser Ile Leu Ser Asn Ser Ala His Ile Leu Leu Phe Pro Phe
1               5                   10                  15 cct act tca gga cat att ata ccc atc ctt gat ctt gcc aac caa tta     96
Pro Thr Ser Gly His Ile Ile Pro Ile Leu Asp Leu Ala Asn Gln Leu
            20                  25                  30 ctt gcc cgt ggc tta acc atc acc atc tta atc aca ccc gca aac cta    144
Leu Ala Arg Gly Leu Thr Ile Thr Ile Leu Ile Thr Pro Ala Asn Leu
        35                  40                  45 act ctt ctc tcc aca cag ttg ata gag ctc gac cgt ctt ggt tcc cta    192
Thr Leu Leu Ser Thr Gln Leu Ile Glu Leu Asp Arg Leu Gly Ser Leu
    50                  55                  60 cat act ttg gtc ctt cct ttt cca aac ccc ccc aac cct tca gag act    240
His Thr Leu Val Leu Pro Phe Pro Asn Pro Pro Asn Pro Ser Glu Thr
65                  70                  75                  80 agt ttg gct gca aga gtt cat gct agt agt caa cta tca aac acc atc    288
Ser Leu Ala Ala Arg Val His Ala Ser Ser Gln Leu Ser Asn Thr Ile
                85                  90                  95 ata caa tgg ttc caa tct cac aca tca ccc cct gtt gcc att gtt tct    336
Ile Gln Trp Phe Gln Ser His Thr Ser Pro Pro Val Ala Ile Val Ser
            100                 105                 110 gat ttt ttc ctt ggc tgg act aac agc tta gca tca caa ttg gga atc    384
Asp Phe Phe Leu Gly Trp Thr Asn Ser Leu Ala Ser Gln Leu Gly Ile
        115                 120                 125 ccg cgt ctt gta ttt tgg cca tcg ggt gtt caa cga tct tcg ctc gta    432
Pro Arg Leu Val Phe Trp Pro Ser Gly Val Gln Arg Ser Ser Leu Val
    130                 135                 140 gat tat ata tgg caa aat gat caa ttg tca gat tcc gac cac caa atc    480
Asp Tyr Ile Trp Gln Asn Asp Gln Leu Ser Asp Ser Asp His Gln Ile
145                 150                 155                 160 caa gac aat tct gtg att tca ttt cct gat gta ccg aac tca cca gca    528
Gln Asp Asn Ser Val Ile Ser Phe Pro Asp Val Pro Asn Ser Pro Ala
                165                 170                 175 tac cca aag tgg caa gcc tgt ggt ctt agt act cag tat aag aaa gga    576
Tyr Pro Lys Trp Gln Ala Cys Gly Leu Ser Thr Gln Tyr Lys Lys Gly
            180                 185                 190 gac cca agc tgg gaa ttt ttc aag aat ggt gtt tta gca aat aca caa    624
Asp Pro Ser Trp Glu Phe Phe Lys Asn Gly Val Leu Ala Asn Thr Gln
        195                 200                 205 agc tgg ggt gct atc tat aat tct ttt agg gac tta gaa gga gtt tat    672
Ser Trp Gly Ala Ile Tyr Asn Ser Phe Arg Asp Leu Glu Gly Val Tyr
    210                 215                 220
```

```
att gat tat atc aag aag aaa atg ggc cat gga aga gtt tgg gca gtt      720
Ile Asp Tyr Ile Lys Lys Lys Met Gly His Gly Arg Val Trp Ala Val
225                 230                 235                 240 ggg cca ctt ttg ccc gca aat gat gca tca aaa cgc ggt gga tca tgt      768
Gly Pro Leu Leu Pro Ala Asn Asp Ala Ser Lys Arg Gly Gly Ser Cys
                245                 250                 255 gta atg ccc att gat gat gta atg aca tgg tta gat acg aaa acc aat      816
Val Met Pro Ile Asp Asp Val Met Thr Trp Leu Asp Thr Lys Thr Asn
            260                 265                 270 tca gac aat tct gtt gtt tat gtc tgt ttt ggt agt cga gta gag tta      864
Ser Asp Asn Ser Val Val Tyr Val Cys Phe Gly Ser Arg Val Glu Leu
        275                 280                 285 aca acc gag caa cta gat tct tta gca gct gca ctt gaa atc agt ggg      912
Thr Thr Glu Gln Leu Asp Ser Leu Ala Ala Ala Leu Glu Ile Ser Gly
    290                 295                 300 gtt cat ttc ata ttg tgt gtg aag tta cat cag gag atc tca aag gag      960
Val His Phe Ile Leu Cys Val Lys Leu His Gln Glu Ile Ser Lys Glu
305                 310                 315                 320 tac gaa gat cga gtg gct gga aga gga ttg atc ata agg gga tgg gca     1008
Tyr Glu Asp Arg Val Ala Gly Arg Gly Leu Ile Ile Arg Gly Trp Ala
                325                 330                 335 cca caa gtc gcg ata tta agg cat cga gct gtg ggt gcg ttt ttg act     1056
Pro Gln Val Ala Ile Leu Arg His Arg Ala Val Gly Ala Phe Leu Thr
            340                 345                 350 cat tgt ggg tgg aat tcc ata tta gaa gga ata gct gcg ggt gtg gtg     1104
His Cys Gly Trp Asn Ser Ile Leu Glu Gly Ile Ala Ala Gly Val Val
        355                 360                 365 atg cta aca tgg cca atg ggt gct gat caa ttt acg aat gct aac tta     1152
Met Leu Thr Trp Pro Met Gly Ala Asp Gln Phe Thr Asn Ala Asn Leu
    370                 375                 380 tta gta gat gag tta aag gtg gcg atg aag gct tgt gaa ggc ggt gat     1200
Leu Val Asp Glu Leu Lys Val Ala Met Lys Ala Cys Glu Gly Gly Asp
385                 390                 395                 400 agt aac gtg ccc aac cct gcc atg ttg gct aat gta tta gcc gag tca     1248
Ser Asn Val Pro Asn Pro Ala Met Leu Ala Asn Val Leu Ala Glu Ser
                405                 410                 415 ata aat ggt ggt agg gct gag agg gag aga gtg acg gag ctg tgt gat     1296
Ile Asn Gly Gly Arg Ala Glu Arg Glu Arg Val Thr Glu Leu Cys Asp
            420                 425                 430 gct gcc ttg aag gct gtt cag agt gga aac ggt agt tca gca aaa gat     1344
Ala Ala Leu Lys Ala Val Gln Ser Gly Asn Gly Ser Ser Ala Lys Asp
        435                 440                 445 ttg gac tcg cta act aat caa ctc aat ggt tta aag gta aaa att aac     1392
Leu Asp Ser Leu Thr Asn Gln Leu Asn Gly Leu Lys Val Lys Ile Asn
    450                 455                 460 taa                                                                  1395

<210> SEQ ID NO 11
<211> LENGTH: 464
<212> TYPE: PRT
<213> ORGANISM: Nemophila menziesii

<400> SEQUENCE: 11

Met Pro Ser Ile Leu Ser Asn Ser Ala His Ile Leu Leu Phe Pro Phe
1               5                   10                  15

Pro Thr Ser Gly His Ile Ile Pro Ile Leu Asp Leu Ala Asn Gln Leu
            20                  25                  30

Leu Ala Arg Gly Leu Thr Ile Thr Ile Leu Ile Thr Pro Ala Asn Leu
        35                  40                  45
```

-continued

```
Thr Leu Leu Ser Thr Gln Leu Ile Glu Leu Asp Arg Leu Gly Ser Leu
 50                  55                  60
His Thr Leu Val Leu Pro Phe Pro Asn Pro Asn Pro Ser Glu Thr
 65                  70                  75                  80
Ser Leu Ala Ala Arg Val His Ala Ser Ser Gln Leu Ser Asn Thr Ile
                 85                  90                  95
Ile Gln Trp Phe Gln Ser His Thr Ser Pro Val Ala Ile Val Ser
            100                 105                 110
Asp Phe Phe Leu Gly Trp Thr Asn Ser Leu Ala Ser Gln Leu Gly Ile
            115                 120                 125
Pro Arg Leu Val Phe Trp Pro Ser Gly Val Gln Arg Ser Ser Leu Val
130                 135                 140
Asp Tyr Ile Trp Gln Asn Asp Gln Leu Ser Asp Ser Asp His Gln Ile
145                 150                 155                 160
Gln Asp Asn Ser Val Ile Ser Phe Pro Asp Val Pro Asn Ser Pro Ala
                165                 170                 175
Tyr Pro Lys Trp Gln Ala Cys Gly Leu Ser Thr Gln Tyr Lys Lys Gly
            180                 185                 190
Asp Pro Ser Trp Glu Phe Phe Lys Asn Gly Val Leu Ala Asn Thr Gln
            195                 200                 205
Ser Trp Gly Ala Ile Tyr Asn Ser Phe Arg Asp Leu Glu Gly Val Tyr
210                 215                 220
Ile Asp Tyr Ile Lys Lys Lys Met Gly His Gly Arg Val Trp Ala Val
225                 230                 235                 240
Gly Pro Leu Leu Pro Ala Asn Asp Ala Ser Lys Arg Gly Gly Ser Cys
                245                 250                 255
Val Met Pro Ile Asp Asp Val Met Thr Trp Leu Asp Thr Lys Thr Asn
            260                 265                 270
Ser Asp Asn Ser Val Val Tyr Val Cys Phe Gly Ser Arg Val Glu Leu
            275                 280                 285
Thr Thr Glu Gln Leu Asp Ser Leu Ala Ala Ala Leu Glu Ile Ser Gly
290                 295                 300
Val His Phe Ile Leu Cys Val Lys Leu His Gln Glu Ile Ser Lys Glu
305                 310                 315                 320
Tyr Glu Asp Arg Val Ala Gly Arg Gly Leu Ile Ile Arg Gly Trp Ala
                325                 330                 335
Pro Gln Val Ala Ile Leu Arg His Arg Ala Val Gly Ala Phe Leu Thr
            340                 345                 350
His Cys Gly Trp Asn Ser Ile Leu Glu Gly Ile Ala Ala Gly Val Val
            355                 360                 365
Met Leu Thr Trp Pro Met Gly Ala Asp Gln Phe Thr Asn Ala Asn Leu
370                 375                 380
Leu Val Asp Glu Leu Lys Val Ala Met Lys Ala Cys Glu Gly Gly Asp
385                 390                 395                 400
Ser Asn Val Pro Asn Pro Ala Met Leu Ala Asn Val Leu Ala Glu Ser
                405                 410                 415
Ile Asn Gly Gly Arg Ala Glu Arg Glu Arg Val Thr Glu Leu Cys Asp
            420                 425                 430
Ala Ala Leu Lys Ala Val Gln Ser Gly Asn Gly Ser Ser Ala Lys Asp
            435                 440                 445
Leu Asp Ser Leu Thr Asn Gln Leu Asn Gly Leu Lys Val Lys Ile Asn
450                 455                 460
```

<210> SEQ ID NO 12
<211> LENGTH: 1428
<212> TYPE: DNA
<213> ORGANISM: Nemophila menziesii
<220> FEATURE:
<221> NAME/KEY: misc_feature
<222> LOCATION: (1)..(1428)
<223> OTHER INFORMATION: NmGT4
<220> FEATURE:
<221> NAME/KEY: CDS
<222> LOCATION: (1)..(1425)

<400> SEQUENCE: 12

| | | | | | | | | | | | | | | | | |
|---|---|---|---|---|---|---|---|---|---|---|---|---|---|---|---|---|
| atg | gca | gct | cag | ctt | cat | gtt | gtc | ttc | ttt | cca | ttc | atg | gct | caa | ggc | 48 |
| Met | Ala | Ala | Gln | Leu | His | Val | Val | Phe | Phe | Pro | Phe | Met | Ala | Gln | Gly | |
| 1 | | | | 5 | | | | | 10 | | | | | 15 | | |
| cac | tta | ata | ccc | acc | ctt | gaa | atg | gtc | aaa | ctc | ttc | tct | tct | cgt | ggt | 96 |
| His | Leu | Ile | Pro | Thr | Leu | Glu | Met | Val | Lys | Leu | Phe | Ser | Ser | Arg | Gly | |
| | | | 20 | | | | | 25 | | | | | 30 | | | |
| ctt | aag | acc | acc | ata | gtc | acc | act | aaa | ttt | tat | gct | cct | gcg | gtt | aca | 144 |
| Leu | Lys | Thr | Thr | Ile | Val | Thr | Thr | Lys | Phe | Tyr | Ala | Pro | Ala | Val | Thr | |
| | | 35 | | | | | 40 | | | | | 45 | | | | |
| aaa | tcc | ata | gaa | aaa | acc | aaa | cat | aca | gga | aac | caa | atc | aat | ata | att | 192 |
| Lys | Ser | Ile | Glu | Lys | Thr | Lys | His | Thr | Gly | Asn | Gln | Ile | Asn | Ile | Ile | |
| 50 | | | | | 55 | | | | | 60 | | | | | | |
| atc | ata | aaa | ttc | cct | tct | gcc | gag | gtt | gga | tta | ccc | gaa | gga | tct | gaa | 240 |
| Ile | Ile | Lys | Phe | Pro | Ser | Ala | Glu | Val | Gly | Leu | Pro | Glu | Gly | Ser | Glu | |
| 65 | | | | | 70 | | | | | 75 | | | | | 80 | |
| agt | ctc | gac | aaa | ctg | aaa | tca | cct | gac | atg | ttc | atg | aaa | ttt | ttc | aag | 288 |
| Ser | Leu | Asp | Lys | Leu | Lys | Ser | Pro | Asp | Met | Phe | Met | Lys | Phe | Phe | Lys | |
| | | | | 85 | | | | | 90 | | | | | 95 | | |
| gct | ctt | tct | tta | tta | caa | gaa | cca | ttt | gag | caa | atc | tta | caa | gaa | ttg | 336 |
| Ala | Leu | Ser | Leu | Leu | Gln | Glu | Pro | Phe | Glu | Gln | Ile | Leu | Gln | Glu | Leu | |
| | | | | 100 | | | | | 105 | | | | | 110 | | |
| tct | cct | gat | tgt | atc | gtt | tct | gat | atg | ttc | ttc | cca | tgg | act | act | gct | 384 |
| Ser | Pro | Asp | Cys | Ile | Val | Ser | Asp | Met | Phe | Phe | Pro | Trp | Thr | Thr | Ala | |
| | | | 115 | | | | | 120 | | | | | 125 | | | |
| tca | gct | gct | aaa | ttc | gat | atc | ccg | aga | ttt | gtt | ttc | cat | ggt | tta | agt | 432 |
| Ser | Ala | Ala | Lys | Phe | Asp | Ile | Pro | Arg | Phe | Val | Phe | His | Gly | Leu | Ser | |
| | | 130 | | | | | 135 | | | | | 140 | | | | |
| ctt | ttc | gca | ctg | tgt | gtt | tcg | gag | aat | atg | aga | ttc | tac | aag | cca | ttc | 480 |
| Leu | Phe | Ala | Leu | Cys | Val | Ser | Glu | Asn | Met | Arg | Phe | Tyr | Lys | Pro | Phe | |
| 145 | | | | | 150 | | | | | 155 | | | | | 160 | |
| aag | aat | ctg | gga | tct | gaa | tca | tta | gat | tca | gaa | ccg | gtc | atg | ttg | cct | 528 |
| Lys | Asn | Leu | Gly | Ser | Glu | Ser | Leu | Asp | Ser | Glu | Pro | Val | Met | Leu | Pro | |
| | | | | 165 | | | | | 170 | | | | | 175 | | |
| gat | ttc | ccg | aat | cag | att | gag | ttc | agt | aaa | gtt | caa | gtc | cct | gaa | ttt | 576 |
| Asp | Phe | Pro | Asn | Gln | Ile | Glu | Phe | Ser | Lys | Val | Gln | Val | Pro | Glu | Phe | |
| | | | 180 | | | | | 185 | | | | | 190 | | | |
| gaa | gtt | ggt | gaa | agt | aaa | aac | gag | atc | atg | gag | ttg | tta | aat | caa | gtt | 624 |
| Glu | Val | Gly | Glu | Ser | Lys | Asn | Glu | Ile | Met | Glu | Leu | Leu | Asn | Gln | Val | |
| | | 195 | | | | | 200 | | | | | 205 | | | | |
| aag | gaa | tcc | gag | gtt | aaa | agc | tat | ggg | att | att | atc | aat | agt | ttt | aat | 672 |
| Lys | Glu | Ser | Glu | Val | Lys | Ser | Tyr | Gly | Ile | Ile | Ile | Asn | Ser | Phe | Asn | |
| 210 | | | | | 215 | | | | | 220 | | | | | | |
| gaa | ctt | gag | aaa | gat | tac | gtt | gat | tac | tat | aga | aac | gtt | tgg | gga | aga | 720 |
| Glu | Leu | Glu | Lys | Asp | Tyr | Val | Asp | Tyr | Tyr | Arg | Asn | Val | Trp | Gly | Arg | |
| 225 | | | | | 230 | | | | | 235 | | | | | 240 | |
| cga | gca | tgg | ctt | ctt | ggt | cct | tta | tcg | tta | tct | aat | cgc | gat | gat | gaa | 768 |
| Arg | Ala | Trp | Leu | Leu | Gly | Pro | Leu | Ser | Leu | Ser | Asn | Arg | Asp | Asp | Glu | |
| | | | | 245 | | | | | 250 | | | | | 255 | | |
| gta | aaa | gat | cag | aca | gat | gaa | cac | gga | tct | tta | aaa | tgg | ctt | gat | tcg | 816 |

| | | | | | | | | | | | | | | |
|---|---|---|---|---|---|---|---|---|---|---|---|---|---|---|
|Val|Lys|Asp|Gln|Thr|Asp|Glu|His|Gly|Ser|Leu|Lys|Trp|Leu|Asp|Ser|
| | | |260| | | |265| | | |270| | | |

```
aag aaa cca gat tca gtt att tac gta tgt ttt gga agt gta gcg cct    864
Lys Lys Pro Asp Ser Val Ile Tyr Val Cys Phe Gly Ser Val Ala Pro
            275                 280                 285 tta agt agt tcg caa tta cac gag att gct tta gga ctt gaa tct tcg    912
Leu Ser Ser Ser Gln Leu His Glu Ile Ala Leu Gly Leu Glu Ser Ser
        290                 295                 300 ggt caa cag ttc att tgg gta gtc aag gaa cgt gaa gat ggt gag aaa    960
Gly Gln Gln Phe Ile Trp Val Val Lys Glu Arg Glu Asp Gly Glu Lys
305                 310                 315                 320 tgg tta cct gaa gga ttt gag gag aga att aag gat aag gga tta atc    1008
Trp Leu Pro Glu Gly Phe Glu Glu Arg Ile Lys Asp Lys Gly Leu Ile
                325                 330                 335 ata cga ggg tgg gcc cca caa gta tcg att ctt gaa cat gaa tct aca    1056
Ile Arg Gly Trp Ala Pro Gln Val Ser Ile Leu Glu His Glu Ser Thr
            340                 345                 350 ggg ggt ttc gtg act cat tgt ggg tgg aac tca gtg ctc gag gct gta    1104
Gly Gly Phe Val Thr His Cys Gly Trp Asn Ser Val Leu Glu Ala Val
        355                 360                 365 tct gca ggg gta gtt atg gca aca ttg cct aca ttt gcg gaa caa cct    1152
Ser Ala Gly Val Val Met Ala Thr Leu Pro Thr Phe Ala Glu Gln Pro
370                 375                 380 ttt aac gaa aag ctg tta acg aaa gtt ttg aag att ggg ata cct att    1200
Phe Asn Glu Lys Leu Leu Thr Lys Val Leu Lys Ile Gly Ile Pro Ile
385                 390                 395                 400 ggt tca cca tta tcg aat aga ggt aag agt ggt gtg aaa aaa gaa gag    1248
Gly Ser Pro Leu Ser Asn Arg Gly Lys Ser Gly Val Lys Lys Glu Glu
                405                 410                 415 ata gct gag gcg atg aaa ggg att atg gaa ggt gaa gaa gct ctt gaa    1296
Ile Ala Glu Ala Met Lys Gly Ile Met Glu Gly Glu Glu Ala Leu Glu
            420                 425                 430 atg aga atc cga gca aag agt ttg aaa gag atg gct tgg aaa gct gtt    1344
Met Arg Ile Arg Ala Lys Ser Leu Lys Glu Met Ala Trp Lys Ala Val
        435                 440                 445 gaa gaa gga ggt tct tct tat aat gat ttg act tct ttg att gat gga    1392
Glu Glu Gly Gly Ser Ser Tyr Asn Asp Leu Thr Ser Leu Ile Asp Gly
450                 455                 460 gtc aaa gct tat cgt tca caa tca aac aag ata tga                    1428
Val Lys Ala Tyr Arg Ser Gln Ser Asn Lys Ile
465                 470                 475
```

<210> SEQ ID NO 13
<211> LENGTH: 475
<212> TYPE: PRT
<213> ORGANISM: Nemophila menziesii

<400> SEQUENCE: 13

```
Met Ala Ala Gln Leu His Val Phe Phe Pro Phe Met Ala Gln Gly
1               5                   10                  15

His Leu Ile Pro Thr Leu Glu Met Val Lys Leu Phe Ser Arg Gly
                20                  25                  30

Leu Lys Thr Thr Ile Val Thr Thr Lys Phe Tyr Ala Pro Ala Val Thr
            35                  40                  45

Lys Ser Ile Glu Lys Thr Lys His Thr Gly Asn Gln Ile Asn Ile Ile
        50                  55                  60

Ile Ile Lys Phe Pro Ser Ala Glu Val Gly Leu Pro Glu Gly Ser Glu
65                  70                  75                  80

Ser Leu Asp Lys Leu Lys Ser Pro Asp Met Phe Met Lys Phe Phe Lys
```

```
            85                  90                  95
Ala Leu Ser Leu Leu Gln Glu Pro Phe Glu Gln Ile Leu Gln Glu Leu
            100                 105                 110

Ser Pro Asp Cys Ile Val Ser Asp Met Phe Phe Pro Trp Thr Thr Ala
            115                 120                 125

Ser Ala Ala Lys Phe Asp Ile Pro Arg Phe Val Phe His Gly Leu Ser
            130                 135                 140

Leu Phe Ala Leu Cys Val Ser Glu Asn Met Arg Phe Tyr Lys Pro Phe
145                 150                 155                 160

Lys Asn Leu Gly Ser Glu Ser Leu Asp Ser Glu Pro Val Met Leu Pro
                165                 170                 175

Asp Phe Pro Asn Gln Ile Glu Phe Ser Lys Val Gln Val Pro Glu Phe
                180                 185                 190

Glu Val Gly Glu Ser Lys Asn Glu Ile Met Glu Leu Leu Asn Gln Val
                195                 200                 205

Lys Glu Ser Glu Val Lys Ser Tyr Gly Ile Ile Asn Ser Phe Asn
210                 215                 220

Glu Leu Glu Lys Asp Tyr Val Asp Tyr Tyr Arg Asn Val Trp Gly Arg
225                 230                 235                 240

Arg Ala Trp Leu Leu Gly Pro Leu Ser Leu Ser Asn Arg Asp Asp Glu
                245                 250                 255

Val Lys Asp Gln Thr Asp Glu His Gly Ser Leu Lys Trp Leu Asp Ser
                260                 265                 270

Lys Lys Pro Asp Ser Val Ile Tyr Val Cys Phe Gly Ser Val Ala Pro
                275                 280                 285

Leu Ser Ser Ser Gln Leu His Glu Ile Ala Leu Gly Leu Glu Ser Ser
                290                 295                 300

Gly Gln Gln Phe Ile Trp Val Val Lys Glu Arg Glu Asp Gly Glu Lys
305                 310                 315                 320

Trp Leu Pro Glu Gly Phe Glu Glu Arg Ile Lys Asp Lys Gly Leu Ile
                325                 330                 335

Ile Arg Gly Trp Ala Pro Gln Val Ser Ile Leu Glu His Glu Ser Thr
                340                 345                 350

Gly Gly Phe Val Thr His Cys Gly Trp Asn Ser Val Leu Glu Ala Val
                355                 360                 365

Ser Ala Gly Val Val Met Ala Thr Leu Pro Thr Phe Ala Glu Gln Pro
                370                 375                 380

Phe Asn Glu Lys Leu Leu Thr Lys Val Leu Lys Ile Gly Ile Pro Ile
385                 390                 395                 400

Gly Ser Pro Leu Ser Asn Arg Gly Lys Ser Gly Val Lys Lys Glu Glu
                405                 410                 415

Ile Ala Glu Ala Met Lys Gly Ile Met Glu Gly Glu Ala Leu Glu
                420                 425                 430

Met Arg Ile Arg Ala Lys Ser Leu Lys Glu Met Ala Trp Lys Ala Val
                435                 440                 445

Glu Glu Gly Gly Ser Ser Tyr Asn Asp Leu Thr Ser Leu Ile Asp Gly
                450                 455                 460

Val Lys Ala Tyr Arg Ser Gln Ser Asn Lys Ile
465                 470                 475

<210> SEQ ID NO 14
<211> LENGTH: 457
<212> TYPE: PRT
<213> ORGANISM: Antirrhinum majus
```

<400> SEQUENCE: 14

Met Gly Glu Glu Tyr Lys Lys Thr His Thr Ile Val Phe His Thr Ser
1               5                   10                  15

Glu Glu His Leu Asn Ser Ser Ile Ala Leu Ala Lys Phe Ile Thr Lys
            20                  25                  30

His His Ser Ser Ile Ser Ile Thr Ile Ile Ser Thr Ala Pro Ala Glu
        35                  40                  45

Ser Ser Glu Val Ala Lys Ile Ile Asn Asn Pro Ser Ile Thr Tyr Arg
    50                  55                  60

Gly Leu Thr Ala Val Ala Leu Pro Glu Asn Leu Thr Ser Asn Ile Asn
65                  70                  75                  80

Lys Asn Pro Val Glu Leu Phe Phe Glu Ile Pro Arg Leu Gln Asn Ala
                85                  90                  95

Asn Leu Arg Glu Ala Leu Leu Asp Ile Ser Arg Lys Ser Asp Ile Lys
            100                 105                 110

Ala Leu Ile Ile Asp Phe Phe Cys Asn Ala Ala Phe Glu Val Ser Thr
        115                 120                 125

Ser Met Asn Ile Pro Thr Tyr Phe Asp Val Ser Gly Gly Ala Phe Leu
    130                 135                 140

Leu Cys Thr Phe Leu His His Pro Thr Leu His Gln Thr Val Arg Gly
145                 150                 155                 160

Asp Ile Ala Asp Leu Asn Asp Ser Val Glu Met Pro Gly Phe Pro Leu
                165                 170                 175

Ile His Ser Ser Asp Leu Pro Met Ser Leu Phe Tyr Arg Lys Thr Asn
            180                 185                 190

Val Tyr Lys His Phe Leu Asp Thr Ser Leu Asn Met Arg Lys Ser Ser
        195                 200                 205

Gly Ile Leu Val Asn Thr Phe Val Ala Leu Glu Phe Arg Ala Lys Glu
    210                 215                 220

Ala Leu Ser Asn Gly Leu Tyr Gly Pro Thr Pro Leu Tyr Leu Leu
225                 230                 235                 240

Ser His Thr Ile Ala Glu Pro His Asp Thr Lys Val Leu Val Asn Gln
                245                 250                 255

His Glu Cys Leu Ser Trp Leu Asp Leu Gln Pro Ser Lys Ser Val Ile
            260                 265                 270

Phe Leu Cys Phe Gly Arg Arg Gly Ala Phe Ser Ala Gln Gln Leu Lys
        275                 280                 285

Glu Ile Ala Ile Gly Leu Glu Lys Ser Gly Cys Arg Phe Leu Trp Leu
    290                 295                 300

Ala Arg Ile Ser Pro Glu Met Asp Leu Asn Ala Leu Leu Pro Glu Gly
305                 310                 315                 320

Phe Leu Ser Arg Thr Lys Gly Val Gly Phe Val Thr Asn Thr Trp Val
                325                 330                 335

Pro Gln Lys Glu Val Leu Ser His Asp Ala Val Gly Gly Phe Val Thr
            340                 345                 350

His Cys Gly Trp Ser Ser Val Leu Glu Ala Leu Ser Phe Gly Val Pro
        355                 360                 365

Met Ile Gly Trp Pro Leu Tyr Ala Glu Gln Arg Ile Asn Arg Val Phe
    370                 375                 380

Met Val Glu Glu Ile Lys Val Ala Leu Pro Leu Asp Glu Glu Asp Gly
385                 390                 395                 400

Phe Val Thr Ala Met Glu Leu Glu Lys Arg Val Arg Glu Leu Met Glu

```
                405                 410                 415
Ser Val Lys Gly Lys Glu Val Lys Arg Arg Val Ala Glu Leu Lys Ile
            420                 425                 430

Ser Thr Lys Ala Ala Val Ser Lys Gly Gly Ser Ser Leu Ala Ser Leu
            435                 440                 445

Glu Lys Phe Ile Asn Ser Val Thr Arg
            450                 455

<210> SEQ ID NO 15
<211> LENGTH: 473
<212> TYPE: PRT
<213> ORGANISM: Rosa hybrid cultivar

<400> SEQUENCE: 15

Met Gly Gly Asp Ala Ile Val Leu Tyr Pro Tyr Pro Gly Leu Gly His
1               5                   10                  15

Leu Ile Ser Met Val Glu Leu Gly Lys Leu Leu Leu Thr His His Pro
            20                  25                  30

Ser Phe Ser Ile Thr Ile Leu Ala Ser Thr Ala Pro Thr Thr Ile Ala
        35                  40                  45

Ala Thr Ala Lys Leu Val Ala Ser Ser Asn Asp Gln Leu Thr Asn Tyr
    50                  55                  60

Ile Lys Ala Val Ser Ala Asp Asn Pro Ala Ile Asn Phe His His Leu
65                  70                  75                  80

Pro Thr Ile Ser Ser Leu Pro Glu His Ile Glu Lys Leu Asn Leu Pro
                85                  90                  95

Phe Glu Tyr Ala Arg Leu Gln Ile Pro Asn Ile Leu Gln Val Leu Gln
            100                 105                 110

Thr Leu Lys Ser Ser Leu Lys Ala Leu Ile Leu Asp Met Phe Cys Asp
        115                 120                 125

Ala Leu Phe Asp Val Thr Lys Asp Leu Asn Ile Pro Thr Phe Tyr Phe
    130                 135                 140

Tyr Thr Ser Ala Gly Arg Ser Leu Ala Val Leu Leu Asn Ile Pro Thr
145                 150                 155                 160

Phe His Arg Thr Thr Asn Ser Leu Ser Asp Phe Gly Asp Val Pro Ile
                165                 170                 175

Ser Ile Ser Gly Met Pro Pro Ile Pro Val Ser Ala Met Pro Lys Leu
            180                 185                 190

Leu Phe Asp Arg Ser Thr Asn Phe Tyr Lys Ser Phe Leu Ser Thr Ser
        195                 200                 205

Thr His Met Ala Lys Ser Asn Gly Ile Ile Leu Asn Thr Phe Asp Leu
    210                 215                 220

Leu Glu Glu Arg Ala Leu Lys Ala Leu Arg Ala Gly Leu Cys Leu Pro
225                 230                 235                 240

Asn Gln Pro Thr Pro Pro Ile Phe Thr Val Gly Pro Leu Ile Ser Gly
                245                 250                 255

Lys Ser Gly Asp Asn Asp Glu His Glu Ser Leu Lys Trp Leu Asn Asn
            260                 265                 270

Gln Pro Lys Asp Ser Val Val Phe Leu Cys Phe Gly Ser Met Gly Val
        275                 280                 285

Phe Ser Ile Lys Gln Leu Glu Ala Met Ala Leu Gly Leu Glu Lys Ser
    290                 295                 300

Gly Gln Arg Phe Leu Trp Val Val Arg Asn Pro Pro Ile Glu Glu Leu
305                 310                 315                 320
```

-continued

```
Pro Val Glu Glu Pro Ser Leu Glu Glu Ile Leu Pro Lys Gly Phe Val
            325                 330                 335

Glu Arg Thr Lys Asp Arg Gly Leu Val Val Arg Lys Trp Ala Pro Gln
            340                 345                 350

Val Glu Val Leu Ser His Asp Ser Val Gly Gly Phe Val Thr His Cys
        355                 360                 365

Gly Trp Asn Ser Val Leu Glu Ala Val Cys Asn Gly Val Pro Met Val
    370                 375                 380

Ala Trp Pro Leu Tyr Ala Glu Gln Lys Leu Gly Arg Val Phe Leu Val
385                 390                 395                 400

Glu Glu Met Lys Val Ala Val Gly Val Lys Glu Ser Glu Thr Gly Phe
                405                 410                 415

Val Ser Ala Asp Glu Leu Glu Lys Arg Val Arg Glu Leu Met Asp Ser
            420                 425                 430

Glu Ser Gly Asp Glu Ile Arg Gly Arg Val Ser Glu Phe Ser Asn Gly
            435                 440                 445

Gly Val Lys Ala Lys Glu Glu Gly Gly Ser Ser Val Ala Ser Leu Ala
    450                 455                 460

Lys Leu Ala Gln Leu Trp Lys Gln Lys
465                 470
```